US012583850B2

(12) United States Patent
Androphy et al.

(10) Patent No.: US 12,583,850 B2
(45) Date of Patent: Mar. 24, 2026

(54) SMALL MOLECULE ANTIVIRAL DRUG TREATMENT FOR HUMAN PAPILLOMAVIRUS INFECTIONS

(71) Applicants: THE TRUSTEES OF INDIANA UNIVERSITY, Bloomington, IN (US); KOVINA THERAPEUTICS INC., Indianapolis, IN (US)

(72) Inventors: Elliot J. Androphy, Indianapolis, IN (US); Samy Meroueh, Carmel, IN (US); Anne Rietz, Indianapolis, IN (US); Zhijan Lu, Indianapolis, IN (US)

(73) Assignees: THE TRUSTEES OF INDIANA UNIVERSITY, Bloomington, IN (US); KOVINA THERAPEUTICS INC., Indianapolis, IN (US)

( * ) Notice: Subject to any disclaimer, the term of this patent is extended or adjusted under 35 U.S.C. 154(b) by 0 days.

(21) Appl. No.: 19/293,960

(22) Filed: Aug. 7, 2025

(65) Prior Publication Data

US 2025/0361229 A1 Nov. 27, 2025

Related U.S. Application Data

(63) Continuation of application No. 18/740,140, filed on Jun. 11, 2024.

(60) Provisional application No. 63/507,895, filed on Jun. 13, 2023.

(51) Int. Cl.

| | |
|---|---|
| ***C07D 413/14*** | (2006.01) |
| ***A61K 31/517*** | (2006.01) |
| ***A61K 31/519*** | (2006.01) |
| ***A61K 31/5377*** | (2006.01) |
| ***C07D 403/04*** | (2006.01) |
| ***C07D 403/14*** | (2006.01) |
| ***C07D 471/04*** | (2006.01) |
| ***C07D 487/08*** | (2006.01) |
| ***C07D 487/10*** | (2006.01) |
| ***C07D 495/04*** | (2006.01) |

(52) U.S. Cl.

CPC .......... *C07D 413/14* (2013.01); *A61K 31/517* (2013.01); *A61K 31/519* (2013.01); *A61K 31/5377* (2013.01); *C07D 403/04* (2013.01); *C07D 403/14* (2013.01); *C07D 471/04* (2013.01); *C07D 487/08* (2013.01); *C07D 487/10* (2013.01); *C07D 495/04* (2013.01)

(58) Field of Classification Search

None

See application file for complete search history.

(56) References Cited

U.S. PATENT DOCUMENTS

| | | | | |
|---|---|---|---|---|
| 3,710,789 | A | 1/1973 | Ersek | |
| 4,681,888 | A | 7/1987 | Esanu | |
| 5,656,721 | A | 8/1997 | Monika | |
| 7,019,000 | B1 | 3/2006 | Bernard | |
| 8,343,980 | B2 | 1/2013 | Gonzalez, III | |
| 10,338,000 | B2 | 7/2019 | Gumennik | |
| 10,567,829 | B2 | 2/2020 | Kleinerman | |
| 11,628,158 | B2 | 4/2023 | Androphy | |
| 11,931,356 | B1 * | 3/2024 | Androphy | A61K 31/496 |
| 2003/0119855 | A1 | 6/2003 | Okano | |
| 2008/0046932 | A1 | 2/2008 | Stallings | |
| 2008/0103162 | A1 | 5/2008 | Oyama | |
| 2009/0027462 | A1 | 1/2009 | Berg | |
| 2009/0274621 | A1 | 11/2009 | Wegrzyn | |
| 2010/0010572 | A1 | 1/2010 | Skelton | |
| 2010/0105722 | A1 | 4/2010 | Kuehnert | |
| 2010/0316088 | A1 | 12/2010 | Bayindir | |
| 2016/0021499 | A1 | 1/2016 | Viswanadham | |
| 2016/0112752 | A1 | 4/2016 | Selvaraj | |
| 2016/0214994 | A1 | 7/2016 | Xu | |
| 2017/0036398 | A1 | 2/2017 | Gumennik | |
| 2017/0281788 | A1 | 10/2017 | Dimarchi | |
| 2018/0057559 | A1 | 3/2018 | Weiss | |
| 2020/0019736 | A1 | 1/2020 | Komine | |
| 2020/0197369 | A1 | 6/2020 | Tang | |
| 2021/0330864 | A1 | 10/2021 | Gumennik | |
| 2021/0333131 | A1 | 10/2021 | Gumennik | |
| 2024/0425493 | A1 | 12/2024 | Androphy | |

FOREIGN PATENT DOCUMENTS

| | | | |
|---|---|---|---|
| WO | 2012135416 | A1 | 10/2012 |
| WO | 2013142253 | A2 | 9/2013 |
| WO | 2022061251 | A1 | 3/2022 |

OTHER PUBLICATIONS

Lande, R., and Arnold, S. J., "The measurement of selection on correlated characters," 1983, Evolution, 37 pp. 1210-1226.

Langmead, B., and Salzberg, S. L., "Fast gapped-read alignment with Bowtie 2," 2012, Nature Methods, 9(4) pp. 357-359.

Lanyon-Hogg, Thomas et al.: "Click chemistry armed enzyme-linked immunosorbent assay to measure palmitoylation by hedgehof acyltransferase", Analytical Biochemistry, Academic Press, Amsterdam, NL, vol. 490, Sep. 1, 2015 (Sep. 1, 2015), pp. 66-72, XP029298525, ISSN: 0003-2697, DOI: 10.1016/J.AB.2015.08.025.

Lanyon-Hogg, Thomas et al.: "Microfluidic Mobility Shift Assay for Real-Time Analysis of Peptide N-Palmitoylation", SLAS Discovery: Advancing Life Sciences R&D, vol. 22, No. 4, 2017 (Sep. 1, 2017), pp. 418-424, XP93147605, ISSN: 2472-5552, DOI: 10.1177/2472555216689529.

Lattari, J., "Improving bioprocess control and optimization: in-line dissolved carbon dioxide measurement in bioproduction," 2017, Genetic Engineering & Biotechnology News, 38 pp. 24-25.

Lau, J. A., and Lennon, J. T., "Rapid responses of soil microorganisms improve plant fitness in novel environments," 2012, Proceedings of the National Academy of Sciences of the United States of America, 109 pp. 14058-14062.

Lee, J. et al., "Conductive fiber-based ultrasensitive textile pressure sensor for wearable electronics," 2015, Advanced Materials, 27(15) pp. 2433-2439.

(Continued)

*Primary Examiner* — Svetlana M Ivanova

(74) *Attorney, Agent, or Firm* — Barnes & Thornburg LLP

(57) ABSTRACT

Compositions and methods are provided for treating HPV infections including pre-malignant and cancers. Compounds that specifically bind to the HPV E6 protein and inactivate the protein are disclosed.

30 Claims, 32 Drawing Sheets

(56) References Cited

OTHER PUBLICATIONS

Lee, S. M., et al., "Bacterial colonization factors control specificity and stability of the gut microbiota," 2013, Nature, 501 pp. 426-429.
Lennon, J. T., and Jones, S. E., "Microbial seed banks: the ecological and evolutionary implications of dormancy," 2011, Nature Reviews Microbiology, 9 pp. 119-130.
Lennon, J. T., and Lehmkuhl, B. K., "A trait-based approach to bacterial biofilms in soil," 2016, Environmental Microbiology, 18 pp. 2732-2742.
Lennon, J. T., and Martiny, J. B. H., "Rapid evolution buffers ecosystem impacts of viruses in a microbial food web," 2008, Ecology Letters, 11 pp. 1178-1188.
Lennon, J. T., et al., "How, when, and where relic DNA biases estimates of microbial diversity," 2018, Mbio 9: e00637-00618.
Lennon, J. T., et al., "Mapping the niche space of soil microorganisms using taxonomy and traits," 2012, Ecology, 93 pp. 1867-1879.
Leone, A., et al., "Development of a prototype malaxer to investigate the influence of oxygen on extra-virgin olive oil quality and yield, to define a new design of machine," 2014, Biosystems Engineering, 118 pp. 95-104.
Levy, S. F., et al., "Quantitative evolutionary dynamics using high-resolution lineage tracking," 2015, Nature, 519 pp. 181-186.
Ley, R. E., Peterson, D. A., and Gordon, J. I., "Ecological and evolutionary forces shaping microbial diversity in the human intestine," 2006, Cell, 124 pp. 837-848.
Lloyd-Price, J., Abu-Ali, G., and Huttenhower, C., "The healthy human microbiome," 2016, Genome Medicine, 8.
Locey, K. J., and Lennon, J. T., "A modeling platform for the simultaneous emergence of ecological patterns," 2017, PeerJ Preprints, 5:e1469v1463.
Locey, K. J., and Lennon, J. T., "A residence time framework for biodiversity," 2018, PeerJ Preprints, 5:e2727v2722.
Locey, K. J., Fisk, M. C., and Lennon, J. T., "Microscale insight into microbial seed banks," 2017, Frontiers in Microbiology, 7(2040).
Love, M. I., Huber, W., and Anders, S., "Moderated estimation of fold change and dispersion for RNA-seq data with DESeq2," 2014, Genome Biology, 15.
Lundberg, D. S., et al., "Defining the core *Arabidopsis thaliana* root microbiome," 2012, Nature, 488 pp. 86-90.
Macfarlane, S., and Dillon, J. F., "Microbial biofilms in the human gastrointestinal tract," 2007, Journal of Applied Microbiology, 102 pp. 1187-1196.
Magnusson, K. R., et al., "Realtionships between diet-related changes in the gut microbiome and cognitive flexibility," 2015, Neuroscience, 300 pp. 128-140.
Maleki et al., Whispering gallery mode lithium niobate microresonators for photonics applications, 2003, Proceedings of SPIE, 5104.
Martiny, J. B. H., et al., "Microbiomes in light of traits: A phylogenetic perspective," 2015, Science, 350(6261) pp. aac9323.
Mathys, S., et al., "PCR and real-time PCR primers developed for detection and identification of Bifidobacterium thermophilum in faeces," 2008, BMC Microbiology, 8 p. 179.
Mehta, S et al., Synthesis, molecular docking and biological potentials of new 2-(4-(2-chloroacetyl) piperazin-1-yl)-N-(2-(4-chlorophenyl)-4-oxoquinazolin-3(4H)-yl)acetamide derivatives. BMC Chemistry, vol. 13, No. 1, Sep. 5, 2019, publication 113, doi: 10.1186/s13065-019-0629-0.
Minekus, M., "Models of the gastrointestinal tract to study microbial interactions," 2005, Microbial Ecology in Growing Animals, 2 pp. 142-154.
Moldovan, N. I., Hibino, N., and Nakayama, K., "Principles of the Kenzan method for robotic cell spheroid-based three-dimensional bioprinting," 2017, Tissue Engineering Part B-Reviews, 23 pp. 237-244.
Molly, K., Woestyne, M. V., and Verstraete, W., "Development of a 5-step multichamber reactor as a simulation of the human intestinal microbial ecosystem," 1993, Applied Microbiology and Biotechnology, 39 pp. 254-258.
Monod, J., "La technique de culture continue Théorie et applic," 1950, Ann Inst Pasteur, 79 pp. 390-410.
Monro et al., "Sensing with Suspended-Core Optical Fibers," 2010, Opt. Fiber Technology, 16(6):343-356.
Muller-Lissner, S. A., et al., "Myths and misconceptions about chronic constipation," 2005, American Journal of Gastroenterology, 100 pp. 232-242.
Murphy, S. V., and Atala, A., "3D bioprinting of tissues and organs," 2014, Nature Biotechnology, 32 pp. 773-785.
Murray J. A., et al., "No difference between latiglutenase and placebo in reducing villous atrophy or improving symptoms in patients with symptomatic celiac disease," 2017, Gastroenterology, 152 pp. 787-798.
Niba, E. T. E., et al., "A genome-wide approach to identify the genes involved in biofilm formation in *E. coli*.," 2007, DNA Research, 14 pp. 237-246.
Novick, A., and Szilard, L., "Experiments with the chemostat on spontaneous mutations," 1950, Proceedings of the National Academy of Sciences of the United States of America, 36 pp. 708-719.
Owczarek, D., et al., "Diet and nutritional factors in inflammatory bowel diseases," 2016, World Journal of Gastroenterology, 22 pp. 895-905.
Partial Supplementary European Search Report for copending application No. 21788045.9, mailed Apr. 25, 2024.
PCT International Search Report and Written Opinion completed by the ISA/US on Feb. 26, 2022 and issued in connection with PCT/US2021/056215.
Pedron, T., et al., "A crypt-specific core microbiota resides in the mouse colon," 2012, mBio 3: e00116-12.
Pepper, J. W., and Rosenfeld, S., "The emerging medical ecology of the human gut microbiome," 2012, Trends in Ecology & Evolution, 27 pp. 381-384.
Pirt, S. J., "The maintenance energy of bacteria in growing cultures," 1965, Proceedings of the Royal Society London B Biological Sciences, 12 pp. 224-231.
Powers et al., "Propagation of a topological transition: the Rayleigh instability", 1998, Phys Fluids 10(5):1052-1057.
PubChem Record, CID 3192176 (create date: Aug. 10, 2005).
PubChem Record, CID 45953305 (create date: Jun. 22, 2010).
PubChem-SID-132887069, Modify Date: May 31, 2019 (May 31, 2019).
Reese, A. T., and Dunn, R. R., "Drivers of microbiome biodiversity: a review of general rules, feces, and ignorance," 2018, mBio, 9(4) e01294-18.
Rossi, M., et al., "Fermentation of fructooligosaccharides and inulin by bifidobacteria: a comparative study of pure and fecal cultures," 2005, Applied and Environmental Microbiology, 71 pp. 6150-6158.
Allison, S. D., "Cheaters, diffusion and nutrients constrain decomposition by microbial enzymes in spatially structured environments," 2005, Ecology Letters, 8 pp. 626-635.
Arcidacono, S., et al., "The current state and future direction of DoD gut microbiome research: a summary of the first DoD gut microbiome informational meeting," 2018, Standards in Genomic Sciences, 13 p. 5.
Arnoldini, M., Cremer, J., and Hwa, T., "Bacterial growth, flow, and mixing shape human gut microbiota density and composition," 2018, Gut Microbes, 9 pp. 559-566.
Aron-Wisnewsky, J., and Clement, K., "The gut microbiome, diet, and links to cardiometabolic and chronic disorders," 2016, Nature Reviews Nephrology, 12 pp. 169-181.
Avino et al. "Solid-phase synthesis of oligomers carrying several chromophore units linked by phosphodiester backbones" Bioorganic & Medicinal Chemistry Letters 2008. vol 18, No. 7, pp. 2306-2310; p. 2306, col. 2, para 3-4.
Bein, A., et al., "Microfluidic organ-on-a-chip models of human intestine," 2018, Cellular and Molecular Gastroenterology and Hepatology, 5(4) pp. 659-668.
Bohm, A., Kleessen, B., and Henle, T., "Effect of dry heated inulin on selected intestinal bacteria," 2006, European Food Research and Technology, 222 pp. 737-740.
Brooks, A. W., et al., "Gut microbiota diversity across ethnicities in the United States," 2018, Plos Biology 16: e2006842.

(56) References Cited

OTHER PUBLICATIONS

Bucci, V., and Xavier, J., "Towards predictive models of the human gut microbiome," 2014, Journal of Molecular Biology, 426 pp. 3907-3916.
Camilleri, M., et al., "Clinical guideline: management of gastroparesis," 2013, American Journal of Gastroenterology, 108(1) pp. 18-37.
Caporaso, J. G., et al., "Ultra-high-throughput microbial community analysis on the Illumina HiSeq and MiSeq platforms," 2012, ISME Journal, 6 pp. 1621-1624.
Chaussabel et al., "Assessing the human immune system through blood transcriptomics," 2010, BMC Biology, 8 pp. 1-14.
Cho, I., and Blaser, M., "Applications of next-generation sequencing the human microbiome: at the interface of health and disease," 2012, Nature Reviews Genetics, 13 pp. 260-270.
Colombe et al., "Single-mode optical fiber for high-power, low-loss UV transmission," 2014, Optics Express, 22(16) p. 19783.
Costello, E. K., et al., "Bacterial community variation in human body habitats across space and time," 2009, Science, 326 pp. 1694-1697.
Costello, E. K., et al., "The application of ecological theory toward an understanding of the human microbiome," 2012, Science, 336 pp. 1255-1262.
Cottingham, K. L., Lennon J. T., and Brown B. L., "Knowing when to draw the line: designing more informative ecological experiments," 2005, Frontiers in Ecology and the Environment, 3 pp. 145-152.
Cremer, J., Arnoldini, M., and Hwa, T., "Effect of water flow and chemical environment on microbiota growth and composition in the human colon," 2017, Proceedings of the National Academy of Sciences of the United States of America, 114 pp. 6438-6443.
Crump, B. C., "Microbial biogeography along an estuarine salinity gradient: combined influences of bacterial growth and residence time," 2004, Applied and Environmental Microbiology, 70 pp. 1494-1505.
D'Argenio, V., and Salvatore, F., "The role of the gut microbiome in the healthy adult status," 2015, Clinica Chimica Acta, 451 pp. 97-102.
David, L. A., et al., "Diet rapidly and reproducibly alters the human gut microbiome," 2014, Nature, 505 pp. 559-563.
Dietze, M. C., et al., "Iterative near-term ecological forecasting: Needs, opportunities, and challenges," 2018, Proceedings of the National Academy of Sciences of the United States of America, 115 pp. 1424-1432.
Donaldson, G. P., Lee S. M., and Mazmanian, S. K., "Gut biogeography of the bacterial microbiota," 2016, Nature Reviews Microbiology, 14 pp. 20-32.
Faccini de Lima et al., "Towards Digital Manufacturing of Smart Multimaterial Fibers," 2019, Nanoscale Research Letters, 14(209) pp. 1-16.
Farajikhah et al., "Thermally drawn biodegradable fibers with tailored topography for biomedical applications," 2020, Journal of Biomedical Materials Research Part B Applied Biomaterials, 109(5) pp. 733-743.
Fera, Daniela et al.: "Idenification and characterization of small molecule antagonists of pRb inactivation by viral oncoproteins", Chemistry & Biology, vol. 19, No. 4, Apr. 20, 2012 (Apr. 20, 2012), pp. 518-528, XP002690784, ISSN: 1074-5521, DOI: 10.1016/J.CHEMBIOL.2012.03.007.
Findley, K., et al., "Health Disparities and the Microbiome," 2016, Trends in Microbiology, 24 pp. 847-850.
Fischer, M., et al., "Assessment of small intestinal transit times in ulcerative colitis and Crohn's disease patients with different disease activity using video capsule endoscopy," 2017, AAPS PharmSciTech, 18 pp. 404-409.
Flynn, K., et al., "High throughput toxicology and disease modeling using MimEX GI, a Novel 3-D gastrointestinal tissue model," 2018.
Garud, N. R., et al., "Evolutionary dynamics of bacteria in the gut microbiome within and across hosts," 2017, bioRxiv Preprint doi: https://doi.org/10.1101/210955.
Goodrich, J. K., et al., "Human genetics shape the gut microbiome," 2014, Cell, 159 pp. 789-799.
Grimm, V., et al., "A standard protocol for describing individual-based and agent-based models," 2006, Ecological Modelling, 198 pp. 115-126.
Gross, B. C., "Evaluation of 3D printing and its potential impact on biotechnology and the chemical sciences," 2014, Analytical Chemistry, 86 pp. 3240-3253.
Gumennik, A. and Sen, C., "Hierarchically vascularized organoids by fiber-embedding bioprinting," 2020, Wellcome Leap Solicitation for Human Organs, Physiology, and Engineering.
Gumennik, A., et al., "Confined in-fiber solidification and structural control of silicon and silicon-germanium microparticles," 2017, Proceedings of the National Academy of Sciences of the United States of America, 114 pp. 7240-7245.
Gumennik, A., et al., "Silicon-in-silica spheres via axial thermal gradient in-fibre capillary instabilities," 2017, Nature Communications, 4 p. 2216.
Hellweger, F. L., et al., "Advancing microbial sciences by individual-based modelling," 2016, Nature Reviews Microbiology, 14 pp. 461-471.
Hidalgo, I. J., Raub, T. J., and Borchardt, R. T., "Characterization of the human-colon carcinoma cell-line (CACO-2) as a model sysem for intestinal epithelial permebility," 1989, Gastroenterology, 96 pp. 736-749.
Huttenhower, C., et al., "Structure, function and diversity of the healthy human microbiome," 2012, Human Microbiome Project, Nature, 486 pp. 207-214.
International Search Report and Written Opinion for copending Application No. PCT/US2024/033407, mailed Oct. 25, 2024.
International Search Report for PCT/US21/27746, mailed Oct. 14, 2021.
Jones, S. E., and Lennon, J. T., "A test of the subsidy-stability hypothesis: the effects of terrestrial carbon in aquatic ecosystems," 2015, Ecology, 96 pp. 1550-1560.
Kau, A. L., et al., "Human nutrition, the gut microbiome, and the immune system," 2011, Nature, 474 pp. 327-336.
Kawasaki, S., et al., "Response of the microaerophilic *Bifidobactetium* species, B. boum and B. thermophilum, to oxygen," 2006, Applied and Environmental Microbiology, 72 pp. 6854-6858.
Kelly, J. R., et al., "Breaking down the barriers: the gut microbiome, intestinal permeability and stress-related psychiatric disorders," 2015, Front Cell Neurosci, 9 p. 392.
Kim, H. J., et al., "Contributions of microbiome and mechanical deformation to intestinal bacterial overgrowth and inflammation in a human gut-on-a-chip," 2016, Proceedings of the National Academy of Sciences of the United States of America, 113:E7-E15.
Koskella, B., Hall, L. J., and Metcalf, C. J. E., "The microbiome beyond the horizon of ecological and evolutionary theory," 2017, Nature Ecology & Evolution, 1 pp. 1606-1615.
Kotz et al. "Next generation 3D printing of glass: The emergence of enabling materials," Proc. SPIE 10804, Advanced Manufacturing Technologies for Micro- and Nanosystems in Security and Defence, 1080401 (Oct. 8, 2018); doi: 10.1117/12.2323095.
Kozich, J. J., et al., "Development of a dual-index sequencing strategy and curation pipeline for analyzing amplicon sequence data on the MiSeq Illumina sequencing platform," 2013, Applied and Environmental Microbiology, 79(17) pp. 5112-5120.
Krist et al. "Catalytically Important Residues of E6AP Ubiquitin Ligase Identified Using Acid-Cleavable Photo-Cross-Linkers". Biochemistry. 2015. 54(29): pp. 4411-4414.
Roy, S. K., Akramuzzaman, S. M., and Akbar, M. S., "Persistent diarrhea: total gut transit time and its relationship with nutrient absorption and clinical response," 1991, Journal of Pediatric Gastroenterology and Nutrition, 13 pp. 409-414.
Schaaf et al., "Defining the role of the tumor vasculature in antitumor immunity and immunotherapy," 2018, Cell Death and Disease, 9(2).
Scheffner et al. "Identification of a human ubiquitin-conjugating enzyme that mediates the ES-AP-dependent ubiquitination of p53", Proc. Natl. Acad. Sci. USA. 1994. vol. 91, pp. 8797-8801.

(56) References Cited

OTHER PUBLICATIONS

Sender, R., Fuchs, S., and Milo, R., "Revised estimates for the No. of human and bacteria cells in the body," 2016, Plos Biology, pp. 1-14.
Shadman et al., "Microstructured Biodegradable Fibers for Advanced Control Delivery," 2020, Advanced Functional Materials, 30(13) pp. 1-9.
Shah, P., et al.,"A microfluidics-based in vitro model of the gastrointestinal human-microbe interface," 2016, Nature Communications, 7 p. 11535.
Shreiner, A. B., Kao, J. Y., and Young, V. B., "The gut microbiome in health and in disease," 2015, Current Opinion in Gastroenterology, 31 pp. 69-75.
Silva, J et al., "Recent Synthetic Approaches towards Small Molecule Reactivators of p53." Biomolecules, vol. 10, No. 4, Apr. 20, 2020, publication 635, doi: 10.3390/biom10040635.
Slavin, J., "Fiber and prebiotics: Mechanisms and health benefits," 2013, Nutrients, 5 pp. 1417-1435.
Smith, D. C., and Azam, F., "A simple, economical method for measuring bacterial protein synthesis rates in seawater using 3H-leucine," 1992, Marine Microbial Food Webs, 6 pp. 107-114.
Smith, H. L., and Waltman, P., "The Theory of the Chemostat: Dynamics of Microbial Competition," 1995, Cambridge University Press, New York.
Song et al., "Vascular Tissue Engineering: Progress, Challenges, and Clinical Promise," 2018, Cell Stem Cell, 22(3) pp. 340-354.
STN registry compound RN#1048824-05-0 (Entry date Sep. 12, 2008).
STN Registry Record, RN 1089795-11-8 (entered date: Dec. 25, 2008).
STN Registry Record, RN 1089813-69-3 (entered date: Dec. 25, 2008).
STN Registry Record, RN 2094864-00-1 (entered date: May 3, 2017).
STN Registry Record, RN 648859-89-6 (entered date: Feb. 11, 2004).
Tamayo, Nuria A. et al.: "Fused Piperidines as a Novel Class of Potent and Orally Available Transient Receptor Potential Melastatin Type 8 (TRPM8) Antagonists", Journal of Medicinal Chemistry, vol. 55, No. 4, Feb. 23, 2012 (Feb. 23, 2012), pp. 1593-1611, XP055812154, US, ISSN: 0022-2623, DOI: 10.1021/jm2013634.
Tan, et al., Cutaneous B-human papillomavirus E6 proteins bind Mastermind-like coactivators and repress Notch signaling, Proceedings of the National Academy of Sciences of the United States of America, 109(23), E1473-E1480, SE1473/1-SE1473/2 ( 2012) (Year: 2012).
Tanner, S. A., et al., "Bifidobacterium thermophilum RBL67 impacts on growth and virulence gene expression of *Salmonella enterica* subsp enterica serovar Typhimurium," 2017, BMC Microbiology, 16 p. 46.
Tropini, C., et al., "The gut microbiome: connecting spatial organization to function," 2017, Cell Host & Microbe, 21 pp. 433-442.
Turnbaugh, P. J., et al., "A core gut microbiome in obese and lean twins," 2009, Nature, 457 pp. 480-487.
Van der Elst et al., "3D Printing in Fiber-Device Technology," 2021 , Advanced Fiber Materials.
Verdu, E. F., Galipeau, H. J., and Jabri, B., "Novel players in coeliac disease pathogenesis: role of the gut microbiota," 2015, Nature Reviews Gastroenterology & Hepatology, 12 pp. 497-506.
Verhoeckx, K., et al., editors. "The Impact of Food Bioactives on Health: in vitro and ex vivo models," 2015, Cham (CH): Springer.
Vieira et al., "Degradation and viscoelastic properties of PLA-PCL, PGA-PCL, PDO and PGA fibres," 2010, Materials Science Forum, 636-637 pp. 825-832.
Waldron, D., "In transit," 2015, Nature Reviews Microbiology, 13 pp. 659-659.
Walter, J., and Ley, R. E., "The human gut microbiome: ecology and recent evolutionary changes," 2011, Annual Review of Microbiology, 65 pp. 411-429.
Wei et al., "Optoelectronic Fibers via Selective Amplification of In-Fiber Capillary Instabilities," 2017, Advanced Materials, 29(1).
Williams et al., "Etch rates for micromachining processing—Part II," 2003, Journal of Microelectromechanical Systems, 12(6) pp. 761-778.
Xiao, L., et al., "A catalog of the mouse gut metagenome," 2015, Nature Biotechnology, 33 pp. 1103-1108.
Xu, Z., and Knight, R., "Dietary effects on human gut microbiome diversity," 2015, British Journal of Nutrition, 113:S1-S5.
Zanon, Patrick R A et al.: "Isotopically Labeled Desthiobiotin Azide (isoDTB) Tags Enable Global Profiling of the Bacterial Cysteinome", Angewandte Chemie, vol. 132, No. 7, Nov. 29, 2019 (Nov. 29, 2019),—Jan. 7, 2020 (Jan. 7, 2020), pp. 2851-2858, XP071382657, Wiley—VCH VERLAG GMBH & Co. Kgaa, Germany, ISSN: 0044-8249, DOI: 10.1002/ANGE.201912075.
Zhao, S., et al., "Adaptive evolution within the gut microbiome of individual people," 2017, bioRxiv Preprint doi: https://doi.org/10.1101/208009.
Zhong et "Nanophotonic rare-earth quantum memory with optically controlled retrieval," 2017, Science, 357 pp. 1392-1395.
Zhu, C. Z., et al., "Electrochemical sensors and biosensors based on nanomaterials and nanostructures," 2015, Analytical Chemistry, 87 pp. 230-249.

* cited by examiner

Compound 1

Compound 2

Compound 3

Compound 4

Compound 7

Compound 9

Compound 15

1-1 1-2 1-3 1-4 1-5 1-6 1-7 1-8 1-9 1-10 cmp 29

2-1 2-2 2-3

2-4 2-5

3-1 3-2

3-3 cmp 31

5-1 5-2 5-3 5-4 5-5 6 5-6 1-3 5-7 cmp 33

5-6

6-1

6-2 cmp 34

1-8

7-1

7-2

7-2 cmp 35

2-5

8-1

8-2

8-3

8-4 ccmp 36

1-8

9-1

9-2

9-3 cmp 37

10-1 + 10-2 → 10-3

1-8 → 10-4 → 10-5 → cmp 38

1-9 1-10

1-10 cmp 39

1-10 cmp 40

1-10 cmp 41

1-10 cmp 42

1-8

+

9-1

15-1

15-2 cmp 43

9-1

16-1

16-2 cmp 44

9-1

17-1

17-2 cmp 45

9-1

19-1

19-2 cmp 47

SMALL MOLECULE ANTIVIRAL DRUG TREATMENT FOR HUMAN PAPILLOMAVIRUS INFECTIONS

CROSS-REFERENCE TO RELATED APPLICATIONS

This application is a continuation of U.S. application Ser. No. 18/740,140, filed on Jun. 11, 2024, which claims the benefit under 35 USC § 119(e) of U.S. Provisional Patent Application No. 63/507,895 filed on Jun. 13, 2023, the disclosure of which is expressly incorporated herein.

FEDERALLY SPONSORED RESEARCH AND DEVELOPMENT

This invention was made with government support under CA268137 awarded by National Institutes of Health. The Government has certain rights in the invention.

BACKGROUND

Human papillomavirus (HPV) is an exceedingly common infection. While most infections are benign, standard destructive remedies are painful and have potential complications and co-morbidities. Moreover, persistent infections with specific HPV types can evolve into invasive and metastatic cancers. These malignancies progress slowly over several years from benign to pre-malignant to invasive lesions, so there is a suitable interval for antiviral treatment.

HPV type 16 (HPV16) is the prototype of "high-risk" HPV for neoplastic transformation and accounts for about 50% of all cervical cancers across the world and is also present in the majority of anal, vulvar, and vaginal pre-cancers (dysplasias) and cancers. Globally, 600,000 cases of cervical cancer are diagnosed each year, from which an estimated 380,000 women die annually. In the United States about 12,000 cases for cervical cancer caused by HPV infection are newly diagnosed annually. It is predicted that 44 million cases of cervical cancer will arise worldwide over the next 50 years, which would be reduced by only 15% with robust vaccination programs (K. T. Simms et al Lancet Oncol. 2019; 20(3):394-407). A subset of vulvar, vaginal and penile cancers and the majority of anal squamous cell cancers are caused by HPV infection.

It has been recently found that many oropharyngeal cancers (OPC) are caused by HPV and this malignancy now exceeds the incidence of cervical cancers in the USA (MMWR Aug. 23, 2019, Vol 68 p 724). HPV16 can be detected in oral swabs but clinical identification of precursor lesions is not reliable and surgical field approaches carry major morbidity in the oropharynx. HPV associated OPC develop over one or more decades and are largely asymptomatic until patients have advanced tumors. Destructive surgical remedies, radiation, and chemotherapy are routinely used, carry high morbidity, and are a significant financial burden.

While the existing HPV capsid is highly effective as a prophylactic vaccine, it is expensive and has not had sufficient uptake to achieve herd immunity in the USA. More importantly, this vaccine is not therapeutic for women and men with existing HPV infection, including those who have progressed to pre-malignant or malignant disease. This vaccine does not change the clinical course after virus infection has been established.

Studies have suggested HPV E6 protein is essential for stable viral genome replication and epithelial cell transformation. E6 binds to the ubiquitin ligase E6AP (UBE3A), but will not bind to p53 in the absence of E6AP. E6AP is the founding member of the HECT domain ubiquitin ligases and transfers ubiquitin onto the tumor suppressor protein p53, resulting in its destruction by the proteasome. A subsequent conformational change in E6AP-bound E6 exposes a large p53 interaction surface to generate the E6•E6AP•p53 trimeric complex. The region of E6AP that complexes with HPV E6 contains an HPV E6 binding motif with the consensus sequence LxxLL, where L is leucine and x any amino acid that folds within an α-helix.

Travé and co-workers solved the trimeric crystal structure of HPV16 E6 in complex with peptides containing the LxxLL E6 binding motif and the core domain of p53. The LxxLL motif adopts an α-helical structure that docks into a well-defined large pocket. Replacement of any of the leucines within the helix disrupts binding to E6. This E6AP binding pocket on E6 acts as a 'hot spot' for association with cellular proteins encoding the LxxLL motif. The compounds disclosed herein covalently bind within this pocket, or 'hot spot' in HPV E6, such as HPV16 E6, and irreversibly block its interactions with E6AP and will interfere with other binding partners that encode the HPV E6 binding motif.

High-risk HPV E7 inhibits the Rb tumor suppressor pathway, causing continuous stimulation of cell division and induction of the p53 pathway. Both HPV16 E6 and E7 are expressed in HPV induced tumors. HPV E6 counteracts p53 activation by forming a complex with E6AP as well as binding to its other cellular partners through the same binding pocket. Studies have shown that inhibiting E6 restores wild-type p53 protein levels and function (E. Cukuroglu, et al., Prog. Biophys. Mol. Biol. 116, 165-173 (2014)). Abrogation of HPV E6 activity leads to growth arrest or cell death of HPV cervical cancer cell lines.

There is great medical need for treatment of HPV infections. Our strategy was to use structure-based drug design to select drug-like molecules that specifically and covalently bind to E6 and disrupt its protein-protein interactions (PPI). Applicants anticipate that administration of medication that blocks HPV E6 functions including one topically applied to the cervix, anus, penis, vulva, vagina or oropharynx will effectively eliminate HPV DNA and serve to treat pre-malignant infected tissues and treat HPV induced cancers. In one embodiment a medication is provided that blocks HPV E6 functions and is topically applied to the cervix, anus, penis, vulva, vagina or oropharynx to treat pre-malignant infected tissues. In one embodiment a systemically delivered E6 binding compound is used to treat HPV induced cancers as well as pre-malignant HPV infections.

SUMMARY OF THE INVENTION

In one embodiment, the present disclosure is directed to an HPV E6 binding compound having the structure of Formula I:

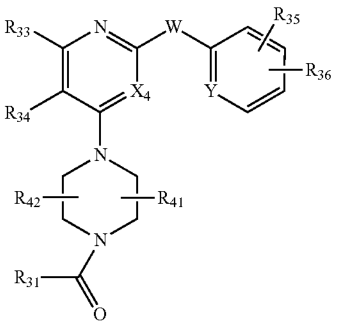

wherein Y is C or N;

$X_4$ is N or C;

W is —$(CH_2)_n$— or —CH═$CR_{32}$—;

$R_{32}$ is H or —$(CH_2)_n$— n is an integer selected from the range of 0-4;

$R_{31}$ is selected from the group consisting of —CH═$CH_2$, —$CR_{51}$═$CH_2$, —CH═$CHCH_2N(CH_3)_2$, —CH═$CHCH_3$, $CH_2$(halo) and $CH_3$ wherein $R_{51}$ is H or halo, optionally where $R_{51}$ is H or F, optionally wherein $R_{31}$ is —CH═$CH_2$;

$R_{33}$ and $R_{34}$ together with the atoms to which they are attached form a ring structure selected from the group consisting of

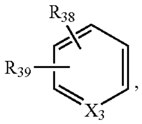 , 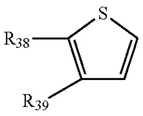 , and 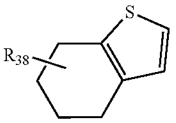 ;

$X_3$ is C or N;

$R_{38}$ is selected from the group consisting of H, —$OCH_3$, —$OCF_3$, —$OCH_2CH_3$, and —$OCH_2CH_2OCH_3$;

$R_{39}$ is H, halo or $CH_3$;

$R_{35}$ is selected from the group consisting of H and halo:

$R_{36}$ is selected from the group consisting of H, halo, —$OCH_3$, —$OCH_2CH_3$, —$OCH_2CH_2OCH_3$—$CONHCH_3$ and O(CH2)$_n$—N-pyrrolidine, or $R_{35}$ and $R_{36}$ are together with the atoms to which they are attached form a ring structure of

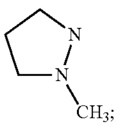

$R_{41}$ is H or $C_1$-$C_4$ alkyl;

$R_{42}$ is H, —CN, $C_1$-$C_4$ alkyl, OH, $CO_2H$, esters, amides, or $R_{41}$ and $R_{42}$ together with the atoms to which they are attached form a 4-6 membered ring (as part of a bridged bicyclic ring); with the proviso that when $R_{41}$ and $R_{42}$ are both H, either $R_{36}$ is —$OCH_2CH_3$, or $R_{38}$ is other than H.

In one embodiment an HPV E6 binding compound is provided having the general structure of

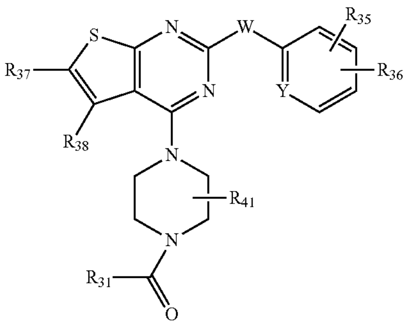

wherein

Y is C or N;

W is —$(CH_2)_n$—;

n is an integer selected from the range of 2-4;

$R_{31}$ is selected from the group consisting of —CH═$CH_2$, —$CR_{51}$═$CH_2$, —CH═$CHCH_2N(CH_3)_2$, —CH═$CHCH_3$, $CH_2$(halo) and $CH_3$ wherein $R_{51}$ is H or halo, optionally where $R_{51}$ is H or F, optionally wherein $R_{31}$ is —CH═$CH_2$;

$R_{37}$ and $R_{38}$ are each H or $R_{37}$ and $R_{38}$ together with the atoms to which they are attached form a ring structure of

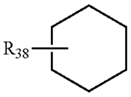 ;

$R_{38}$ is H, halo or $CH_3$;

$R_{35}$ is halo:

$R_{36}$ is selected from the group consisting of halo, —$OCH_3$, and —$OCH_2CH_3$; and $R_{41}$ is H or $C_1$-$C_4$ alkyl.

In one embodiment an HPV E6 binding compound is provided having the general structure of

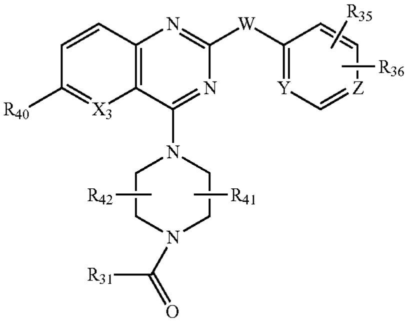

wherein

Y and Z are independently C or N;

$X_3$ is C or N;

W is —$(CH_2)_n$ or —CH═CH—;

n is an integer selected from the range of 0-4;

$R_{31}$ is selected from the group consisting of —CH═$CH_2$, —$CR_{51}$═$CH_2$, —CH═$CHCH_2N(CH_3)_2$, —CH═$CHCH_3$, $CH_2$(halo) and $CH_3$ wherein $R_{51}$ is H or halo, optionally where $R_{51}$ is H or F, optionally wherein $R_{31}$ is —CH═$CHCH_2N(CH_3)_2$;

$R_{35}$ is selected from the group consisting of H and halo:

$R_{36}$ is selected from the group consisting of H, halo, —$OCH_3$, —$OCH_2CH_3$, —$OCH_2CH_2OCH_3$ and $CONHCH_3$;

$R_{40}$ is selected from the group consisting of H, —$OCH_3$, —$OCH_2CH_3$, and —$OCH_2CH_2OCH_3$;

$R_{41}$ is H or $C_1$-$C_4$ alkyl;

$R_{42}$ is H, —CN, $C_1$-$C_4$ alkyl, OH, $CO_2H$, esters, amides, or $R_{41}$ and $R_{42}$ together with the atoms to which they are attached form a 4-6 membered ring (as part of a bridged bicyclic ring); with the proviso that when $R_{41}$ and $R_{42}$ are both H, either $R_{36}$ is —$OCH_2CH_3$, or $R_{38}$ is other than H.

In accordance with one embodiment any of the HPV E6 binding compounds disclosed herein can be used to treat an HPV infection, including the treatment of non-malignant, pre-malignant and HPV induced tumors. In one embodiment the HPV E6 binding compounds disclosed herein are used to inhibit E6 binding to ubiquitin ligase E6AP. In one embodiment the HPV E6 binding compounds disclosed herein are used to inhibit E6 activity and restore wild-type p53 protein levels and function.

Additional embodiments, features, and advantages of the disclosure will be apparent from the following detailed description and through practice of the disclosure. The compounds of the present disclosure can be described as embodiments in any of the following enumerated embodiments. It will be understood that any of the embodiments described herein can be used in connection with any other embodiments described herein to the extent that the embodiments do not contradict one another.

BRIEF DESCRIPTION OF DRAWINGS

FIGS. 26A and 26B: HPV negative (RPE-1) and HPV positive cervical cancer cell line (SiHa) were incubated with increasing concentrations of 4 or 15 or DMSO (D1, D2; 0.1% v/v) for 24 hrs. Cells were treated with Etoposide (ETO, 25 μM) as a positive control for p53 induction. Cells were lysed, proteins separated by SDS-PAGE and p53, GAPDH protein levels were determined using Immunoblot. Band intensity was measured by densitometry and expressed as fold change over DMSO. * indicates a statistical significance of $P<0.05$. Data expressed as S.E.M, n≥3.

FIG. 27C, CaSki; FIG. 27A) and oral cancer cell lines (UM-SCC-47; FIG. 27B, UM-SCC-104; FIG. 27D) or HPV negative (RPE-1; FIG. 27E) were incubated with increasing concentrations of 1, 3, or 15 for 24 hours. Viable cells were quantified with calcein-AM cell viability assay. Data expressed as S.E.M.

DETAILED DESCRIPTION OF THE INVENTION

Definitions

Figure 1A:
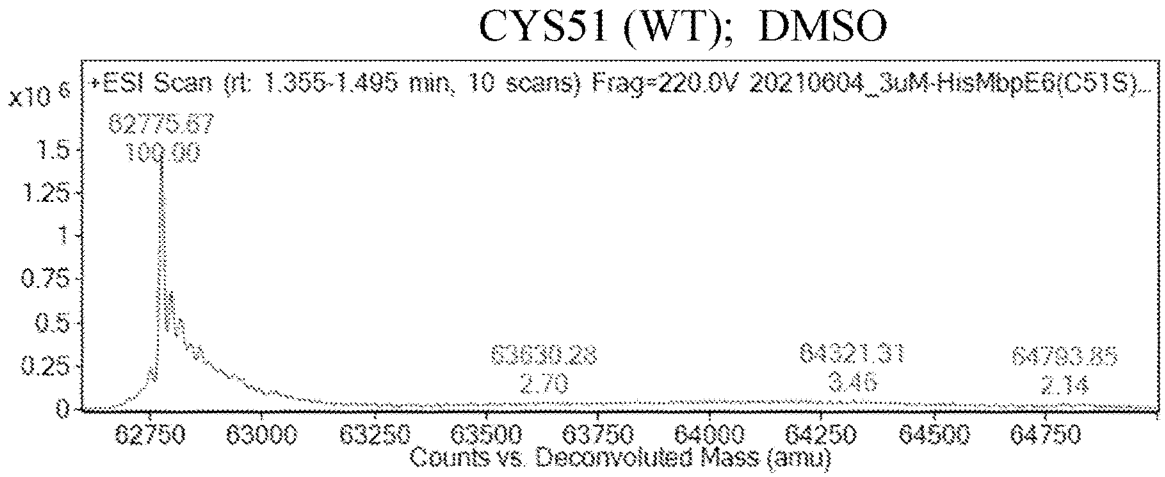
FIGS. 1A & 1B Whole-protein mass spectrometry of MBP (maltose binding protein) fusion protein to wild-type (WT) HPV-16 E6 (FIG. 1A) or HPV-16 E6 with cysteine 51 mutated to serine (C51S, FIG. 1B) incubated in the presence of DMSO (dimethyl sulfoxide) at 4° C. for 24 h.
Figure 1B:
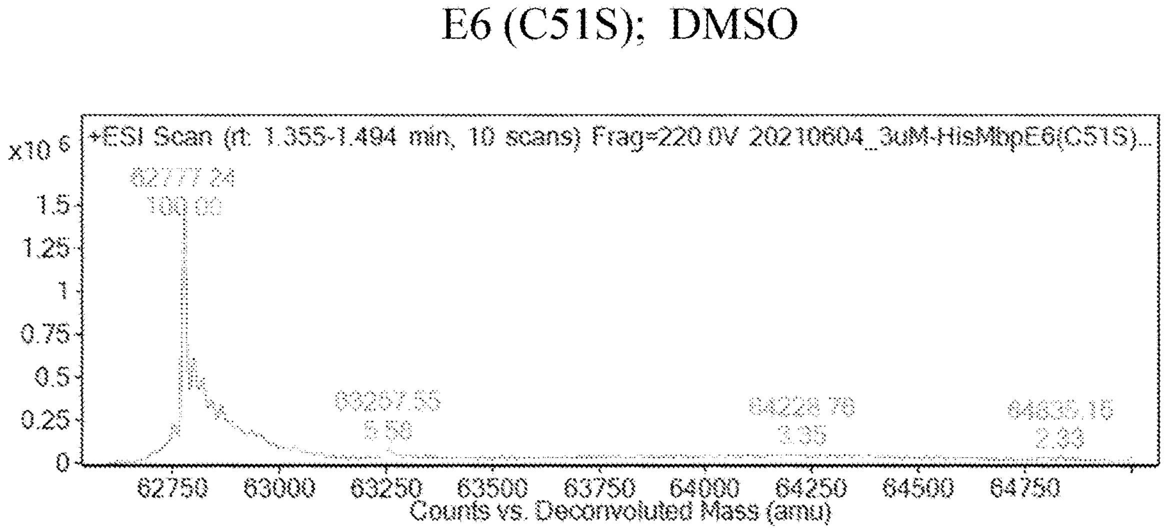
Figure 2A:
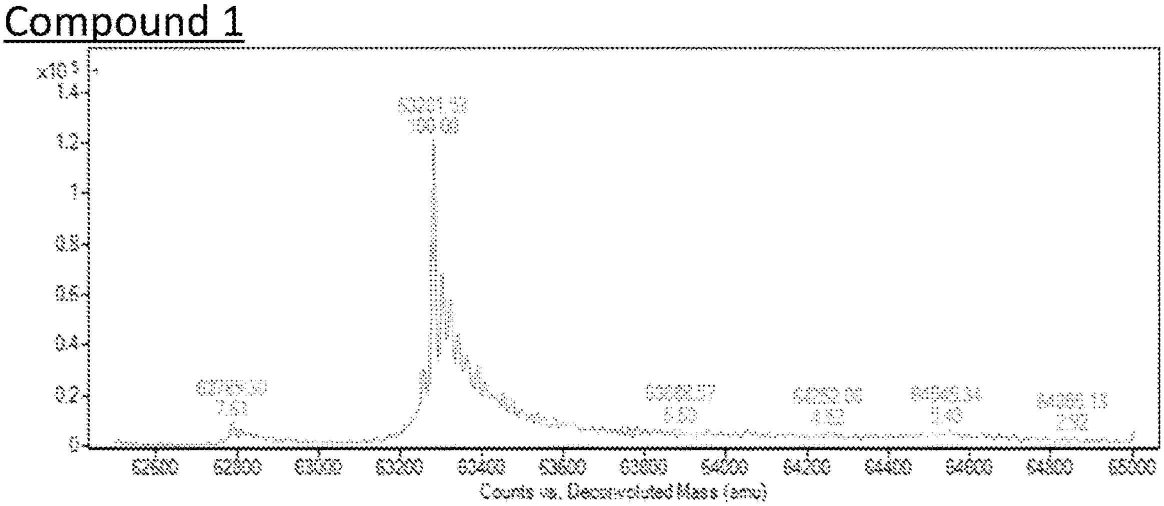
FIGS. 2A & 2B Whole-protein mass spectrometry of MBP (maltose binding protein) fusion protein to wild-type (WT) HPV-16 E6 (FIG. 2A) or HPV-16 E6 with cysteine 51 mutated to serine (C51S, FIG. 2B) incubated in the presence of 10 (top) or 100 μM (bottom) Compound 1 at 4° C. for 24 h.
Figure 2B:
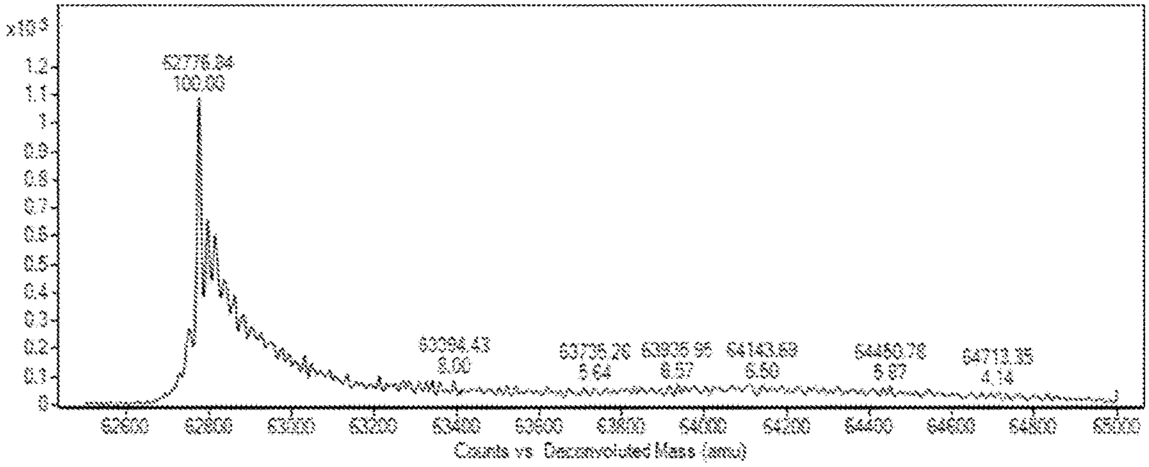
Figure 3A:
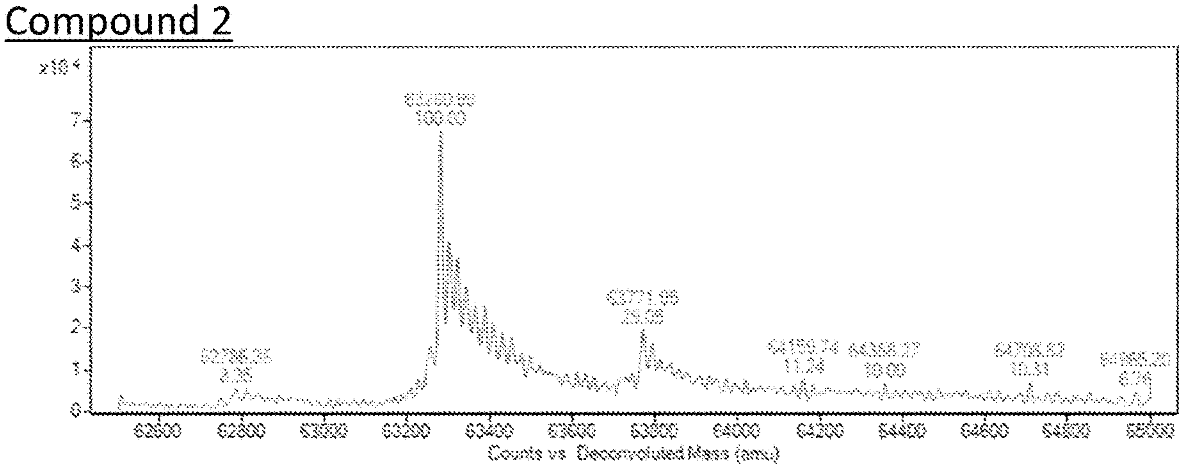
FIGS. 3A & 3B Whole-protein mass spectrometry of MBP (maltose binding protein) fusion protein to wild-type (WT) HPV-16 E6 (FIG. 3A) or HPV-16 E6 with cysteine 51 mutated to serine (C51S, FIG. 3B) incubated in the presence of 100 μM Compound 2 at 4° C. for 24 h.
Figure 3B:
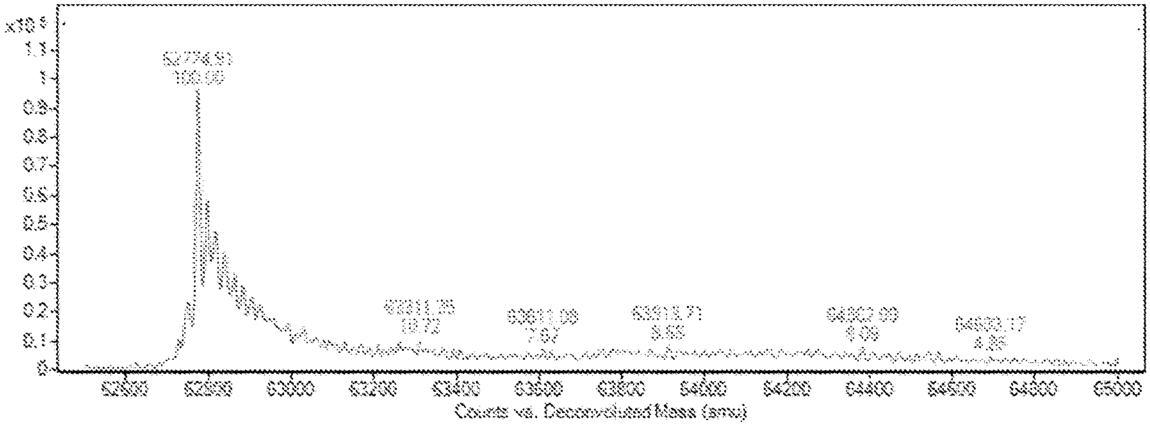
Figure 4A:
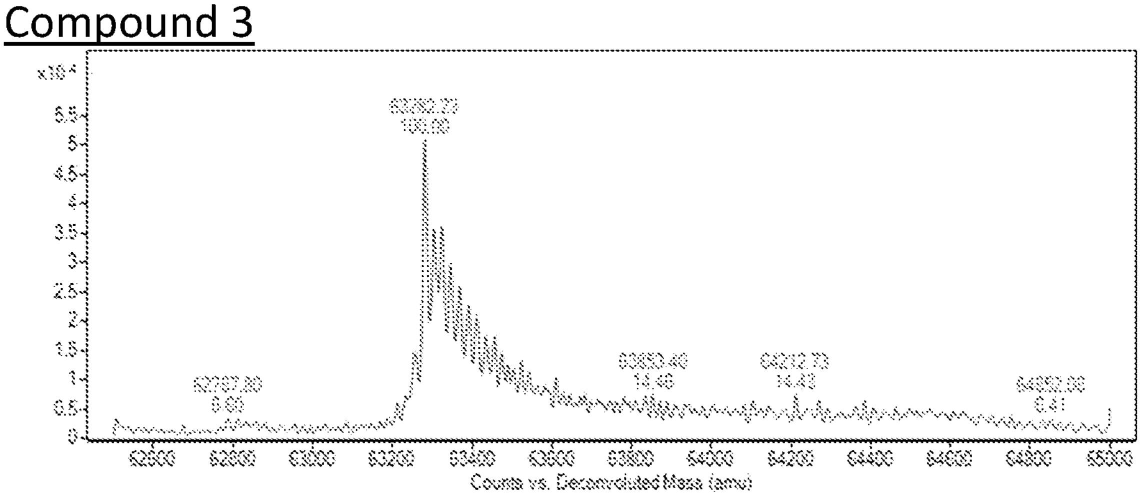
FIGS. 4A & 4B Whole-protein mass spectrometry of MBP (maltose binding protein) fusion protein to wild-type (WT) HPV-16 E6 (FIG. 4A) or HPV-16 E6 with cysteine 51 mutated to serine (C51S, bottom) incubated in the presence of 10 (top) or 100 μM (FIG. 4B) Compound 3 at 4° C. for 24 h.
Figure 4B:
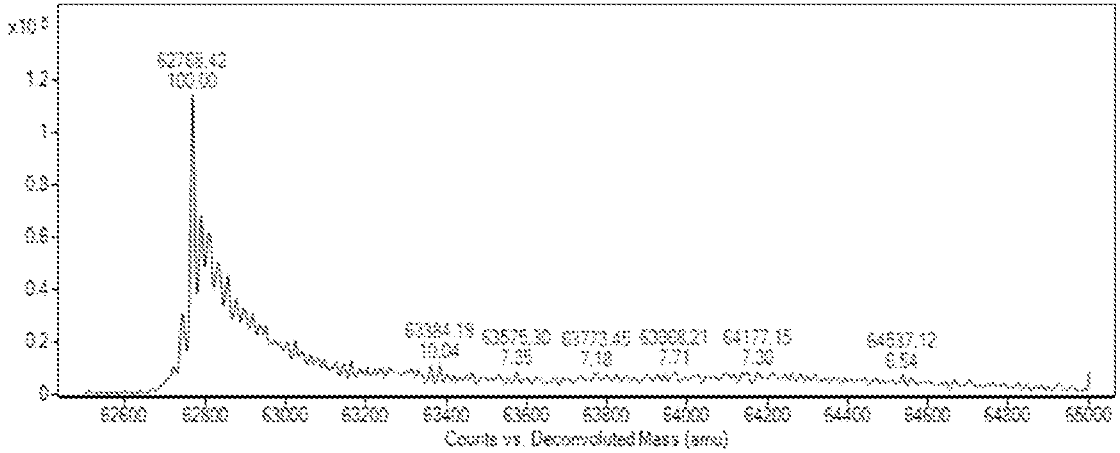
Figure 5A:
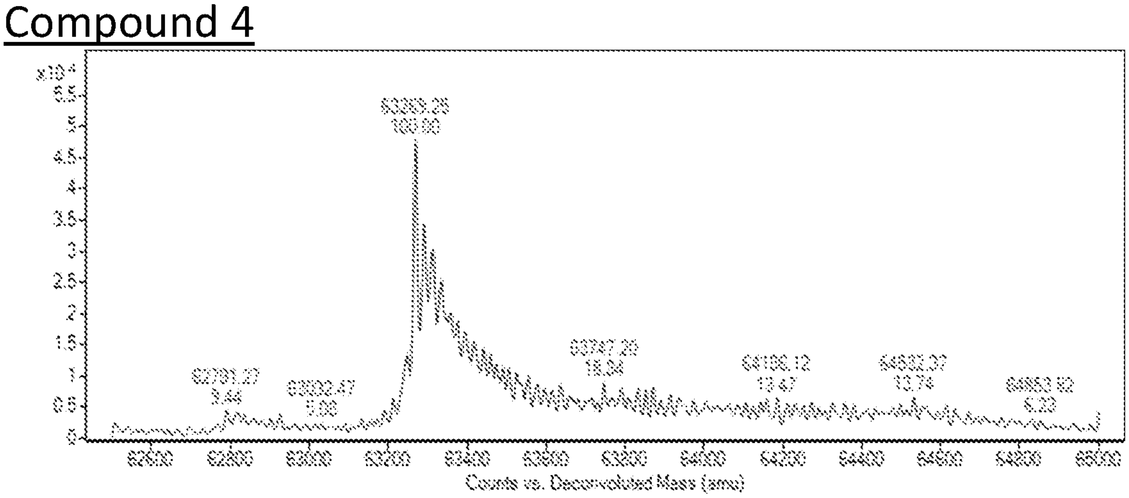
FIGS. 5A & 5B Whole-protein mass spectrometry of MBP (maltose binding protein) fusion protein to wild-type (WT) HPV-16 E6 (FIG. 5A) or HPV-16 E6 with cysteine 51 mutated to serine (C51S, FIG. 5B) incubated in the presence of 100 μM Compound 4 at 4° C. for 24 h.
Figure 5B:
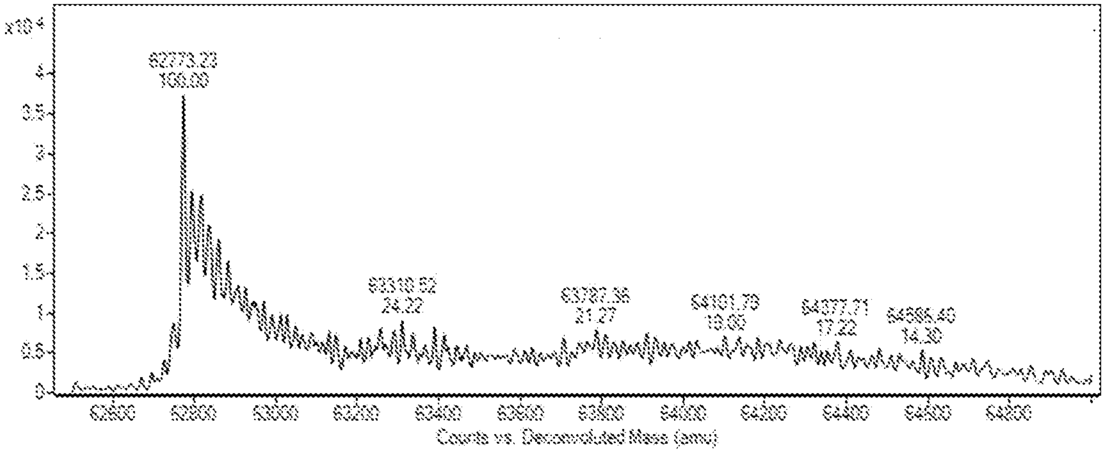
Figure 6A:
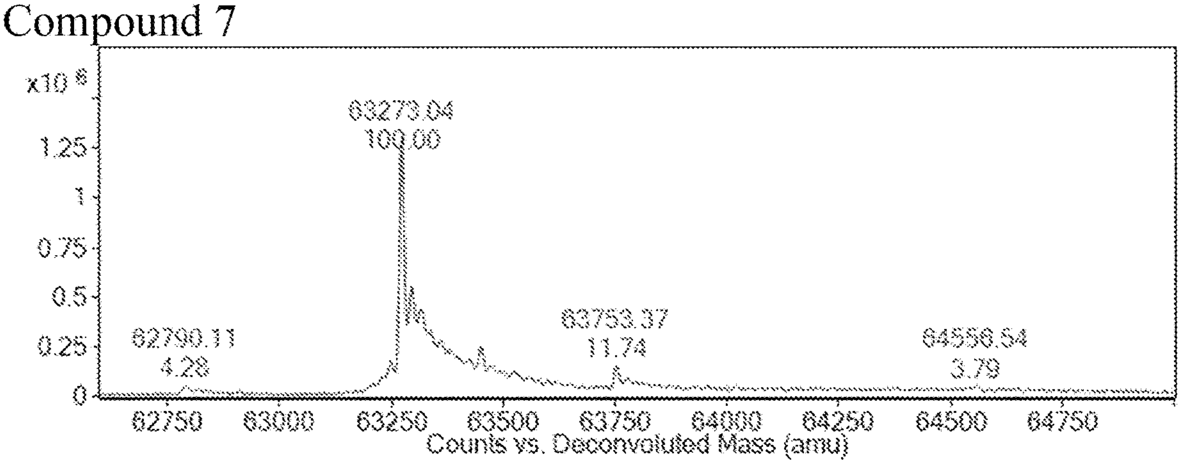
FIGS. 6A & 6B Whole-protein mass spectrometry of MBP (maltose binding protein) fusion protein to wild-type (WT) HPV-16 E6 (FIG. 6A) or HPV-16 E6 with cysteine 51 mutated to serine (C51S, FIG. 6B) incubated in the presence of 100 μM Compound 7 at 4° C. for 24 h.
Figure 6B:
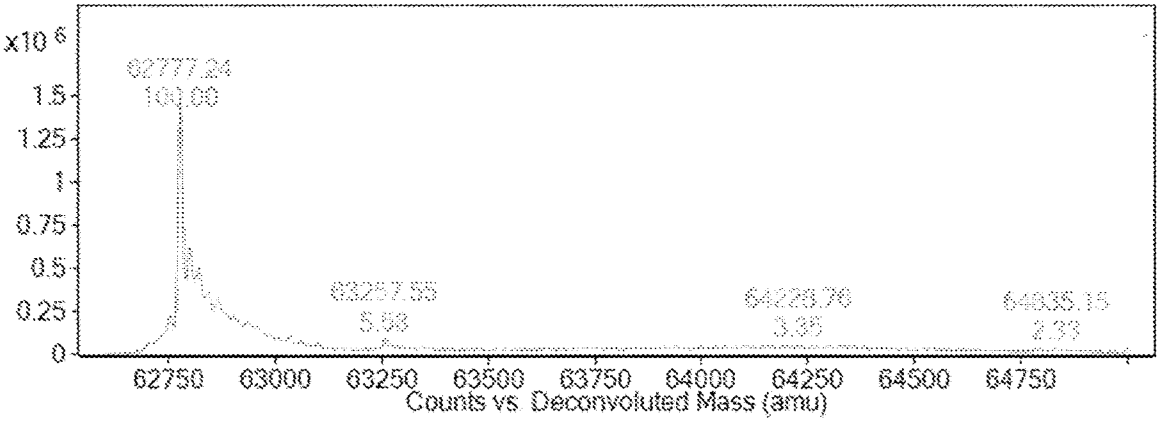
Figure 7A:
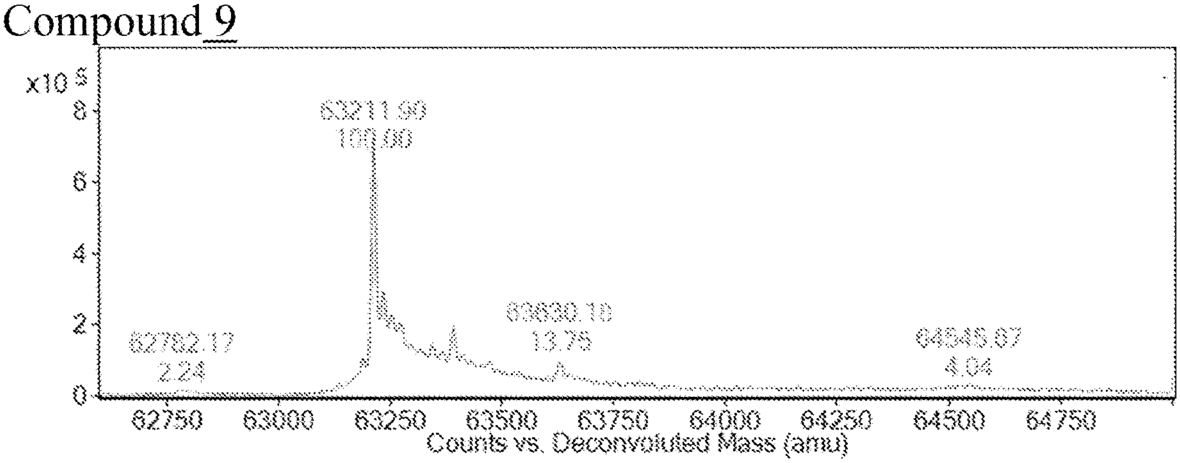
FIGS. 7A & 7B Whole-protein mass spectrometry of MBP (maltose binding protein) fusion protein to wild-type (WT) HPV-16 E6 (FIG. 7A) or HPV-16 E6 with cysteine 51 mutated to serine (C51S, FIG. 7B) incubated in the presence of 100 μM Compound 9 at 4° C. for 24 h.
Figure 7B:
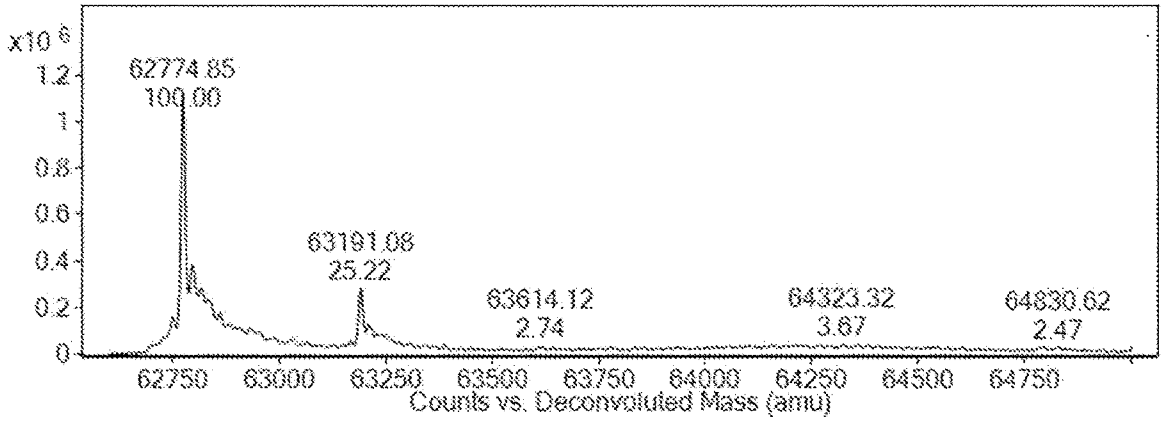
Figure 8A:
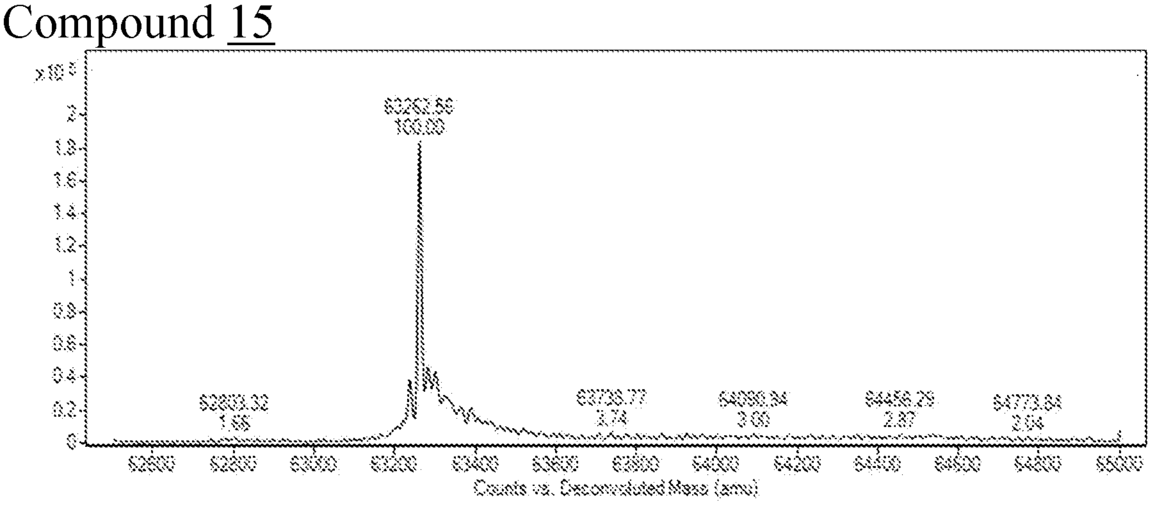
FIGS. 8A & 8B Whole-protein mass spectrometry of MBP (maltose binding protein) fusion protein to wild-type (WT) HPV-16 E6 (FIG. 8A) or HPV-16 E6 with cysteine 51 mutated to serine (C51S, FIG. 8B) incubated in the presence of 10 μM (FIG. 8A) or 100 μM (FIG. 8B) Compound 15 at 4° C. for 24 h.
Figure 8B:
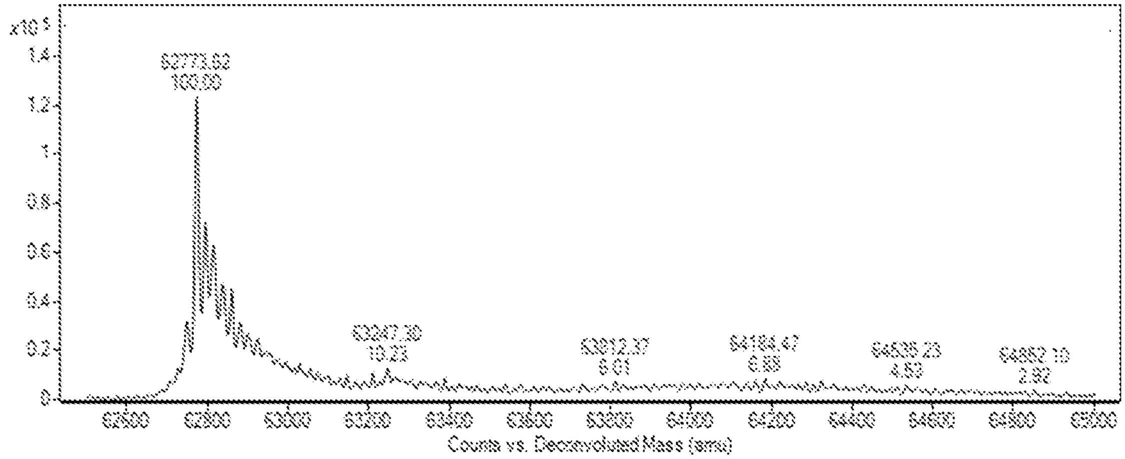

In describing and claiming the invention, the following terminology will be used in accordance with the definitions set forth below.

As used herein, the terms "including," "containing," and "comprising" are used in their open, non-limiting sense.

The term "about" as used herein means greater or lesser than the value or range of values stated by 10 percent but is not intended to limit any value or range of values to only this broader definition. Each value or range of values preceded by the term "about" is also intended to encompass the embodiment of the stated absolute value or range of values.

As used herein, the term "purified" and like terms relate to the isolation of a molecule or compound in a form that is substantially free of contaminants normally associated with the molecule or compound in a native or natural environment. As used herein, the term "purified" does not require absolute purity; rather, it is intended as a relative definition.

As used herein, the term "treating" includes alleviation of symptoms associated with a specific disorder or condition and/or preventing or eliminating said symptoms.

As used herein, an "effective" amount or a "therapeutically effective amount" of a drug refers to a nontoxic but enough of the drug to provide the desired effect. The amount that is "effective" will vary from subject to subject or even within a subject overtime, depending on the age and general condition of the individual, mode of administration, and the like. Thus, it is not always possible to specify an exact "effective amount." However, an appropriate "effective" amount in any individual case may be determined by one of ordinary skill in the art using routine experimentation.

As used herein, the term "patient" without further designation is intended to encompass any human, and includes individuals not under the direct care of a physician.

The term "carrier" means a compound, composition, substance, or structure that, when in combination with a compound or composition, aids or facilitates preparation, storage, administration, delivery, effectiveness, selectivity, or any other feature of the compound or composition for its intended use or purpose. For example, a carrier can be selected to minimize any degradation of the active ingredient and to minimize any adverse side effects in the subject.

The term "inhibit" refers to a decrease in an activity, response, condition, disease, or other biological parameter. This can include but is not limited to the complete ablation of the activity, response, condition, or disease. This may also include, for example, a 10% reduction in the activity, response, condition, or disease as compared to the native or control level. Thus, the reduction can be a 10, 20, 30, 40, 50, 60, 70, 80, 90, 100%, or any amount of reduction in between, as compared to native or control levels.

As used herein, the term "alkyl" includes a chain of carbon atoms, which is optionally branched and contains from 1 to 20 carbon atoms. It is to be further understood that in certain embodiments, alkyl may be advantageously of limited length, including $C_1$-$C_{12}$, $C_1$-$C_{10}$, $C_1$-$C_9$, $C_1$-$C_8$, $C_1$-$C_7$, $C_1$-$C_6$, and $C_1$-$C_4$, Illustratively, such particularly limited length alkyl groups, including $C_1$-$C_8$, $C_1$-$C_7$, $C_1$-$C_6$, and $C_1$-$C_4$, and the like may be referred to as "lower alkyl." Illustrative alkyl groups include, but are not limited to, methyl, ethyl, n-propyl, isopropyl, n-butyl, isobutyl, sec-butyl, tert-butyl, pentyl, 2-pentyl, 3-pentyl, neopentyl, hexyl, heptyl, octyl, and the like. Alkyl may be substituted or unsubstituted. Typical substituent groups include cycloalkyl, aryl, heteroalicyclic, alkoxy, halo, carbonyl, oxo, (=O), C-carboxy, O-carboxy, nitro, and amino, or as described in the various embodiments provided herein. It will be understood that "alkyl" may be combined with other groups, such as those provided above, to form a functionalized alkyl. By way of example, the combination of an "alkyl" group, as described herein, with an "aryl" group may be referred to as an "alkylaryl" group.

As used herein, the term "alkenyl" includes a chain of carbon atoms, which is optionally branched, and contains from 2 to 20 carbon atoms, and also includes at least one carbon-carbon double bond (i.e., C=C). It will be understood that in certain embodiments, alkenyl may be advantageously of limited length, including $C_2$-$C_{12}$, $C_2$-$C_9$, $C_2$-$C_8$, $C_2$-$C_7$, $C_2$-$C_6$, and $C_2$-$C_4$. Alkenyl may be unsubstituted or substituted as described for alkyl or as described in the various embodiments provided herein. The at least one carbon-carbon double bond may be internal or terminal. Illustrative alkenyl groups include, but are not limited to, ethenyl, 1-propenyl, 2-propenyl, 1-, 2-, or 3-butenyl, and the like.

As used herein, the term "alkynyl" includes a chain of carbon atoms, which is optionally branched, and contains from 2 to 20 carbon atoms, and also includes at least one carbon-carbon triple bond (i.e., C≡C). It will be understood that in certain embodiments, alkynyl may each be advantageously of limited length, including $C_2$-$C_{12}$, $C_2$-$C_9$, $C_2$-$C_8$, $C_2$-$C_7$, $C_2$-$C_6$, and $C_2$-$C_4$. Alkynyl may be unsubstituted or substituted as described for alkyl or as described in the various embodiments provided herein. The at least one carbon-carbon triple bond may be internal or terminal. Illustrative alkynyl groups include, but are not limited to, ethynyl, 1-propynyl, 2-propynyl, 1-, 2-, or 3-butynyl, and the like.

As used herein, the term "aryl" refers to an all-carbon monocyclic or fused-ring polycyclic groups of 6 to 12 carbon atoms having a completely conjugated pi-electron system. It will be understood that in certain embodiments, aryl may be advantageously of limited size such as $C_6$-$C_{10}$ aryl. Illustrative aryl groups include, but are not limited to, phenyl, naphthylenyl and anthracenyl. The aryl group may be unsubstituted or substituted as described for alkyl or as described in the various embodiments provided herein.

As used herein, the term "cycloalkyl" refers to a 3 to 15 member all-carbon monocyclic ring, including an all-carbon 5-member/6-member or 6-member/6-member fused bicyclic ring, or a multicyclic fused ring (a "fused" ring system means that each ring in the system shares an adjacent pair of carbon atoms with each other ring in the system) group, or a carbocyclic ring that is fused to another group such as a heterocyclic, such as ring 5- or 6-membered cycloalkyl fused to a 5- to 7-membered heterocyclic ring, where one or more of the rings may contain one or more double bonds but the cycloalkyl does not contain a completely conjugated pi-electron system. It will be understood that in certain embodiments, cycloalkyl may be advantageously of limited size such as $C_3$-$C_{13}$, $C_3$-$C_9$, $C_3$-$C_6$ and $C_4$-$C_6$. Cycloalkyl may be unsubstituted or substituted as described for alkyl or as described in the various embodiments provided herein. Illustrative cycloalkyl groups include, but are not limited to, cyclopropyl, cyclobutyl, cyclopentyl, cyclopentenyl, cyclopentadienyl, cyclohexyl, cyclohexenyl, cycloheptyl, and the like. Illustrative examples of cycloalkyl groups shown in graphical representations include the following entities, in the form of properly bonded moieties:

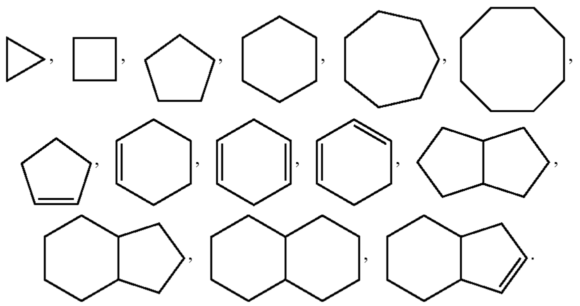

As used herein, the term "heterocycloalkyl" or "heterocyclic" defines a monocyclic or fused ring group having in the ring(s) from 3 to 12 ring atoms, in which at least one ring atom is a heteroatom, such as nitrogen, oxygen or sulfur, the remaining ring atoms being carbon atoms. Heterocycloalkyl may optionally contain 1, 2, 3 or 4 heteroatoms. A heterocycloalkyl group may be fused to another group such as another heterocycloalkyl, or a heteroaryl group. Heterocycloalkyl may also have one of more double bonds, including double bonds to nitrogen (e.g., C═N or N═N) but does not contain a completely conjugated pi-electron system. It will be understood that in certain embodiments, heterocycloalkyl may be advantageously of limited size such as 3- to 8-membered heterocycloalkyl, 5- to 7-membered heterocycloalkyl, 3-, 4-, 5-6-, or 7-membered heterocycloalkyl, and the like. Heterocycloalkyl may be unsubstituted or substituted as described for alkyl or as described in the various embodiments provided herein. Illustrative heterocycloalkyl groups include, but are not limited to, oxiranyl, thianaryl, azetidinyl, oxetanyl, tetrahydrofuranyl, pyrrolidinyl, tetrahydropyranyl, piperidinyl, 1,4-dioxanyl, morpholinyl, 1,4-dithianyl, piperazinyl, oxepanyl, 3,4-dihydro-2H-pyranyl, 5,6-dihydro-2H-pyranyl, 2H-pyranyl, 1, 2, 3, 4-tetrahydropyridinyl, and the like. Illustrative examples of heterocycloalkyl groups shown in graphical representations include the following entities, in the form of properly bonded moieties:

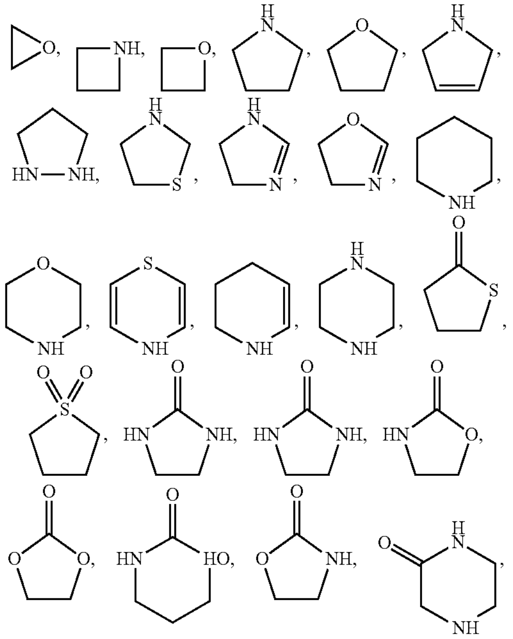

-continued

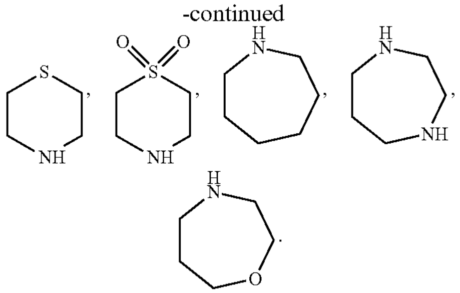

As used herein, "halo" or "halogen" refers to fluorine, chlorine, bromine, or iodine.

The term "oxo" represents a carbonyl oxygen. For example, a cyclopentyl substituted with oxo is cyclopentanone.

As used herein, "bond" absent further characterization refers to a covalent bond.

The term "substituted" means that the specified group or moiety bears one or more substituents. The term "unsubstituted" means that the specified group bears no substituents. Where the term "substituted" is used to describe a structural system, the substitution is meant to occur at any valency-allowed position on the system. In some embodiments, "substituted" means that the specified group or moiety bears one, two, or three substituents. In other embodiments, "substituted" means that the specified group or moiety bears one or two substituents. In still other embodiments, "substituted" means the specified group or moiety bears one substituent.

As used herein, "optional" or "optionally" means that the subsequently described event or circumstance may but need not occur, and that the description includes instances where the event or circumstance occurs and instances in which it does not. For example, "wherein each hydrogen atom in $C_6$-$C_{10}$ aryl is optionally substituted by $R^D$," means that an $R^D$ may be, but need not be, present on any position of the $C_6$-$C_{10}$ aryl by replacement of a hydrogen atom for each $R^D$ group, and the description includes situations where the $C_6$-$C_{10}$ aryl is not substituted with the $R^D$ group.

As used herein, "independently" means that the subsequently described event or circumstance is to be read on its own relative to other similar events or circumstances. For example, in a circumstance where several equivalent hydrogen groups are optionally substituted by another group described in the circumstance, the use of "independently optionally" means that each instance of a hydrogen atom on the group may be substituted by another group, where the groups replacing each of the hydrogen atoms may be the same or different. Or for example, where multiple groups exist all of which can be selected from a set of possibilities, the use of "independently" means that each of the groups can be selected from the set of possibilities separate from any other group, and the groups selected in the circumstance may be the same or different.

As used herein, the phrase "taken together with the atoms to which they are attached" or "taken together with the carbon atom to which they are attached" or "combine to form" means that two substituents (e.g., $R^{1a}$ and $R^{1b}$) each attached to additional atoms to form the structure defined by the claim, such as $C_3$-$C_5$ cycloalkyl. For example, in the context of the compound of Formula I, the phrase "$R^{1a}$ and $R^{1b}$ together with the atoms to which they attached form a $C_3$-$C_8$ cycloalkyl" includes, but is not limited to the compounds represented as follows:

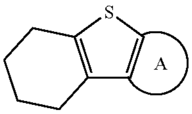 and 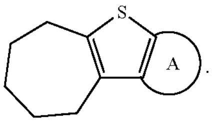.

As used herein, the term "pharmaceutically acceptable salt" refers to those salts which counter ions which may be used in pharmaceuticals. See, generally, S. M. Berge, et al., "Pharmaceutical Salts," J. Pharm. Sci., 1977, 66, 1-19. Preferred pharmaceutically acceptable salts are those that are pharmacologically effective and suitable for contact with the tissues of subjects without undue toxicity, irritation, or allergic response. A compound described herein may possess a sufficiently acidic group, a sufficiently basic group, both types of functional groups, or more than one of each type, and accordingly react with a number of inorganic or organic bases, and inorganic and organic acids, to form a pharmaceutically acceptable salt. Such salts include:

(1) acid addition salts, which can be obtained by reaction of the free base of the parent compound with inorganic acids such as hydrochloric acid, hydrobromic acid, nitric acid, phosphoric acid, sulfuric acid, and perchloric acid and the like, or with organic acids such as acetic acid, oxalic acid, (D) or (L) malic acid, maleic acid, methane sulfonic acid, ethanesulfonic acid, p-toluenesulfonic acid, salicylic acid, tartaric acid, citric acid, succinic acid or malonic acid and the like; or (2) salts formed when an acidic proton present in the parent compound either is replaced by a metal ion, e.g., an alkali metal ion, an alkaline earth ion, or an aluminum ion; or coordinates with an organic base such as ethanolamine, diethanolamine, triethanolamine, trimethamine, N-methylglucamine, and the like.

Pharmaceutically acceptable salts are well known to those skilled in the art, and any such pharmaceutically acceptable salt may be contemplated in connection with the embodiments described herein.

For a compounds of the present disclosure that contain a basic nitrogen, a pharmaceutically acceptable salt may be prepared by any suitable method available in the art, for example, treatment of the free base with an inorganic acid.

The disclosure also relates to pharmaceutically acceptable prodrugs of the compounds of the present invention, and treatment methods employing such pharmaceutically acceptable prodrugs. The term "prodrug" means a precursor of a designated compound that, following administration to a subject, yields the compound in vivo via a chemical or physiological process such as solvolysis or enzymatic cleavage, or under physiological conditions. A "pharmaceutically acceptable prodrug" is a prodrug that is non-toxic, biologically tolerable, and otherwise biologically suitable for administration to the subject. Illustrative procedures for the selection and preparation of suitable prodrug derivatives are described, for example, in "Design of Prodrugs," ed. H. Bundgaard, Elsevier, 1985.

Any formula given herein is also intended to represent unlabeled forms as well as isotopically labeled forms of the compounds. Isotopically labeled compounds have structures depicted by the formulas given herein except that one or more atoms are replaced by an atom having a selected atomic mass or mass number. Examples of isotopes that can be incorporated into compounds of the disclosure include isotopes of hydrogen, carbon, nitrogen, oxygen, phosphorous, fluorine, chlorine, and iodine, such as $^{2}H$, $^{3}H$, $^{11}C$, $^{13}C$, $^{14}C$, $^{15}N$, $^{18}O$, $^{17}O$, $^{31}P$, $^{32}P$, $^{35}S$, $^{18}F$, $^{36}Cl$, and $^{125}I$, respectively. Such isotopically labelled compounds are useful in metabolic studies (preferably with 14C), reaction kinetic studies (with, for example 2H or 3H), detection or imaging techniques [such as positron emission tomography (PET) or single-photon emission computed tomography (SPECT)] including drug or substrate tissue distribution assays, or in radioactive treatment of patients. Further, substitution with heavier isotopes such as deuterium (i.e., 2H) may afford certain therapeutic advantages resulting from greater metabolic stability, for example increased in vivo half-life or reduced dosage requirements. Isotopically labeled compounds of this disclosure and prodrugs thereof can generally be prepared by carrying out the procedures disclosed in the schemes or in the examples and preparations described below by substituting a readily available isotopically labeled reagent for a non-isotopically labeled reagent.

Embodiments

The present disclosure is directed to compositions and methods for treating Human Papillomavirus (HPV) infections. In one embodiment, compositions comprising the HPV E6 binding compounds disclosed herein are formulated for topical application to the cervix, anus, or oropharynx. The compounds disclosed herein have been found to bind to amino acid residues of the E6AP binding pocket of HPV E6 protein and interfere with the activities of HPV E6, including its ability to interact with E6AP. More particularly, the HPV E6 binding compounds disclosed herein form a covalent bond with a cysteine residue (e.g., Cys51) within an E6AP binding pocket in human papilloma virus (HPV) E6 protein, thereby preventing binding of the E6 protein to an E6AP protein. Abrogation of HPV E6 activity has been found to lead to growth arrest of HPV-infected cells and/or cell death of HPV cervical cancer cell lines.

In accordance with one embodiment, compounds that directly and irreversibly bind to the HPV-16 E6 protein are provided. In one embodiment these compounds are used in methods relating to treatment, such as inhibition or prevention or amelioration, of HPV infections, including HPV E6 infections, with one or more of the HPV E6 binding compounds disclosed herein, or mixtures thereof as disclosed herein. In one aspect, the small molecules described herein disrupt the E6 interaction with E6AP and thereby restoring p53 functions in HPV-infected cells. In one aspect, the present disclosure is directed to a method for treating HPV infections (e.g., reducing HPV E6 levels, reducing the total number of infectious particles, or reducing the number of infected cells) in a subject in need of HPV treatment. In one embodiment the method of reducing HPV includes administering one or more of an E6 binding compounds disclosed herein or mixtures thereof, to the subject. In another aspect, the present disclosure is directed to a method for ameliorating HPV, e.g., HPV E6, in a subject in need thereof, wherein the method includes administering any of the E6 binding compounds disclosed herein, or mixtures thereof, to the subject.

In one aspect, the present disclosure is directed to a method for preventing an HPV infection in a subject in need thereof. The method includes prophylactically administering a compound comprising any of the E6 binding compounds disclosed herein or mixtures thereof, to the subject.

Suitable subjects in need of treatment include subjects having (or suspected of having, based on exhibited symptoms, or known exposure) an HPV infection. In one embodiment a subject known to be exposed to HPV, is administered a composition comprising an E6 binding compound of the present disclosure even prior to the subject demonstrating any symptoms of infection.

In accordance with embodiment 1 compounds that specifically bind to HPV E6 are provided wherein the compounds have the general structure of Formula I:

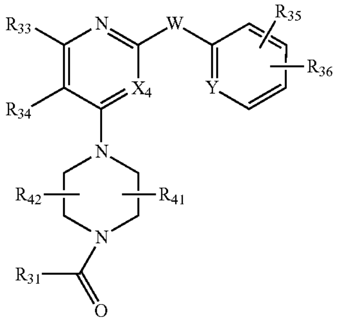

wherein Y is C or N;

$X_4$ is N or C;

W is $-(CH_2)_n-$ or $-CH{=}CR_{32}-$;

$R_{32}$ is H or $-(CH_2)_n-$ n is an integer selected from the range of 0-4;

$R_{31}$ is selected from the group consisting of $-CH{=}CH_2$, $-CR_{51}{=}CH_2$, $-CH{=}CHCH_2N(CH_3)_2$, $-CH{=}CHCH_3$, $CH_2$(halo) and $CH_3$ wherein $R_{51}$ is H or halo, optionally where $R_{51}$ is H or F, optionally wherein $R_{31}$ is $-CH{=}CH_2$;

$R_{33}$ and $R_{34}$ together with the atoms to which they are attached form a ring structure selected from the group consisting of

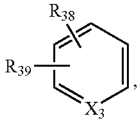, 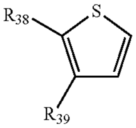, and 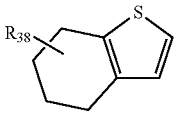;

$X_3$ is C or N;

$R_{38}$ is selected from the group consisting of H, $-OCH_3$, $-OCF_3$, $-OCH_2CH_3$, and $-OCH_2CH_2OCH_3$;

$R_{39}$ is H, halo or $CH_3$;

$R_{35}$ is selected from the group consisting of H and halo:

$R_{36}$ is selected from the group consisting of H, halo, $-OCH_3$, $-OCH_2CH_3$ and $CONHCH_3$;

$R_{41}$ is H or $C_1$-$C_4$ alkyl;

$R_{42}$ is H, $-CN$, $C_1$-$C_4$ alkyl, or $R_{41}$ and $R_{42}$ together with the atoms to which they are attached form a 4-6 membered ring; with the proviso that when $R_{41}$ and $R_{42}$ are both H, either $R_{36}$ is $-OCH_2CH_3$, or $R_{38}$ is other than H.

In accordance with embodiment 2 an HPV E6 binding compound is provided having the general structure of Formula I, wherein Y is C or N;

$X_4$ is N or C;

W is $-(CH_2)_n$ or $-CH{=}CH-$;

n is an integer selected from the range of 2-4;

$R_{31}$ is selected from the group consisting of $-CH{=}CH_2$, $-CH{=}CHCH_2N(CH_3)_2$, $-CH{=}CHCH_3$, $CH_2$(halo) and $CH_3$, optionally wherein $R_{31}$ is $-CH{=}CH_2$;

$R_{33}$ and $R_{34}$ together with the atoms to which they are attached form a ring structure selected from the group consisting of

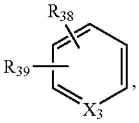, 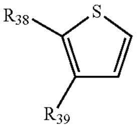, and 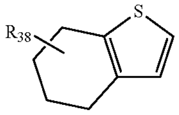;

$X_3$ is C or N;

$X_4$ is N;

$R_{38}$ is selected from the group consisting of H, $-OCH_3$, $-OCF_3$, $-OCH_2CH_3$, and $-OCH_2CH_2OCH_3$;

$R_{39}$ is H, halo or $CH_3$;

$R_{35}$ is selected from the group consisting of H and halo:

$R_{36}$ is selected from the group consisting of H, halo, $-OCH_3$, $-OCH_2CH_3$ and $CONHCH_3$;

$R_{41}$ is H or $C_1$-$C_4$ alkyl;

$R_{42}$ is H, $-CN$, $C_1$-$C_4$ alkyl, or $R_{41}$ and $R_{42}$ together with the atoms to which they are attached form a 4-6 membered ring; optionally with the proviso that when $R_{41}$ and $R_{42}$ are both H, either $R_{36}$ is $-OCH_2CH_3$, or $R_{38}$ is other than H.

In accordance with embodiment 3 an HPV E6 binding compound of embodiment 1 or 2 is provided having the general structure of Formula I, wherein $X_4$ is N;

W is a bond (i.e., n=0);

$R_{31}$ is selected from the group consisting of $-CH{=}CH_2$, $-CH{=}CHCH_2N(CH_3)_2$, $-CH{=}CHCH_3$, $CH_2$(halo) and $CH_3$, optionally wherein $R_{31}$ is $-CH{=}CH_2$;

$R_{33}$ and $R_{34}$ together with the atoms to which they are attached form a ring structure of

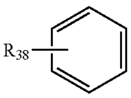, $R_{38}$ is selected from the group consisting of H, $-OCH_3$, $-OCH_2CH_3$, and $-OCH_2CH_2OCH_3$;

$R_{39}$ is H;

$R_{35}$ is selected from the group consisting of H and halo:

$R_{36}$ is selected from the group consisting of H, halo, $-OCH_3$, and $-OCH_2CH_3$;

$R_{41}$ is H or $C_1$-$C_4$ alkyl;

$R_{42}$ is H, $-CN$, or $C_1$-$C_4$ alkyl, optionally with the proviso that when $R_{41}$ and $R_{42}$ are both H, either $R_{36}$ is $-OCH_2CH_3$, or $R_{38}$ is other than H.

In accordance with embodiment 4 an HPV E6 binding compound of any one of embodiments 1-3 is provided having the general structure of Formula I, wherein $R_{41}$ and $R_{42}$ together with the atoms to which they are attached form a 4-6 membered ring (as part of a bridged bicyclic ring); optionally wherein $R_{41}$ and $R_{42}$ together with the atoms to which they are attached form a 4 membered ring.

In accordance with embodiment 5 an HPV E6 binding compound of any one of embodiments 1-4 is provided having the general structure of Formula II:

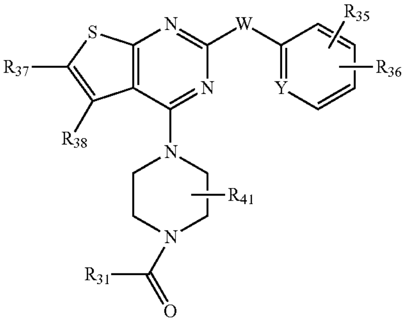

wherein

Y is C or N;

W is —$(CH_2)_n$—;

n is 2;

$R_{31}$ is selected from the group consisting of —CH═$CH_2$, —CH═$CHCH_2N(CH_3)_2$, —CH═$CHCH_3$, $CH_2$(halo) and $CH_3$, optionally wherein $R_{31}$ is —CH═$CH_2$;

$R_{37}$ and $R_{38}$ are each H or $R_{37}$ and $R_{38}$ together with the atoms to which they are attached form a ring structure of

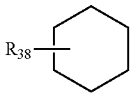;

$R_{38}$ is H, halo or $CH_3$, optionally wherein $R_{38}$ is H;

$R_{35}$ is halo:

$R_{36}$ is selected from the group consisting of halo, —$OCH_3$, and —$OCH_2CH_3$; and $R_{41}$ is H or $C_1$-$C_4$ alkyl.

In accordance with embodiment 6, an HPV E6 binding compound of any one of embodiments 1-4 is provided having the general structure of Formula III:

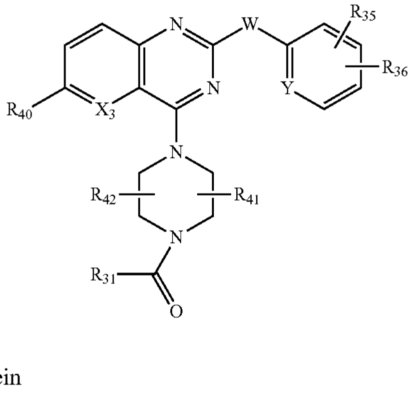

wherein

Y is C or N;

$X_3$ is C or N;

W is —$(CH_2)_n$ or —CH═CH—;

n is an integer selected from the range of 0-4;

$R_{31}$ is selected from the group consisting of —CH═$CH_2$, —$CR_{51}$═$CH_2$, —CH═$CHCH_2N(CH_3)_2$, —CH═$CHCH_3$, $CH_2$(halo) and $CH_3$ wherein $R_{51}$ is H or halo, optionally where $R_{51}$ is H or F, optionally wherein $R_{31}$ is —CH═$CH_2$;

$R_{35}$ is selected from the group consisting of H and halo:

$R_{36}$ is selected from the group consisting of H, halo, —$OCH_3$, —$OCH_2CH_3$ and $CONHCH_3$;

$R_{40}$ is selected from the group consisting of H, —$OCH_3$, —$OCH_2CH_3$, and —$OCH_2CH_2OCH_3$;

$R_{41}$ is H or $C_1$-$C_4$ alkyl;

$R_{42}$ is H, —CN, $C_1$-$C_4$ alkyl, or $R_{41}$ and $R_{42}$ together with the atoms to which they are attached form a 4-6 membered ring (as part of a bridged bicyclic ring); optionally with the proviso that when $R_{41}$ and $R_{42}$ are both H, either $R_{36}$ is —$OCH_2CH_3$, or $R_{40}$ is other than H.

In accordance with embodiment 7 an HPV E6 binding compound of any one of embodiments 1-6 is provided, wherein $X_3$ is C or N;

W is —$(CH_2)_2$ or —CH═CH—;

$R_{31}$ is selected from the group consisting of —CH═$CH_2$, —CH═$CHCH_2N(CH_3)_2$, —CH═$CHCH_3$, $CH_2$(halo) and $CH_3$, optionally wherein $R_{31}$ is —CH═$CH_2$;

$R_{38}$ or $R_{40}$ is selected from the group consisting of H, —$OCH_3$, —$OCH_2CH_3$, and —$OCH_2CH_2OCH_3$;

$R_{35}$ is selected from the group consisting of H and halo:

$R_{36}$ is selected from the group consisting of H, halo, —$OCH_3$, and —$OCH_2CH_3$;

$R_{41}$ is H;

$R_{42}$ is H, —CN, or $C_1$-$C_4$ alkyl, optionally with the proviso that when $R_{41}$ and $R_{42}$ are both H, either $R_{36}$ is —$OCH_2CH_3$, or $R_{38}$ is other than H.

In accordance with embodiment 8 an HPV E6 binding compound of any one of embodiments 1-4, 6 or 7 is provided having the general structure of Formula III, wherein $X_3$ is C; and $R_{42}$ is —CN, or $C_1$-$C_4$ alkyl.

In accordance with embodiment 9 an HPV E6 binding compound of any one of embodiments 1-4, 6, 7 or 8 is provided having the general structure of Formula III, wherein $R_{40}$ is selected from the group consisting of —$OCH_3$, —$OCH_2CH_3$, and —$OCH_2CH_2OCH_3$.

In accordance with embodiment 10 an HPV E6 binding compound of any one of embodiments 1-4, 6, 7 or 8 is provided having the general structure of Formula III, wherein $X_3$ is N.

In accordance with embodiment 11 an HPV E6 binding compound of any one of embodiments 1-4, 6, 7 or 8 is provided having the general structure of Formula III, wherein $X_3$ is C.

In accordance with embodiment 12 an HPV E6 binding compound of any one of embodiments 1-4, 6, 7, 8, 9, 10 or 11 is provided having the general structure of Formula III, wherein $R_{35}$ is halo; and $R_{36}$ is selected from the group consisting of H, halo, —$OCH_3$, —$OCH_2CH_3$ and $CONHCH_3$, optionally wherein $R_{36}$ is —$OCH_3$, —$OCH_2CH_3$, optionally wherein $R_{36}$ is halo.

In accordance with embodiment 13 an HPV E6 binding compound of any one of embodiments 1-4, 6, 7, 8, 9, 10, 11 or 12 is provided having the general structure of Formula III, wherein $R_{41}$ is H; and $R_{42}$ is —CN, or $C_1$-$C_4$ alkyl.

In accordance with embodiment 13 an HPV E6 binding compound of any one of embodiments 1-4, 6, 7, 8, 9, 10, 11 or 12 is provided having the general structure of Formula III, wherein $R_{41}$ and $R_{42}$ together with the atoms to which they are attached form a 4-5 membered cycloalkyl ring (as part of a bridged bicyclic ring).

In accordance with embodiment 14 an HPV E6 binding compound is provided wherein the compound has the general structure of Formula I:

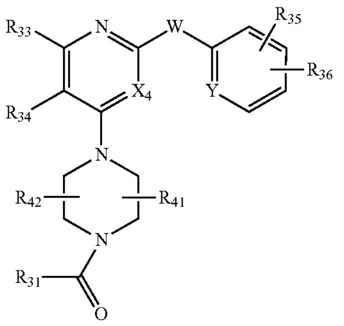

wherein Y is C or N;

$X_4$ is N;

W is $-(CH_2)_2$ or $-CH{=}CH-$;

$R_{31}$ is selected from the group consisting of $-CH{=}CH_2$, or $-CH{=}CHCH_3$;

$R_{33}$ and $R_{34}$ together with the atoms to which they are attached form a ring structure of

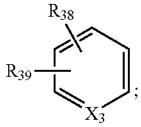

;

$X_3$ is C or N;

$R_{38}$ is selected from the group consisting of H, $-OCH_3$, $-OCH_2CH_3$, and $-OCH_2CH_2OCH_3$;

$R_{39}$ is H;

$R_{35}$ is selected from the group consisting of H and halo:

$R_{36}$ is selected from the group consisting of H, halo, $-OCH_3$, and $-OCH_2CH_3$;

$R_{41}$ is H;

$R_{42}$ is H, —CN, or $C_1$-$C_4$ alkyl, optionally with the proviso that when $R_{41}$ and $R_{42}$ are both H, either $R_{36}$ is $-OCH_2CH_3$, or $R_{38}$ is other than H.

In accordance with embodiment 15, an HPV E6 binding compound of embodiment 14 is provided wherein W is $-(CH_2)_2$.

In accordance with embodiment 16, an HPV E6 binding compound of embodiment 14 is provided wherein W is $-CH{=}CH-$.

In accordance with embodiment 17, an HPV E6 binding compound of any one of embodiments 14-16 is provided wherein $X_3$ is C and $R_{38}$ is selected from the group consisting of $-OCH_3$, $-OCH_2CH_3$, and $-OCH_2CH_2OCH_3$.

In accordance with embodiment 18, an HPV E6 binding compound of any one of embodiments 14-16 is provided wherein $X_3$ is N and $R_{38}$ is selected from the group consisting of $-OCH_3$, $-OCH_2CH_3$, and $-OCH_2CH_2OCH_3$.

In accordance with embodiment 19 an HPV E6 binding compound is provided having the general structure of Formula VI:

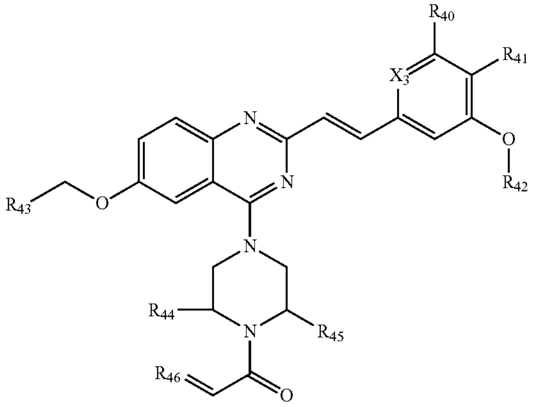

wherein $X_3$ is C or N;

$R_{40}$ is H, halo or $CH_3$;

$R_{41}$ is H or Halo;

$R_{42}$ is $CH_3$ or

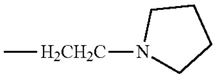

;

$R_{43}$ is $CH_3$, $CH_2OCH_3$, or $C_1$-$C_3$ cycloalkyl;

$R_{44}$ and $R_{45}$ are independently H or $-(CH_2)_n$ or $R_{44}$ and $R_{45}$ together with the atoms to which they are attached form a bridged bicyclic ring; and $R_{46}$ is $CH_3$, $CH_2NCH_3CH_3$, N-methyl pyrrolidine or $CH_2R_{47}$, wherein $R_{47}$ is an N-linked morpholine or piperidine ring and n is an integer selected from the range of 2-4.

In accordance with embodiment 20 an HPV E6 binding compound of embodiment 21 is provided wherein $X_3$ is N;

$R_{40}$ is H;

$R_{41}$ is H or F and $R_{42}$ is $CH_3$.

In accordance with embodiment 21 an HPV E6 binding compound is provided having the general structure of

1

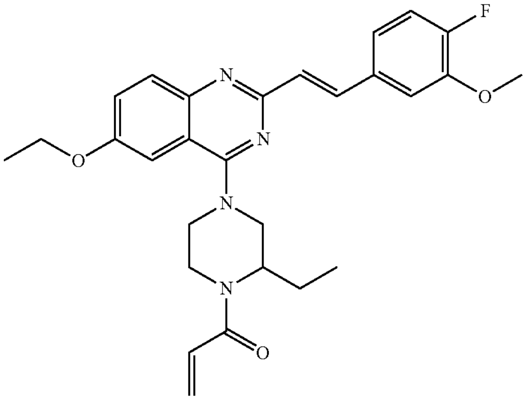

,

-continued
2
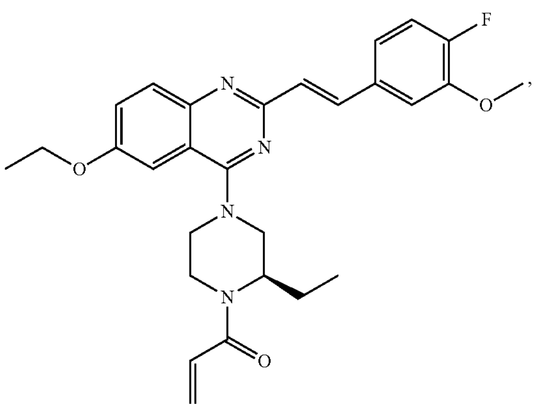
3
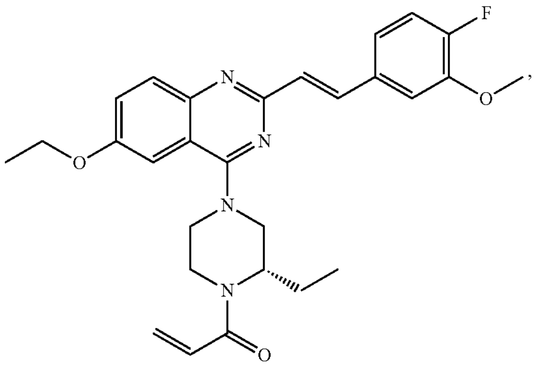
4
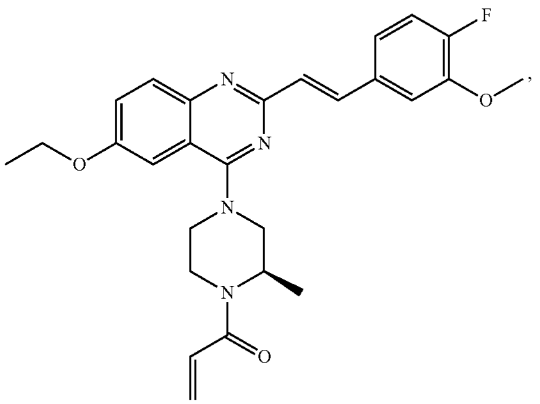
5
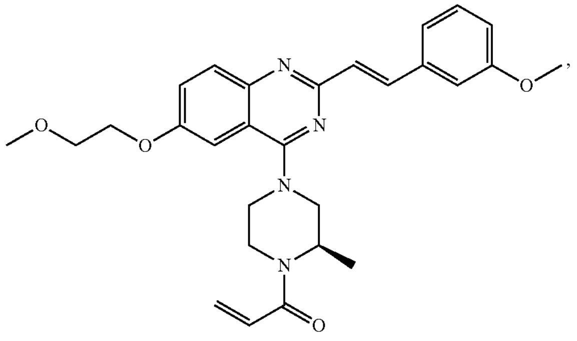
-continued
6
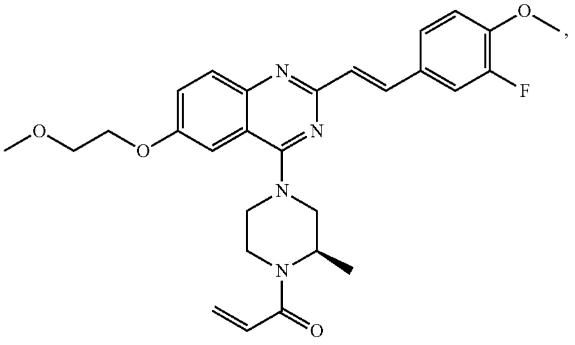
7
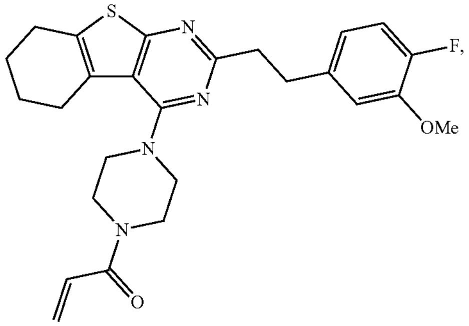
8
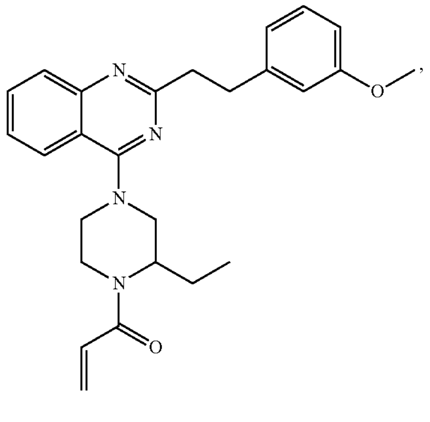
9
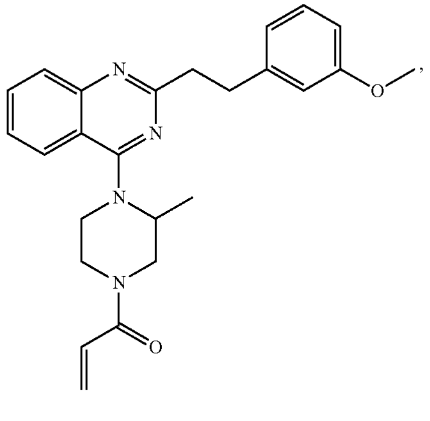

-continued
10
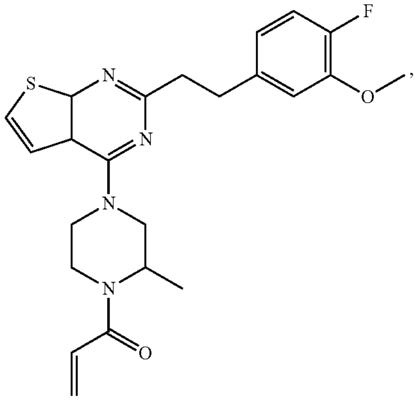
11
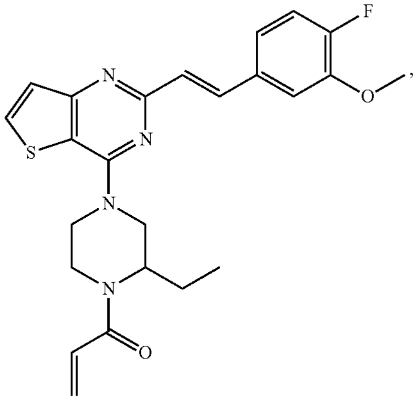
12
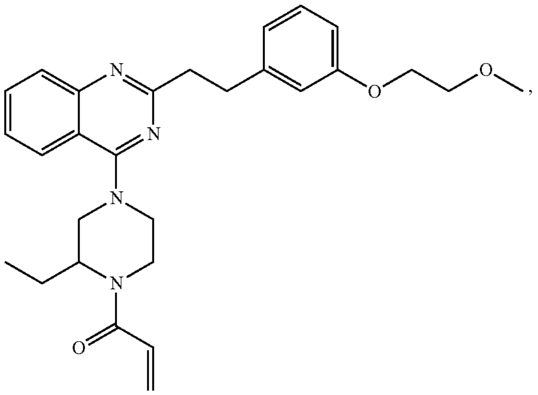
13
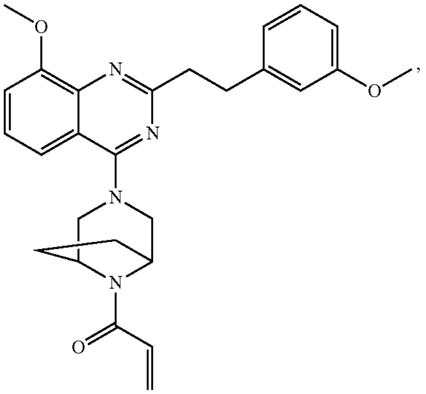
-continued
14
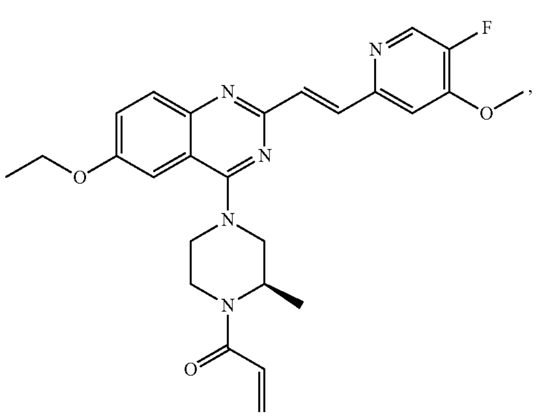
15
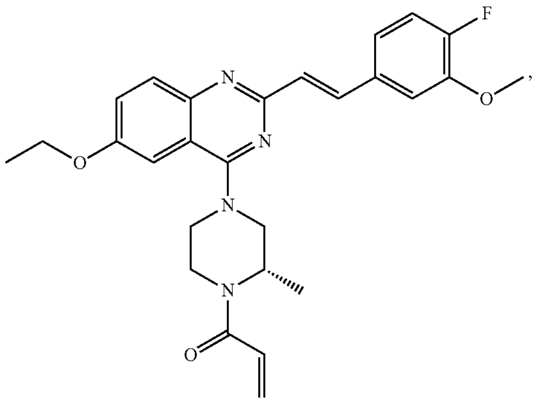
16
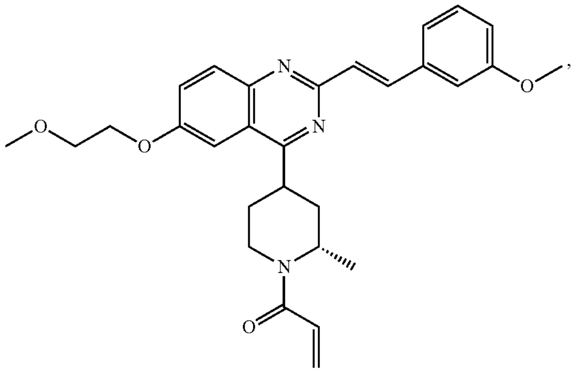
17
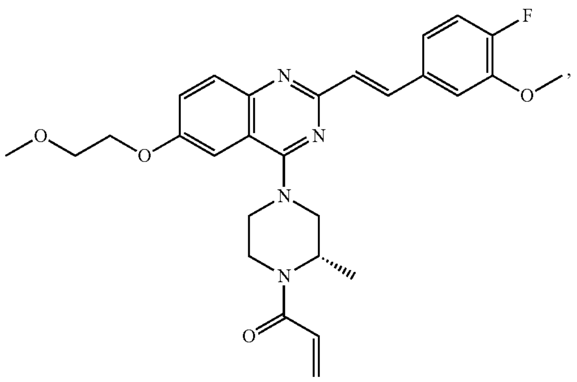

-continued

18

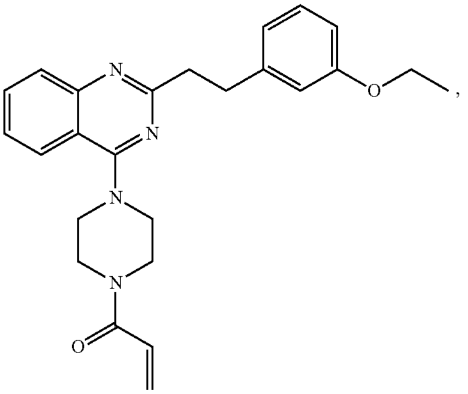

19

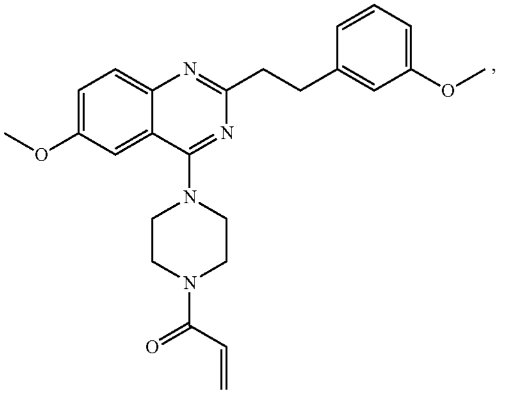

20

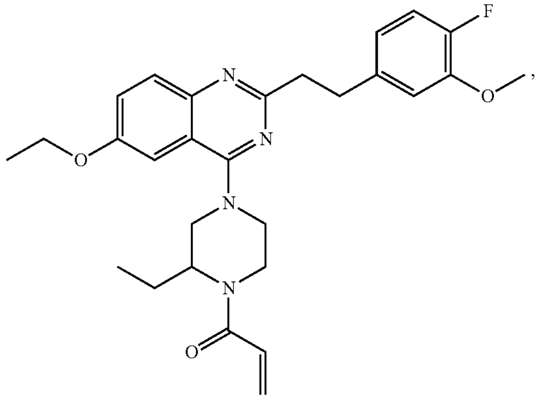

or the structure of any one of compounds 29 through 47.

In accordance with embodiment 22, a pharmaceutical composition is provided comprising any of the HPV E6 binding compounds of embodiments 1-21 and an acceptable carrier, optionally wherein the pharmaceutical composition is formulated for topical application, including for example as a cream.

In accordance with embodiment 23 a formulation is provided comprising any of the HPV E6 binding compounds of embodiments 1-21 and pharmaceutically-acceptable adjuvant, diluent or carrier.

In accordance with embodiment 24 a method for treating an HPV infection is provided, wherein the method comprises the step of delivering a pharmaceutical composition of embodiment 22 or a formulation of embodiment 23 to a patient in need of treatment.

In accordance with embodiment 25 the method for treating an HPV infection of embodiment 24 is provided, wherein said formulation is delivered orally, transdermally, topically, subcutaneously, intramuscularly, or intravenously.

In accordance with embodiment 26 the method for treating an HPV infection of embodiment 24 or 25 is provided, the formulation is formulated for topical application to the cervix, anus, or oropharynx.

In accordance with embodiment 27 the method for treating an HPV infection of any one of embodiments 24-26 is provided, wherein said formulation comprises an effective dose for transdermal delivery of about 0.01% to about 10% of the compound of embodiment 1.

In accordance with embodiment 28 the method for treating an HPV infection of any one of embodiments 24-27 is provided, wherein said formulation is a time-release formulation.

In accordance with embodiment 29 the method for treating an HPV infection of any one of embodiments 24-28 is provided, wherein said formulation inhibits E6AP binding to HPV E6 preventing ubiquitination of p53.

In accordance with embodiment 30 the method for treating an HPV infection of any one of embodiments 24-29 is provided, wherein the formulation further comprises a compound selected from the group consisting of fatty acids, glucose, amino acids, cholesterol, lipids, glycosides, alkaloids, and natural phenols.

Each of the following compounds represents an embodiment of the generic structures provided above and is based thereon. In each instance, a synthesis pathway resulting in the preferred compound is shown. The numbering in the synthesis pathways does not reflect the Compound numbering below.

Compound 29 is shown below:

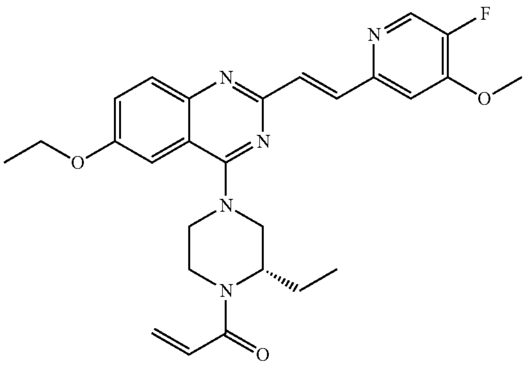 [SMILES: C=CC(=O)N1CCN(c2nc(/C=C/c3cc(OC)c(F)cn3)nc3ccc(OCC)cc23)C[C@@H]1CC]

Figure 9:
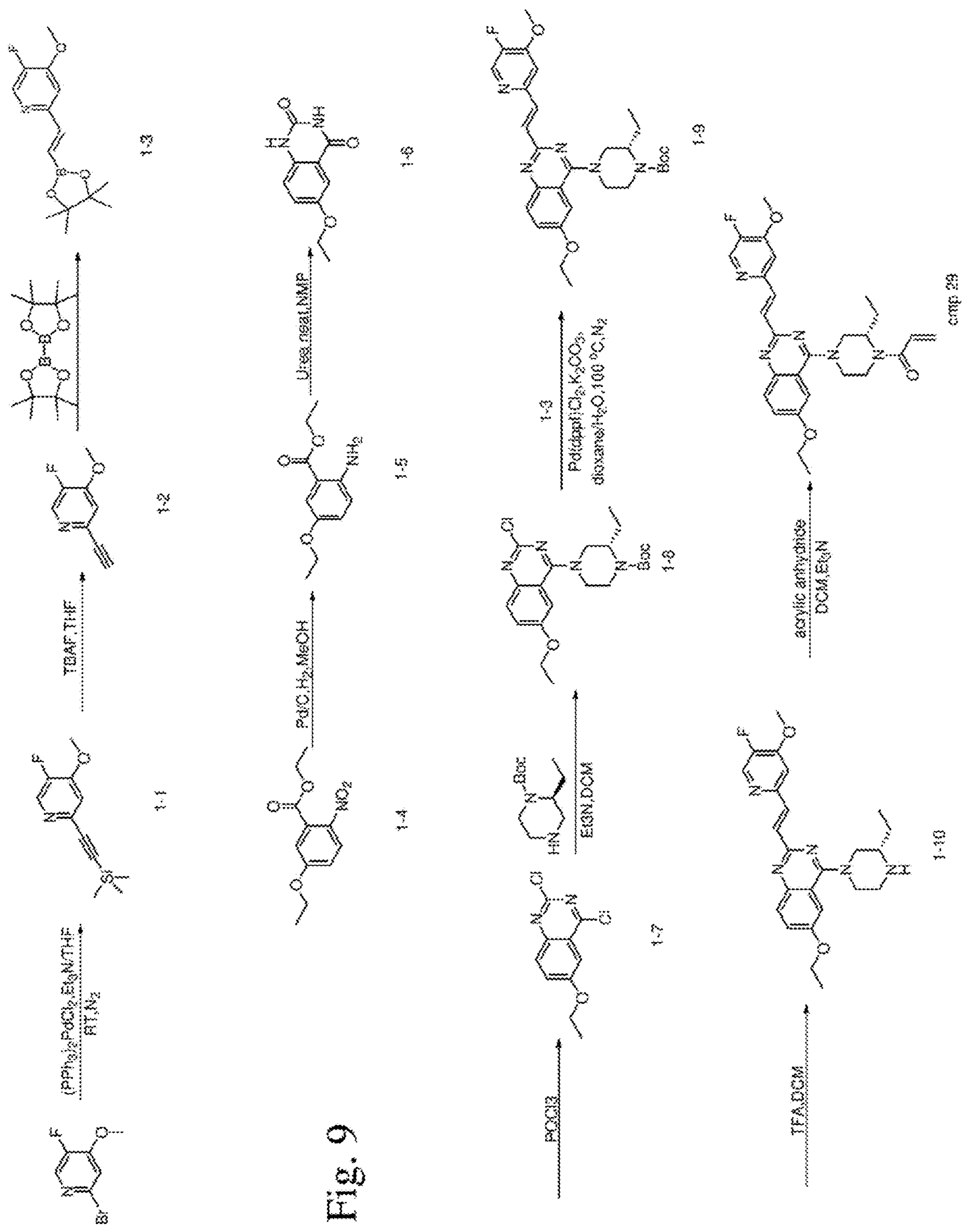
FIG. 9 provides the synthetic scheme for Compound 29.

The synthesis pathway used to make Compound 29 is shown in FIG. 9:

Compound 30 is shown below:

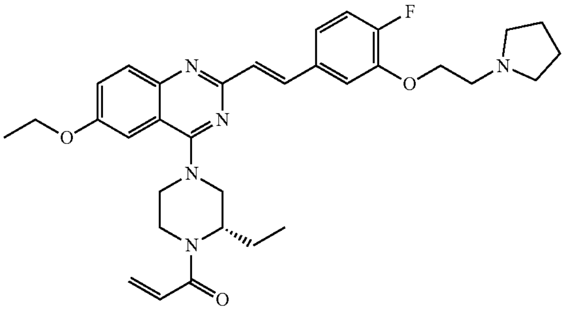 [SMILES: C=CC(=O)N1CCN(c2nc(/C=C/c3ccc(F)c(OCCN4CCCC4)c3)nc3ccc(OCC)cc23)C[C@@H]1CC]

Figure 10:
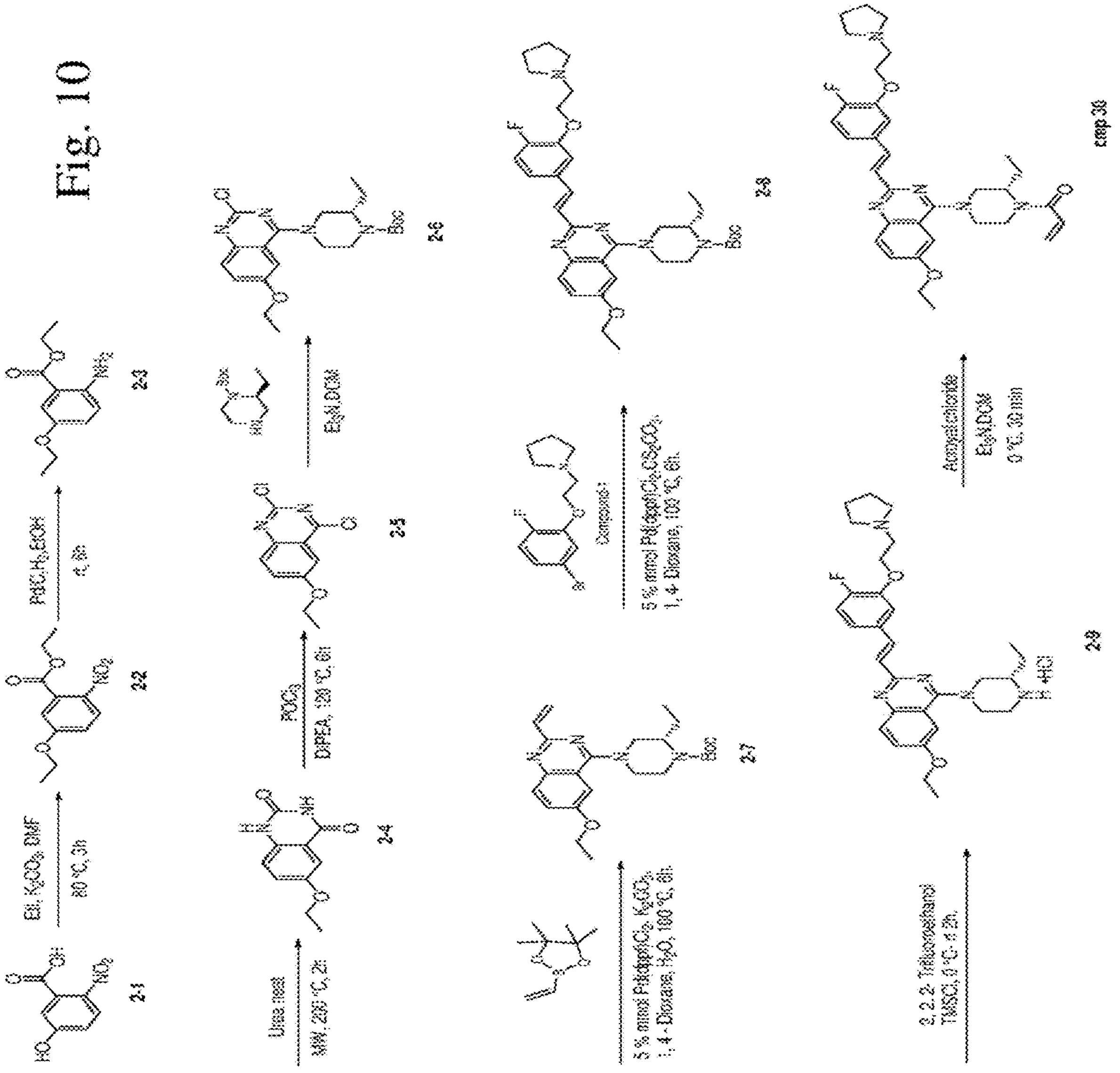
FIG. 10 provides the synthetic scheme for Compound 30.

The synthetic pathway that resulted in Compound 30 is shown in FIG. 10

Compound 31 is shown below:

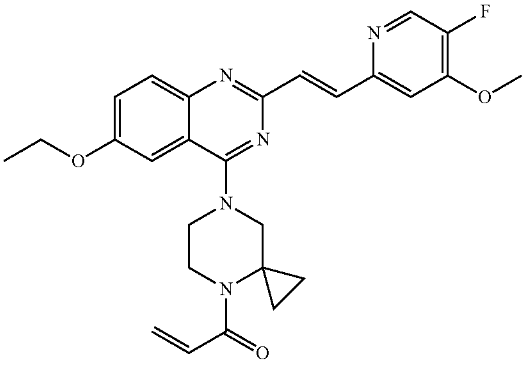 [SMILES: C=CC(=O)N1CCN(c2nc(/C=C/c3cc(OC)c(F)cn3)nc3ccc(OCC)cc23)CC12CC2]

Figure 11:
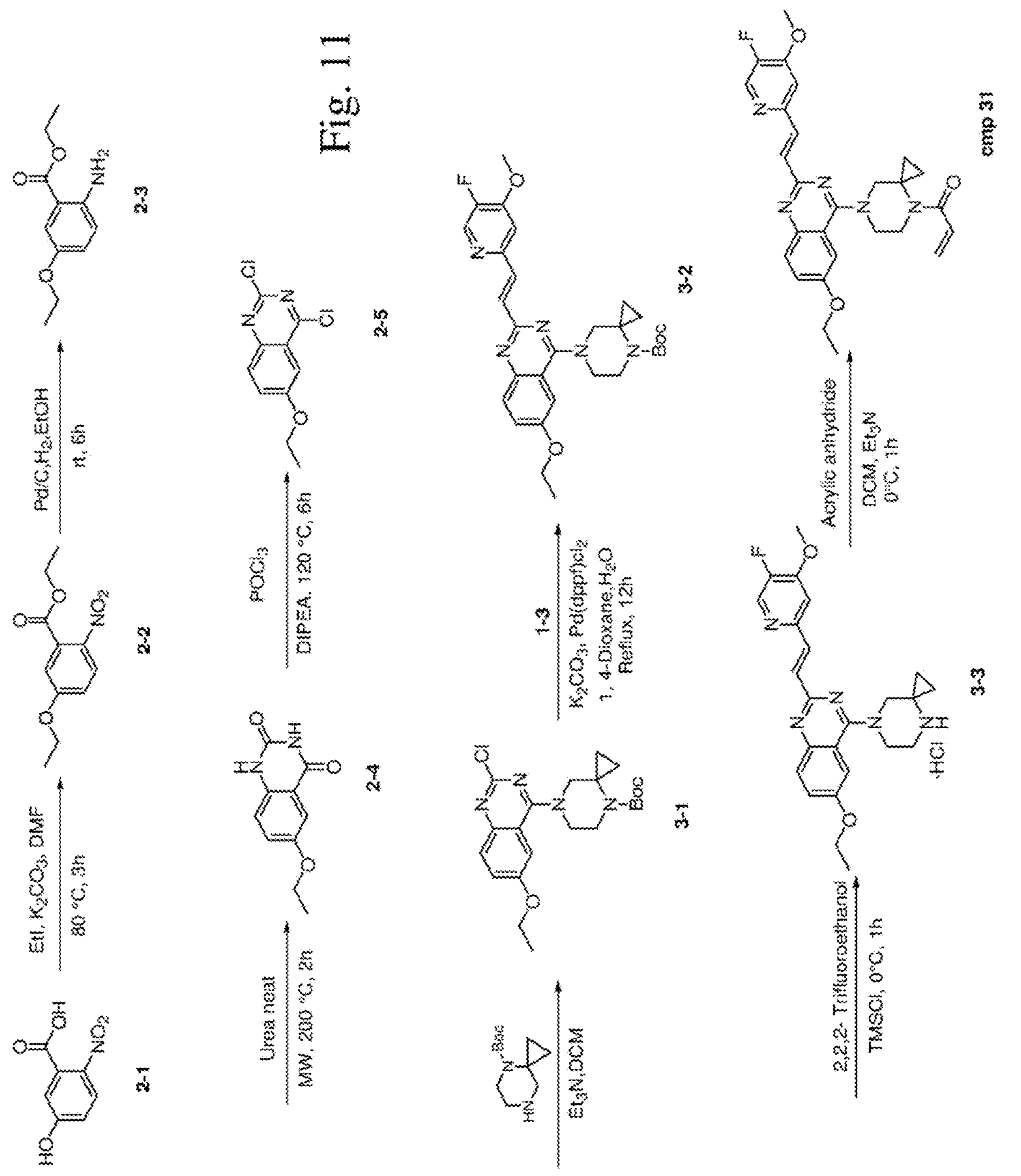
FIG. 11 provides the synthetic scheme for Compound 31.

The synthesis pathway resulting in Compound 31 is shown in FIG. 11.

Compound 32 is shown below:

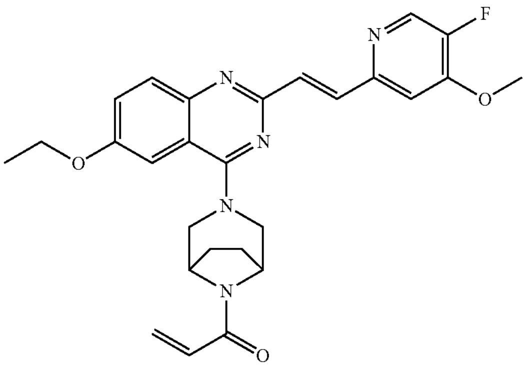 [SMILES: C=CC(=O)N1C2CCC1CN(c1nc(/C=C/c3cc(OC)c(F)cn3)nc3ccc(OCC)cc13)C2]

Figure 12:
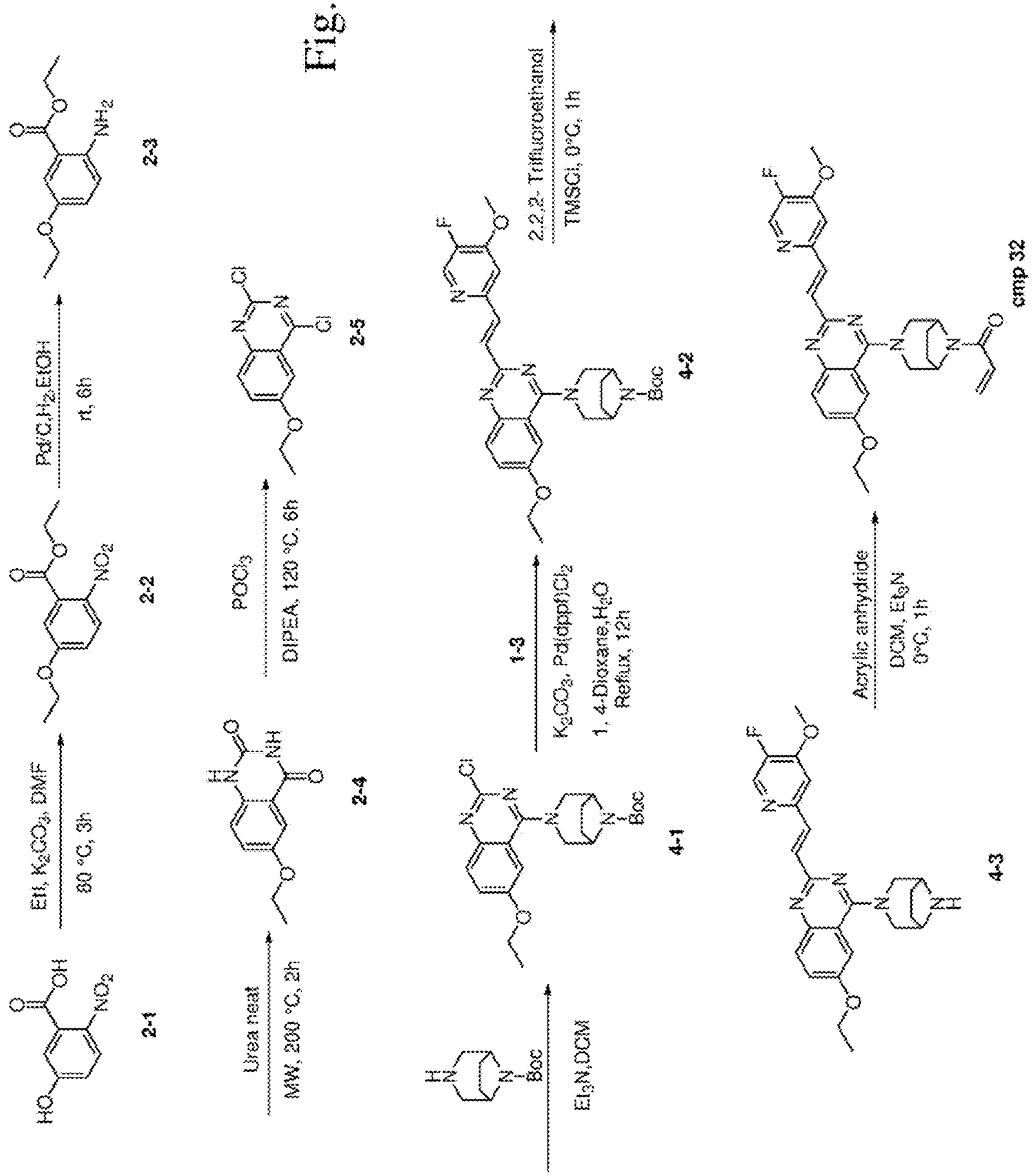
FIG. 12 provides the synthetic scheme for Compound 32.

The synthesis pathway leading to compound 32 is shown in FIG. 12

Compound 33 is shown below:

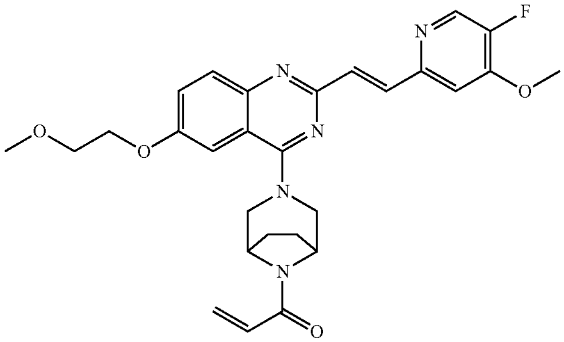

Figure 13:
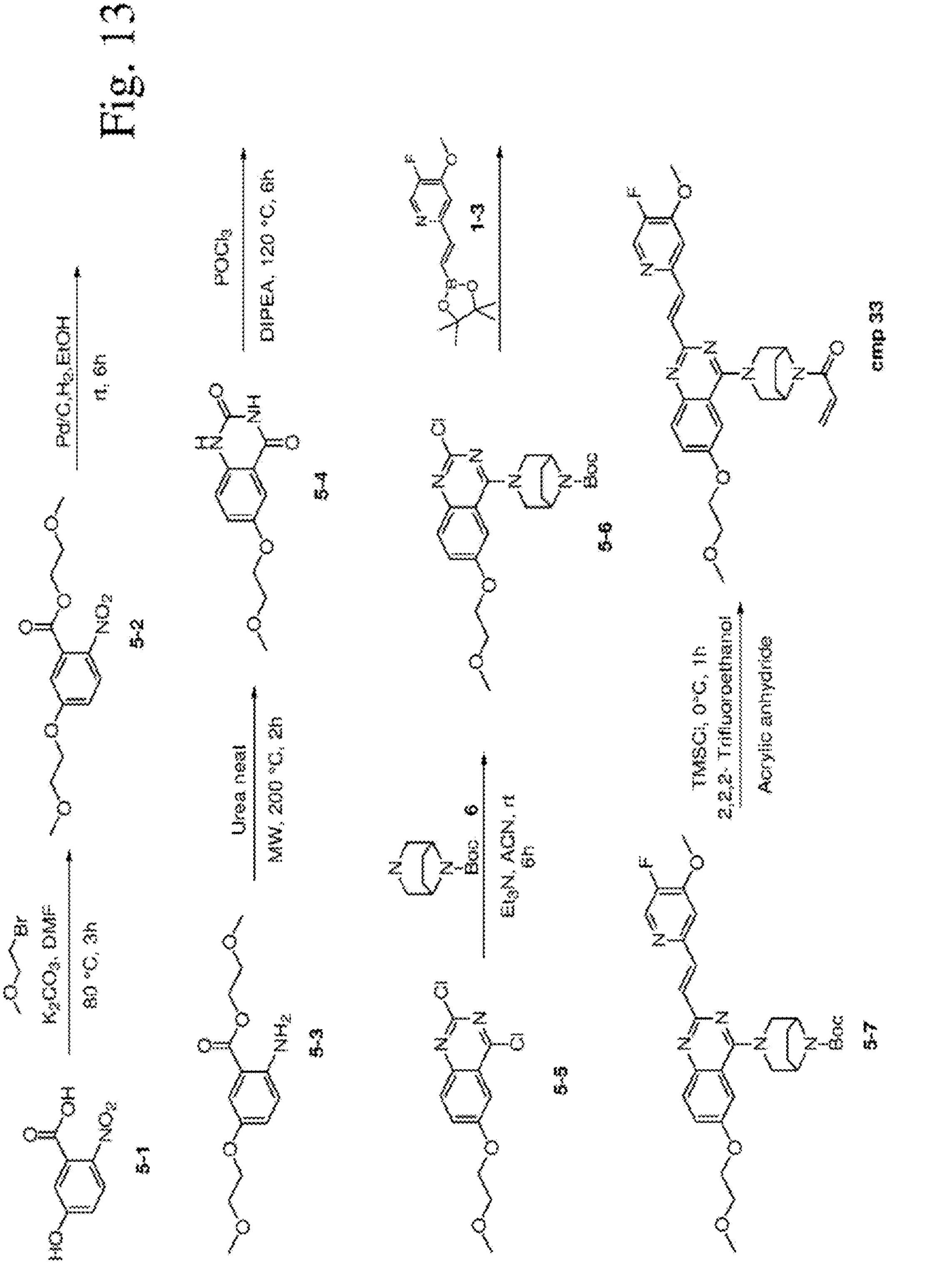
FIG. 13 provides the synthetic scheme for Compound 33.

The synthetic pathway resulting in Compound 33 is shown FIG. 13

Compound 34 is shown below:

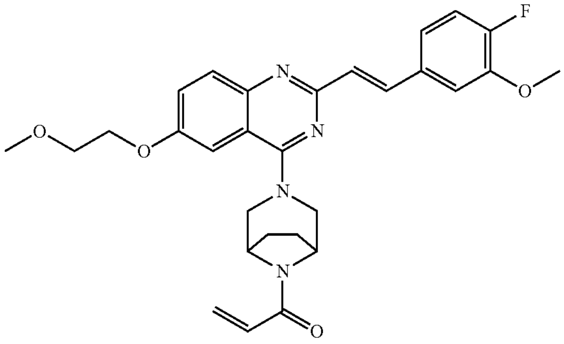

Figure 14:
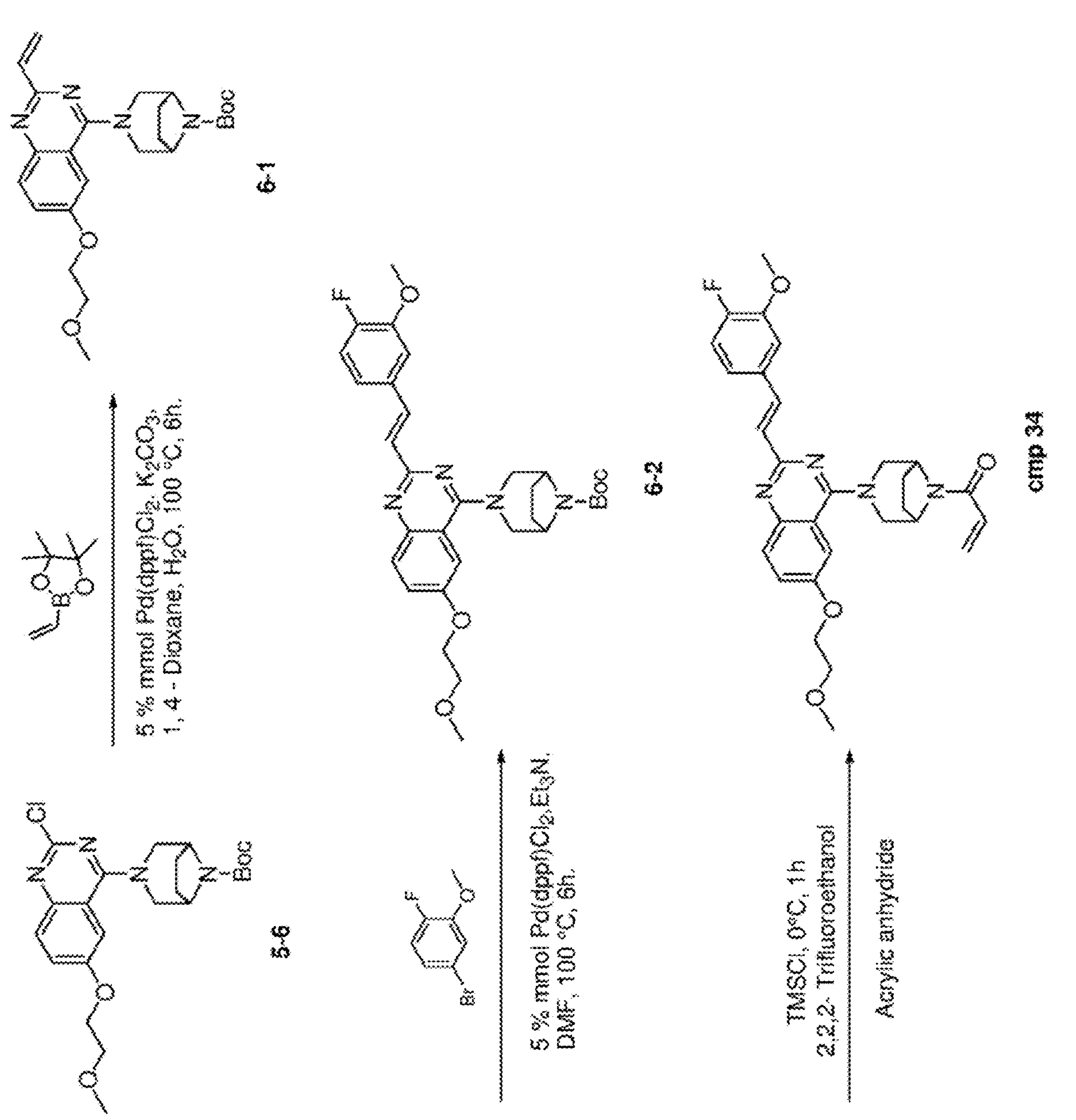
FIG. 14 provides the synthetic scheme for Compound 34.

The synthetic pathway leading to Compound 34 is shown in FIG. 14

Compound 35 is shown below:

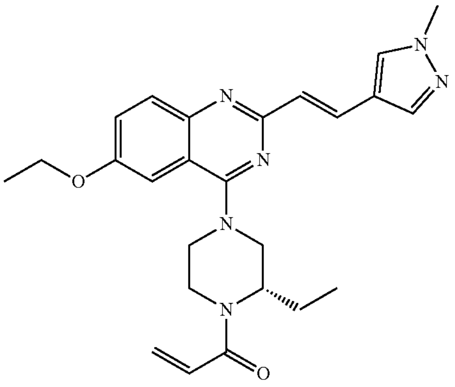 [SMILES: C=CC(=O)N1CCN(c2nc(/C=C/c3cnn(C)c3)nc3ccc(OCC)cc23)C[C@@H]1CC]

Figure 15:
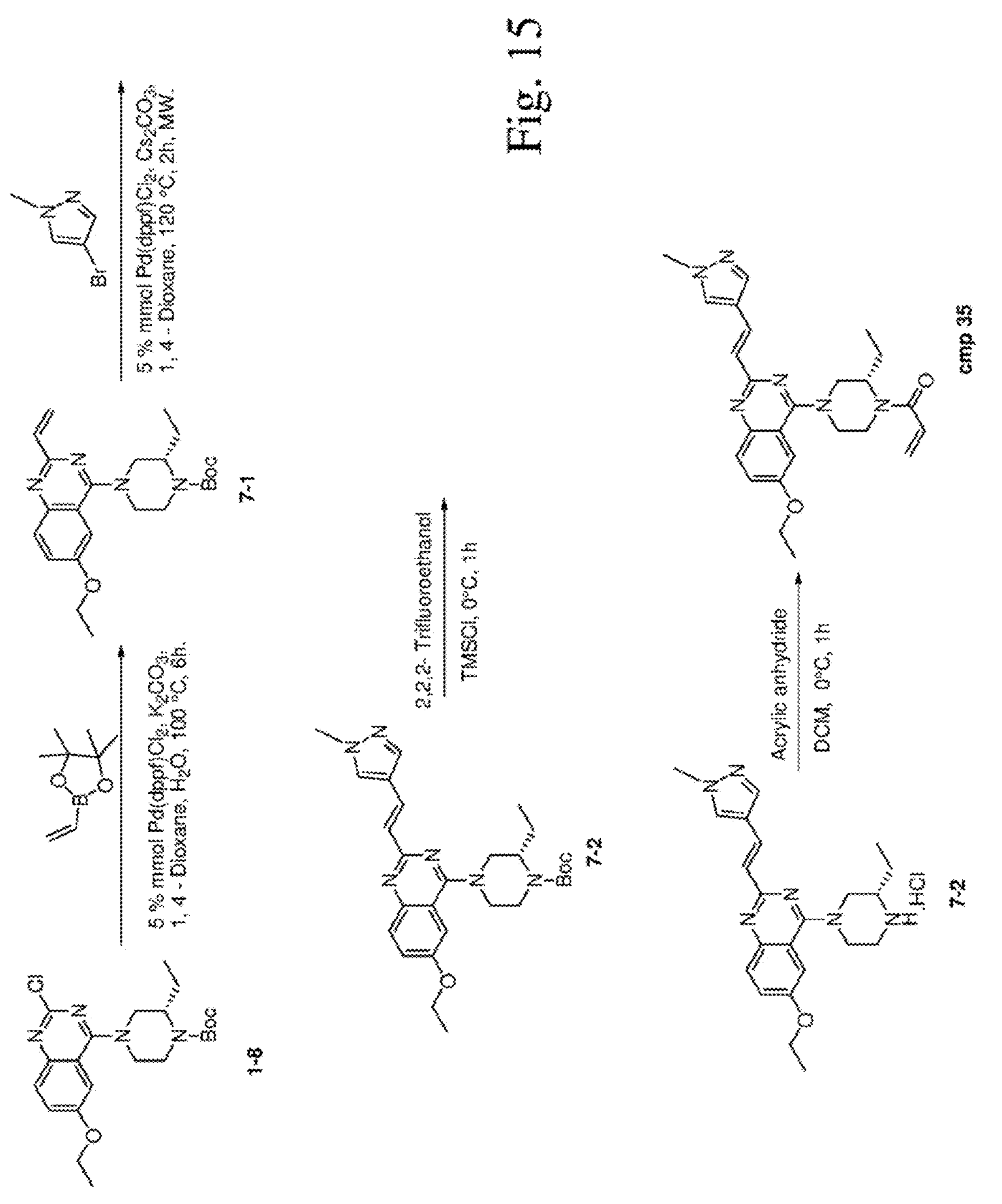
FIG. 15 provides the synthetic scheme for Compound 35.

The synthetic pathway resulting in Compound 35 is shown in FIG. 15

Compound 36 is shown below:

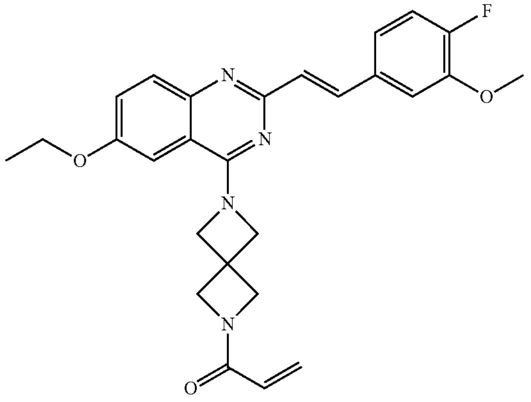 [SMILES: C=CC(=O)N1CC2(C1)CN(c1nc(/C=C/c3ccc(F)c(OC)c3)nc3ccc(OCC)cc13)C2]

Figure 16:
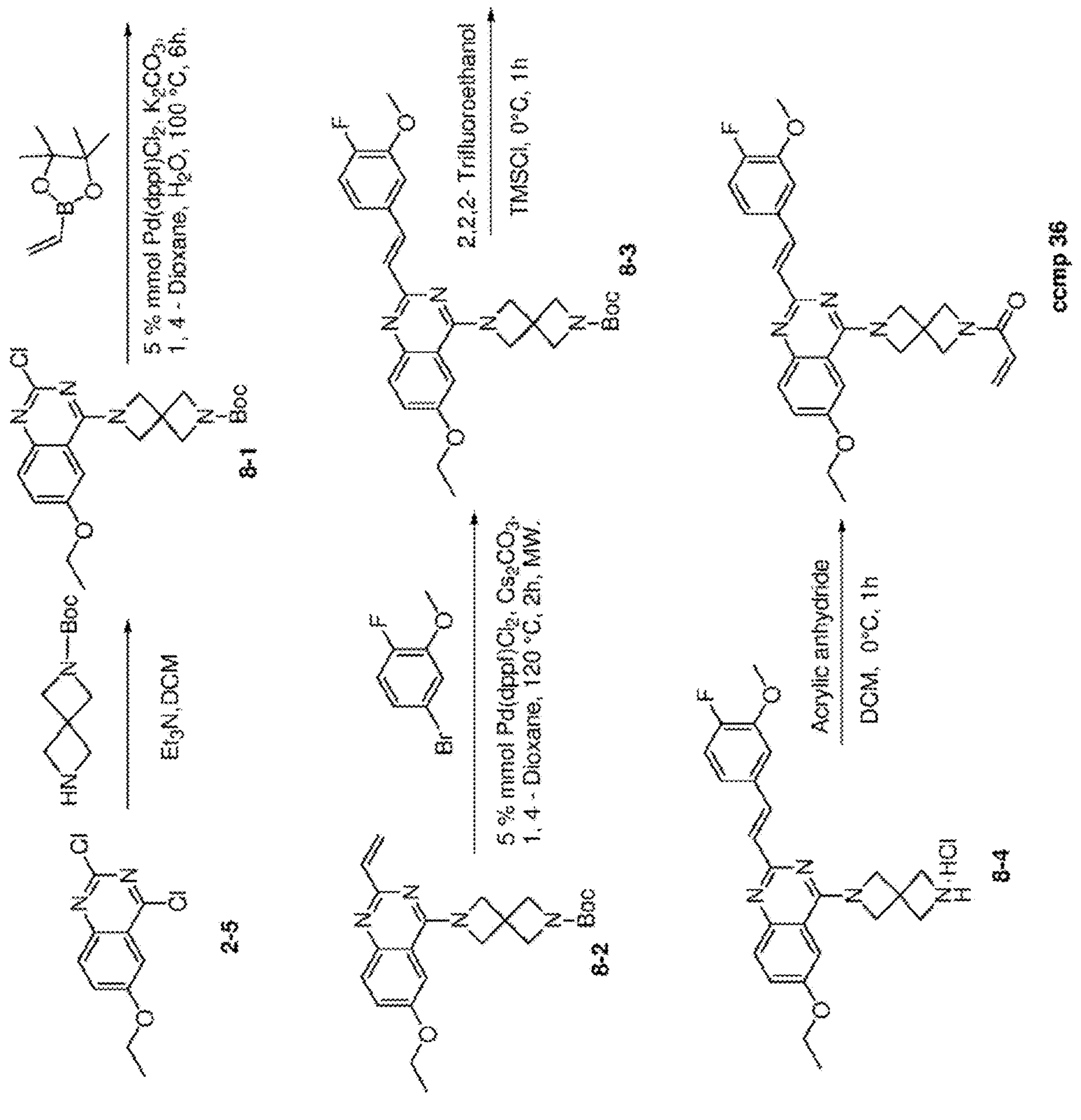
FIG. 16 provides the synthetic scheme for Compound 36.

The synthetic pathway the resulted in Compound 36 is shown in FIG. 16

Compound 37 is shown below:

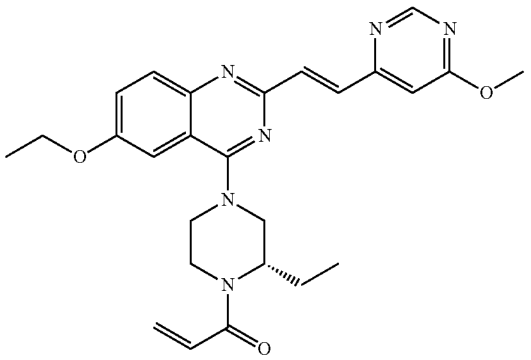 [SMILES: C=CC(=O)N1CCN(c2nc(/C=C/c3cc(OC)ncn3)nc3ccc(OCC)cc23)C[C@@H]1CC]

Figure 17:
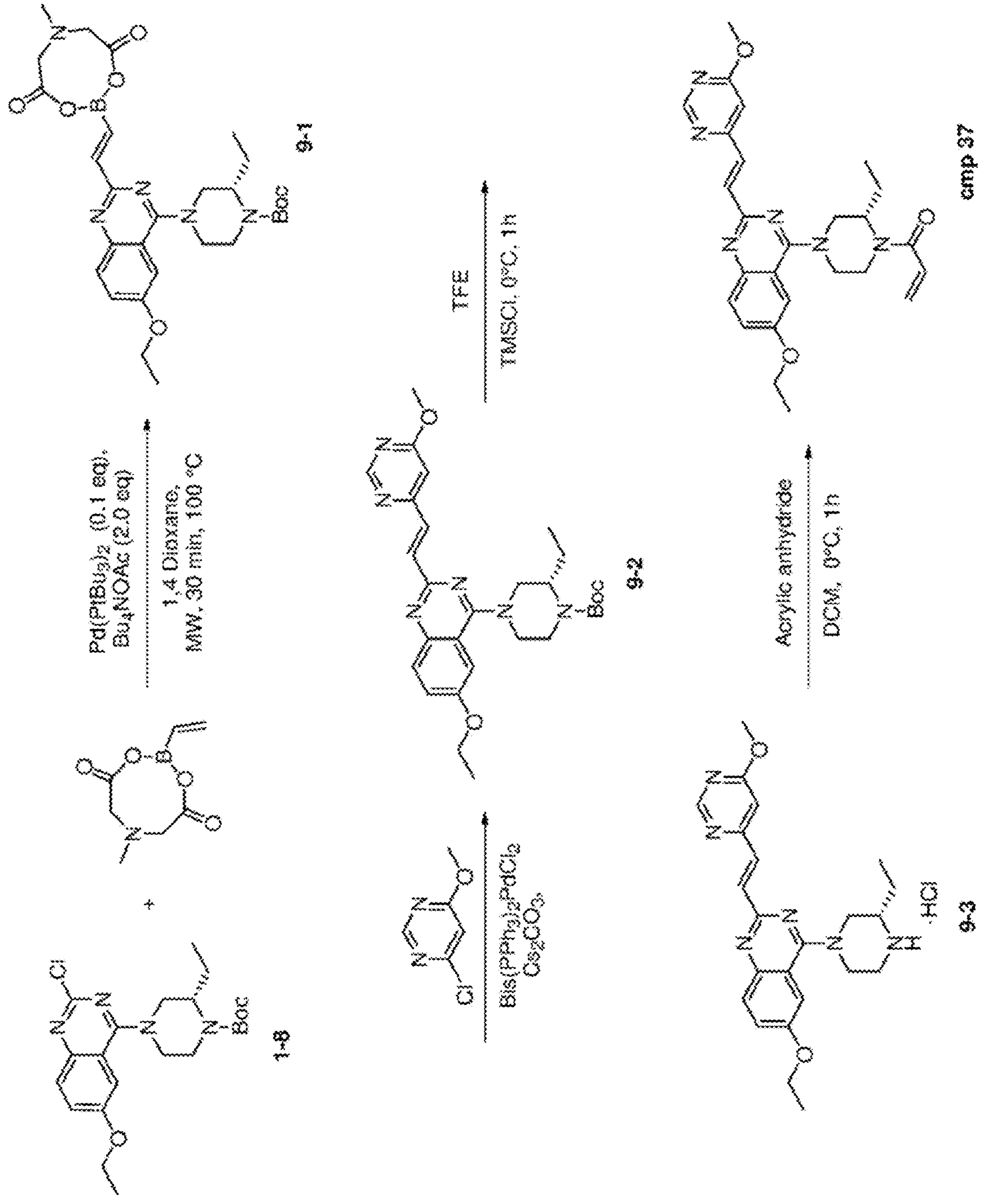
FIG. 17 provides the synthetic scheme for Compound 37.

The synthetic pathway that resulted in Compound 37 is shown FIG. 17.

Compound 38 is shown below:

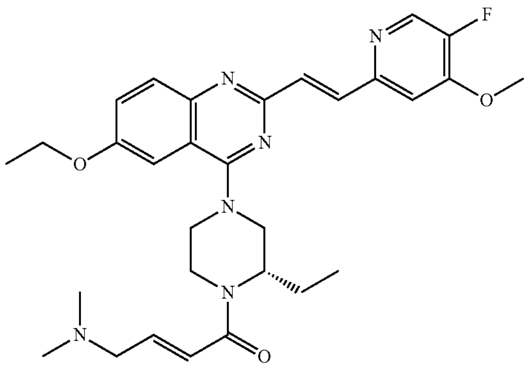 [SMILES: CCOc1ccc2nc(/C=C/c3cc(OC)c(F)cn3)nc(N3CCN(C(=O)/C=C/CN(C)C)[C@@H](CC)C3)c2c1]

Figure 18:
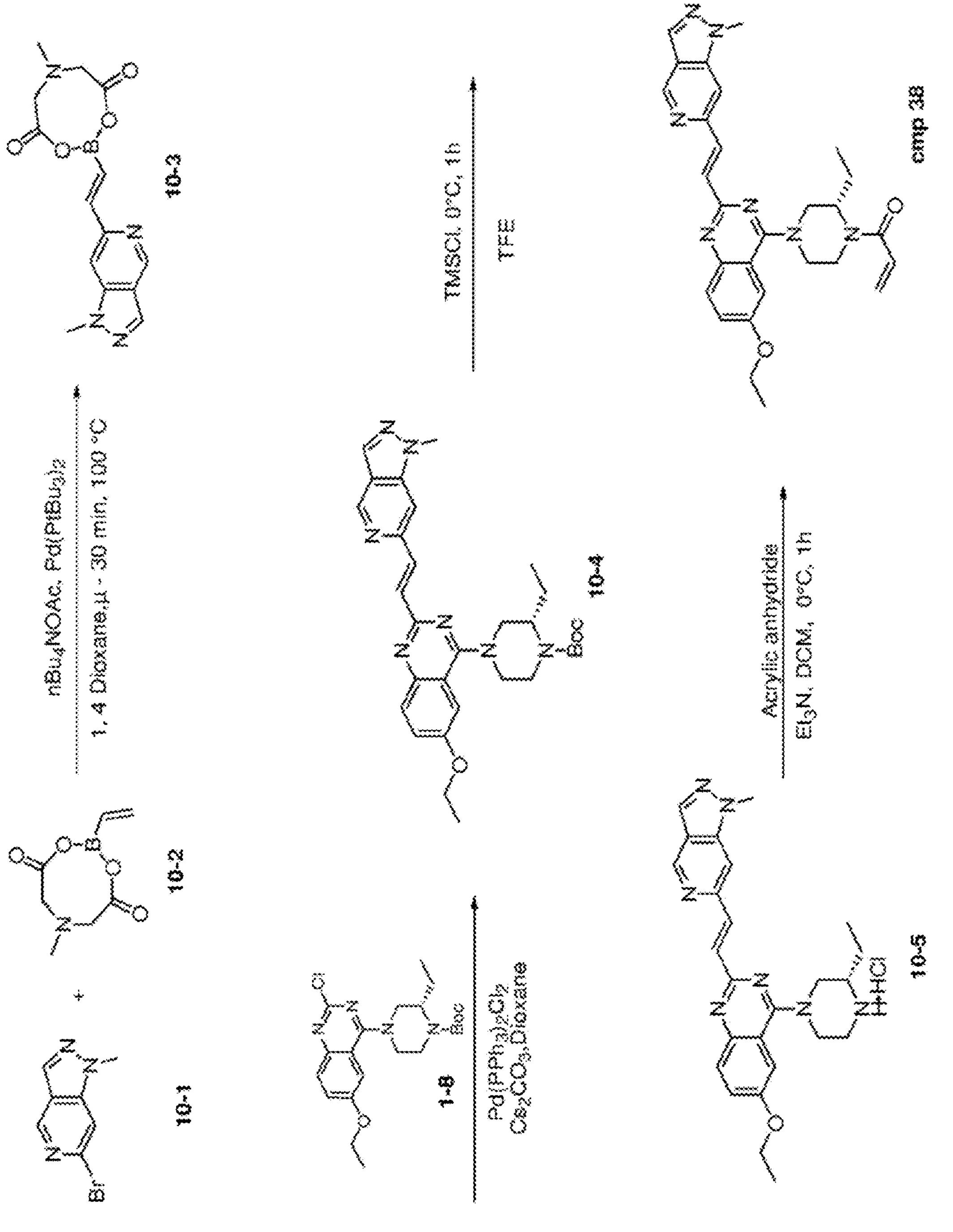
FIG. 18 provides the synthetic scheme for Compound 38.

The synthetic pathway resulting in Compound 38 is shown in FIG. 18

Compounds 39-42 are shown below:

Compound 39

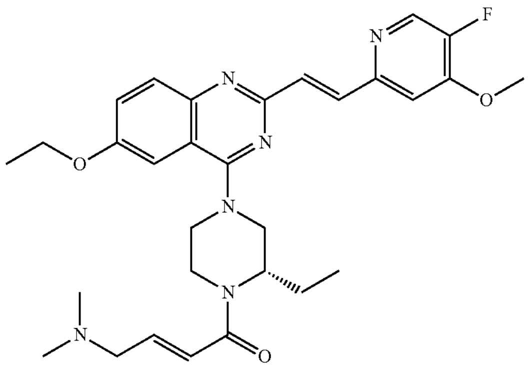

Compound 40

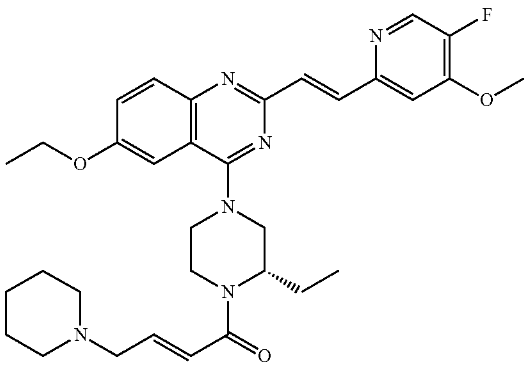

Compound 41

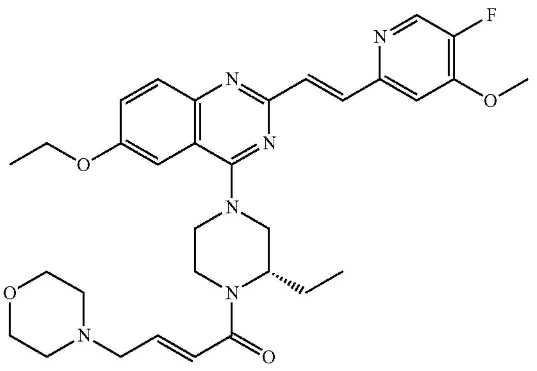

Compound 42

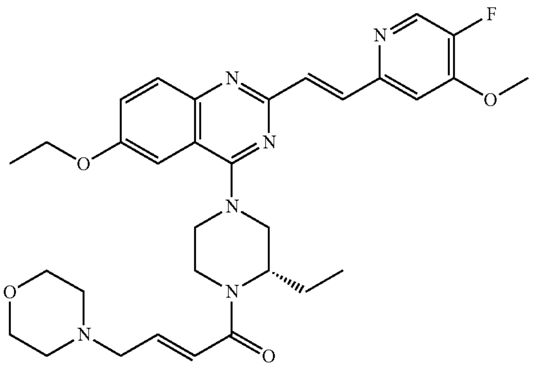

Figure 19:
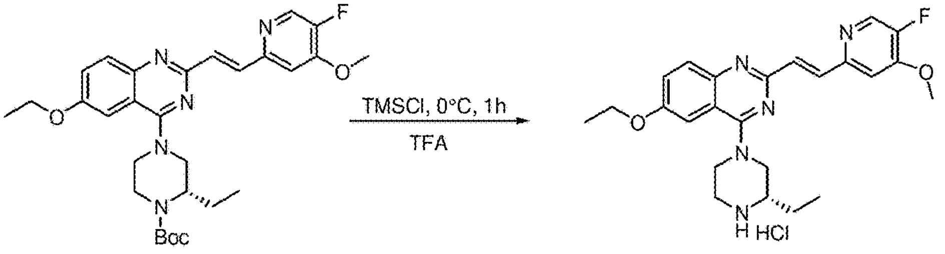
FIG. 19 provides the synthetic scheme for Compounds 39-42.
Figure 19:
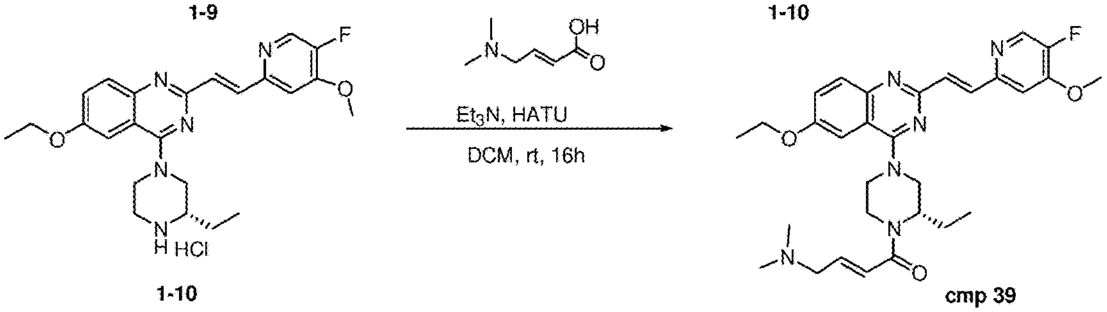
Figure 19:
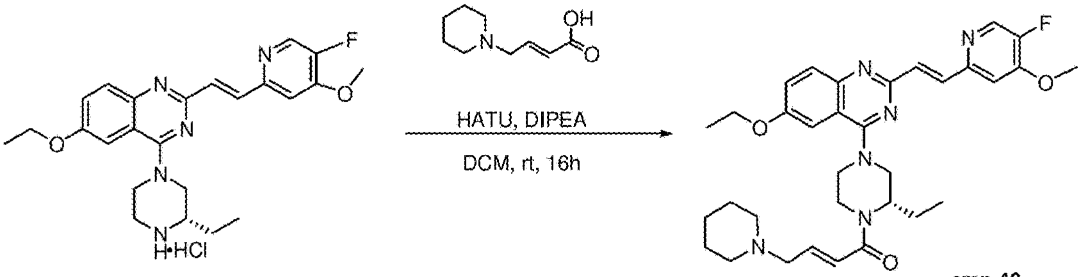
Figure 19:
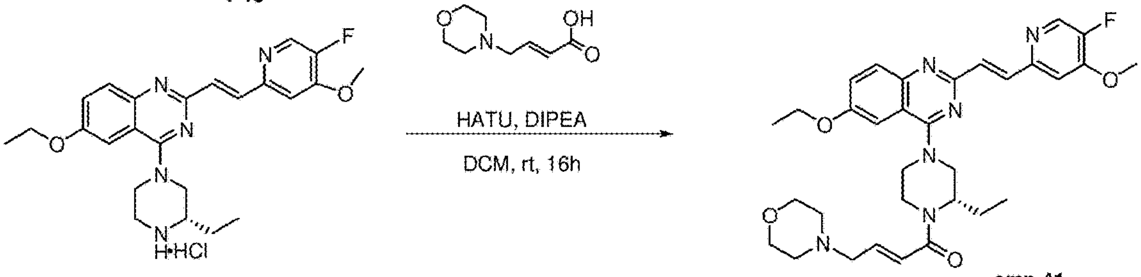
Figure 19:
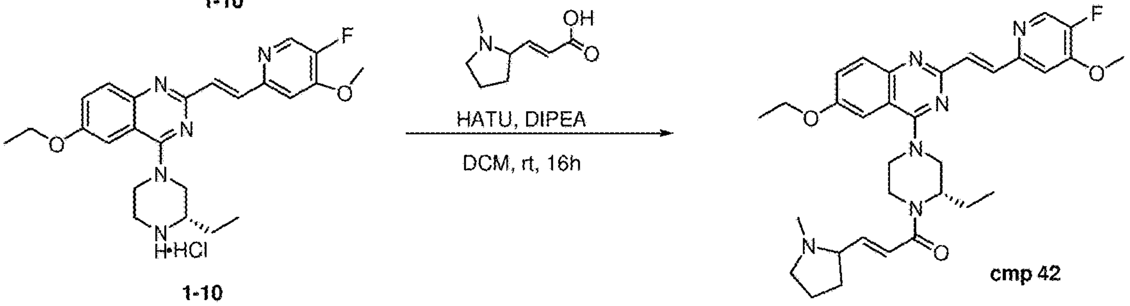

The synthetic scheme resulting in Compounds 39-42 is shown in FIG. 19.

Compound 43 is shown below:

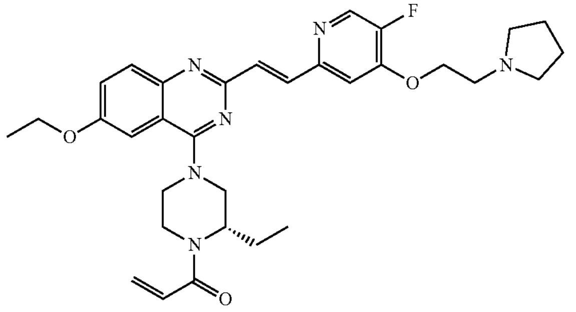

Figure 20:
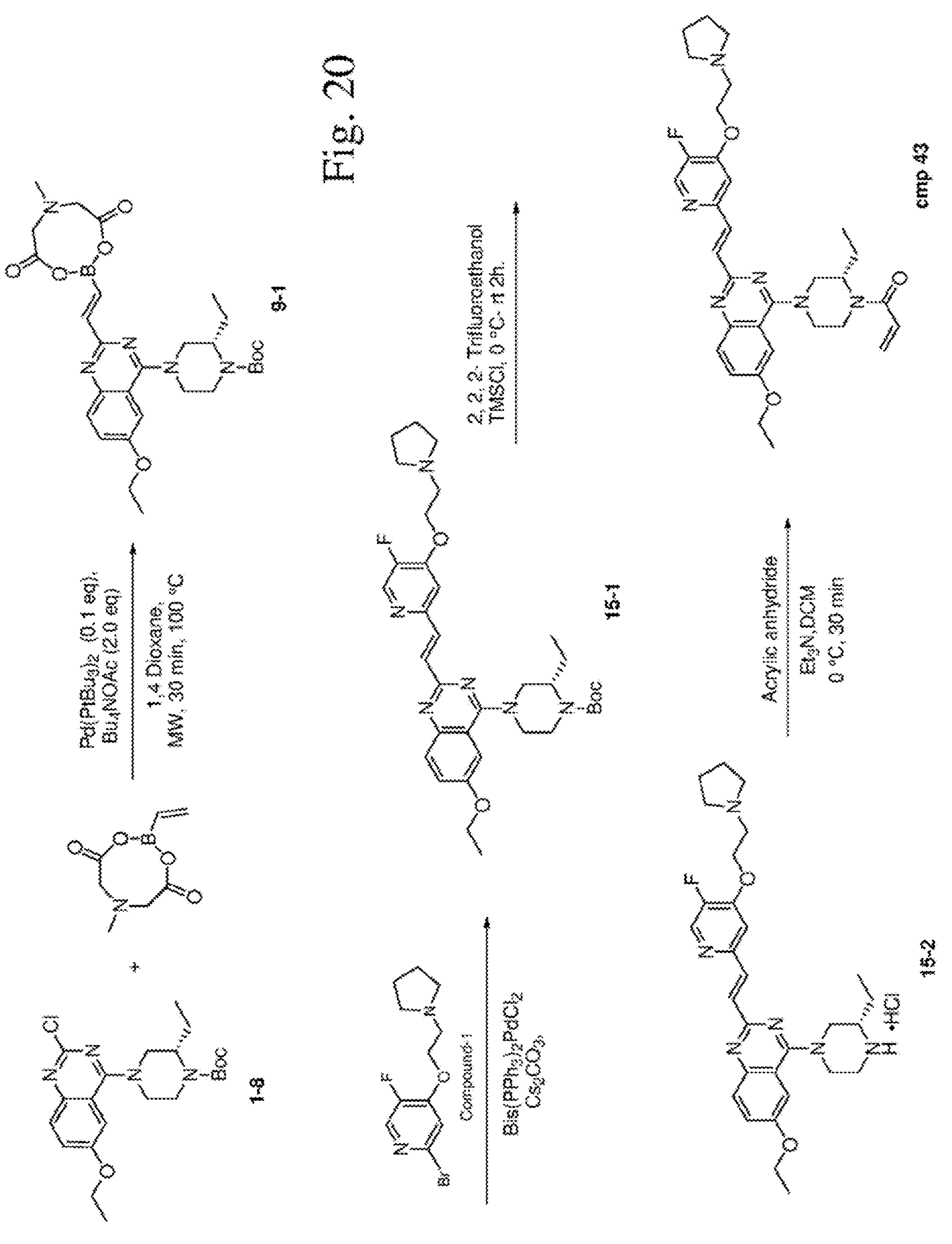
FIG. 20 provides the synthetic scheme for Compound 43.

The synthetic pathway that resulted in Compound 43 is shown in FIG. 20.

Compounds 44 and 45 are shown below:

Compound 44

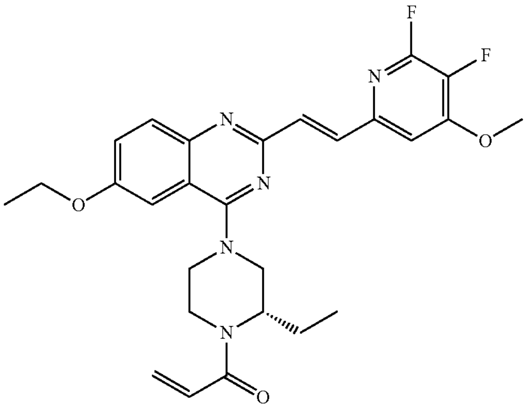

Compound 45

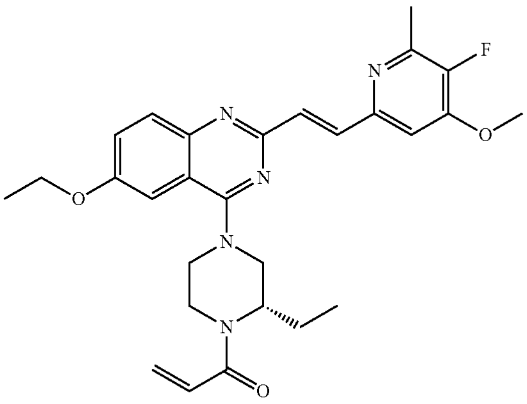

Figure 21:
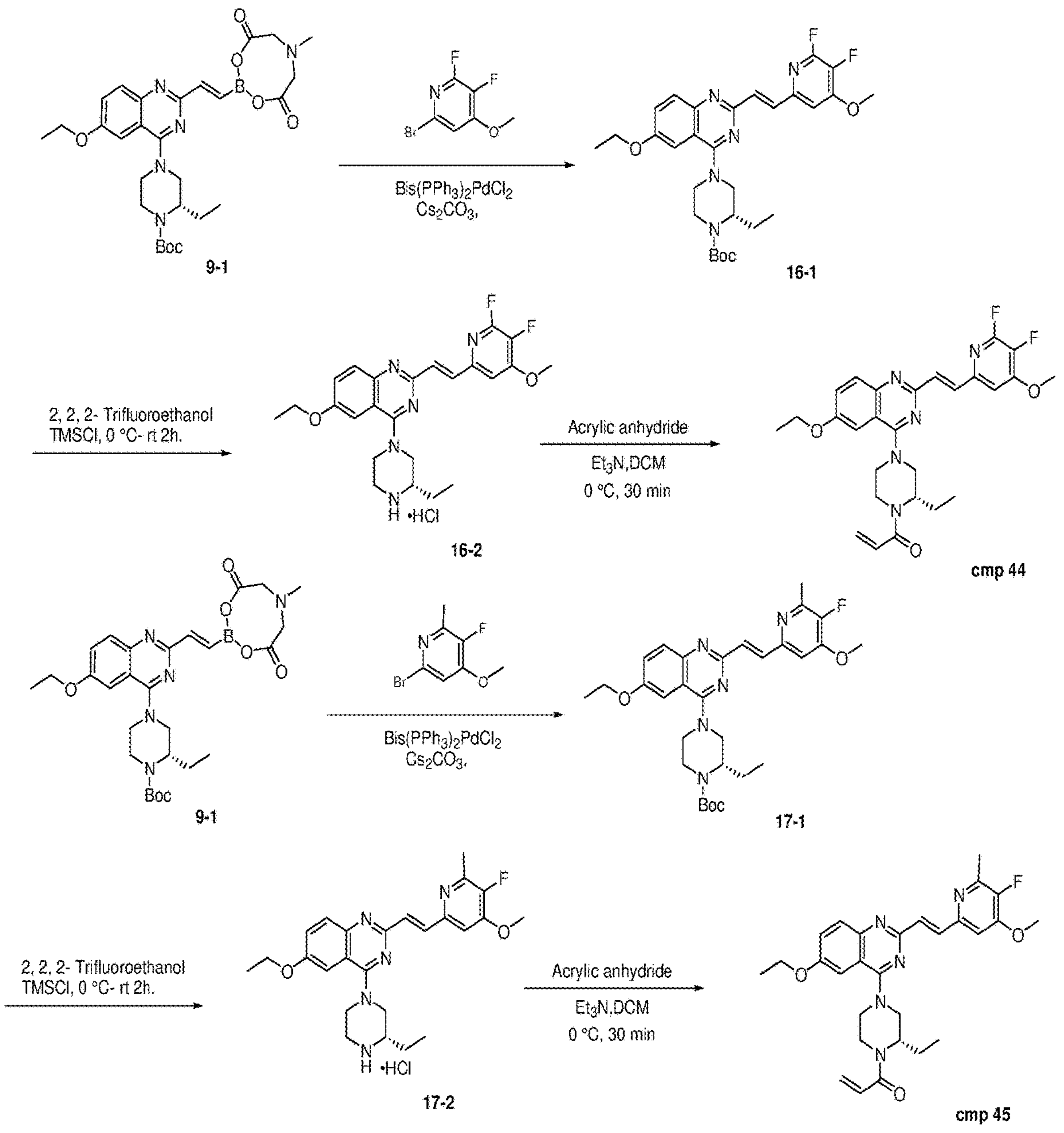
FIG. 21 provides the synthetic scheme for Compounds 44 and 45.

The synthetic scheme resulting in Compounds 44 and 45 is shown in FIG. 21.

Compound 46 is shown below:

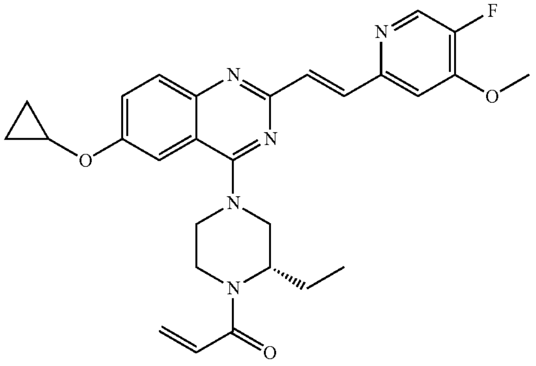 [SMILES: C=CC(=O)N1CCN(c2nc(/C=C/c3cc(OC)c(F)cn3)nc3ccc(OC4CC4)cc23)C[C@@H]1CC]

Figure 22:
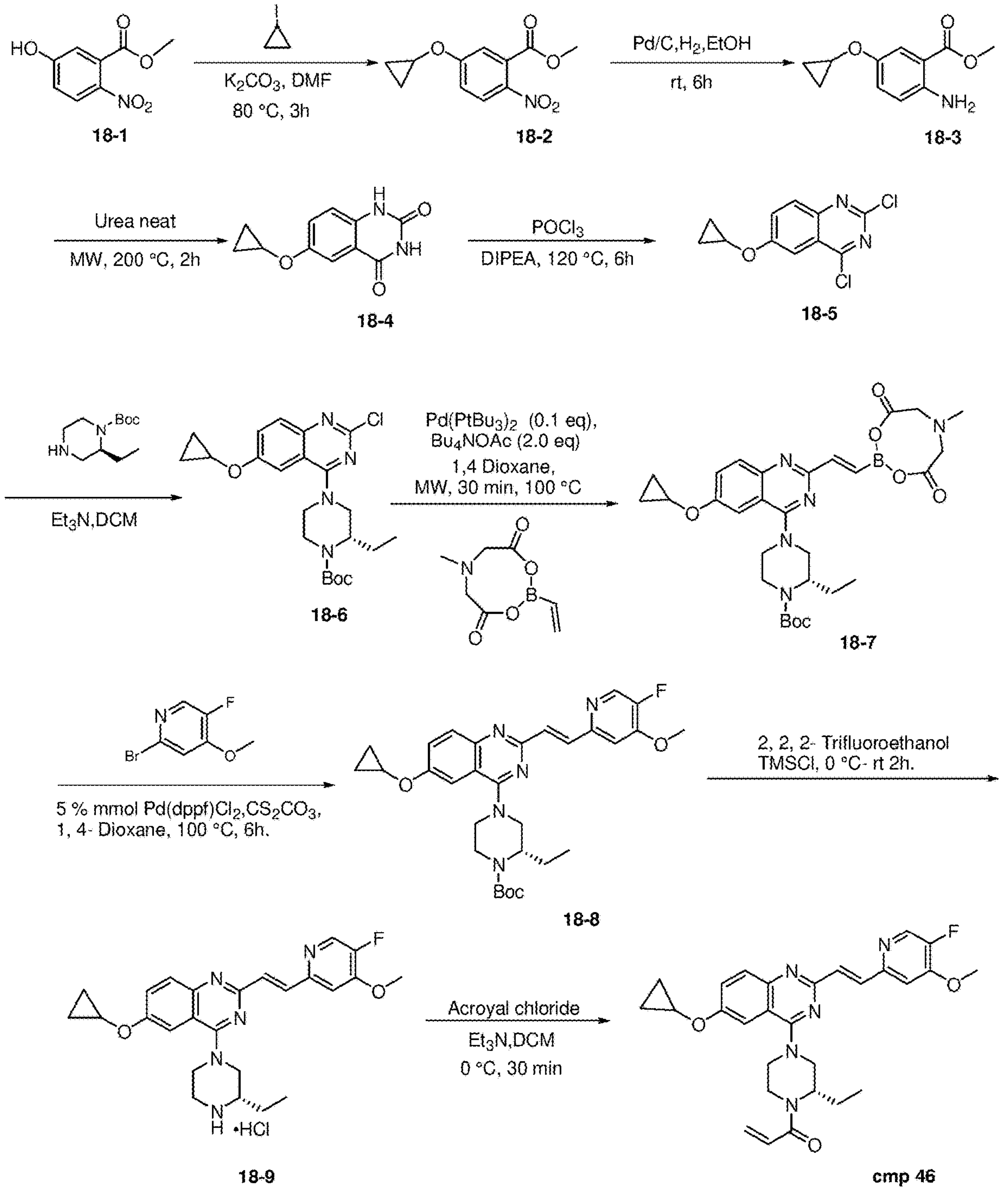
FIG. 22 provides the synthetic scheme for Compound 46.

The synthetic scheme resulting in Compound 46 is shown in FIG. 22.

Compound 47 is shown below:

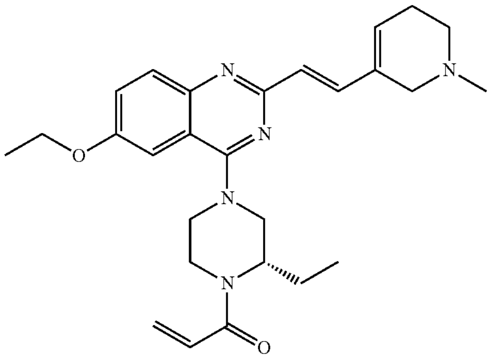 [SMILES: C=CC(=O)N1CCN(c2nc(/C=C/C3=CCCN(C)C3)nc3ccc(OCC)cc23)C[C@@H]1CC]

Figure 23:
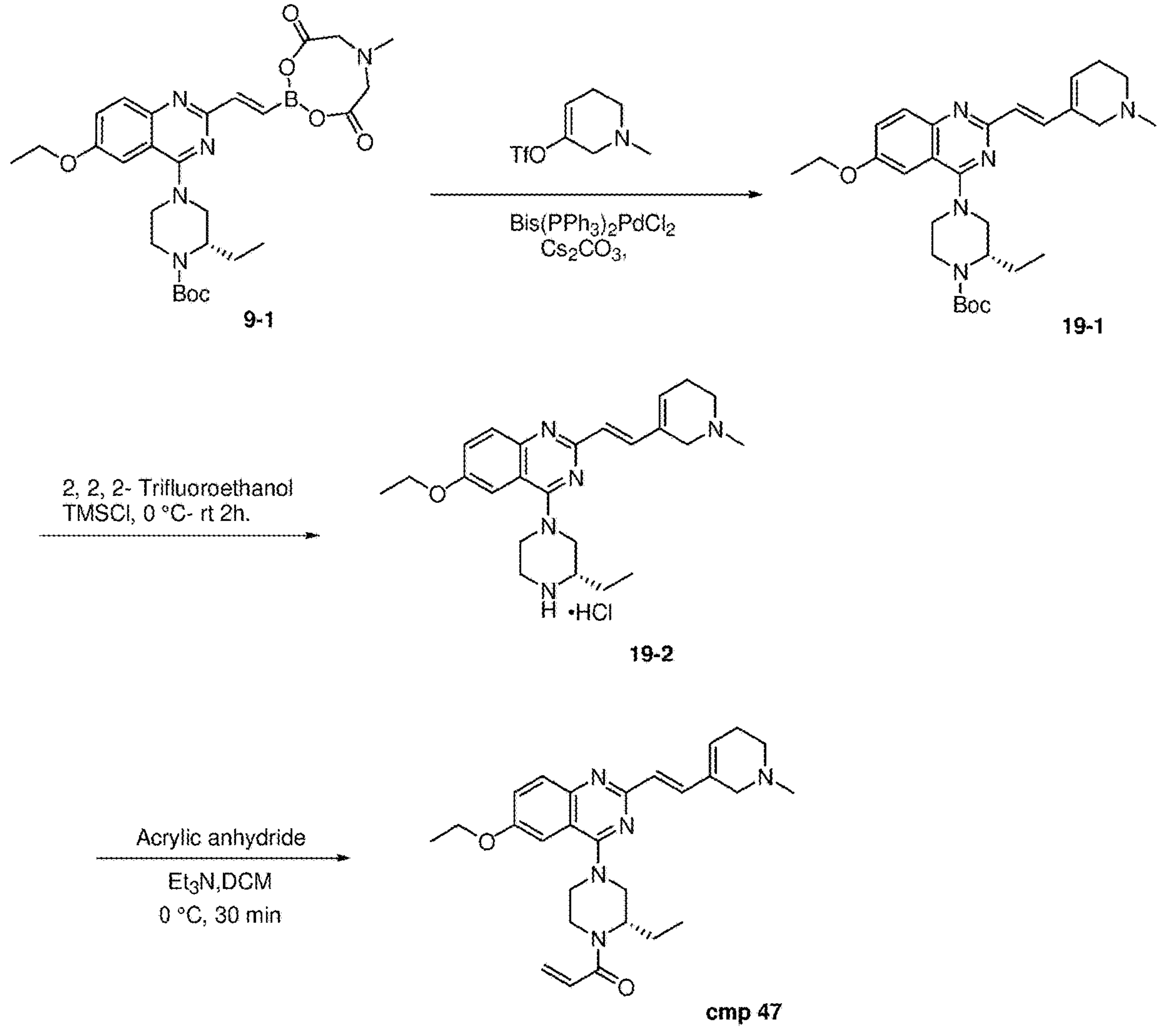
FIG. 23 provides the synthetic scheme for Compound 47.
Figure 24A:
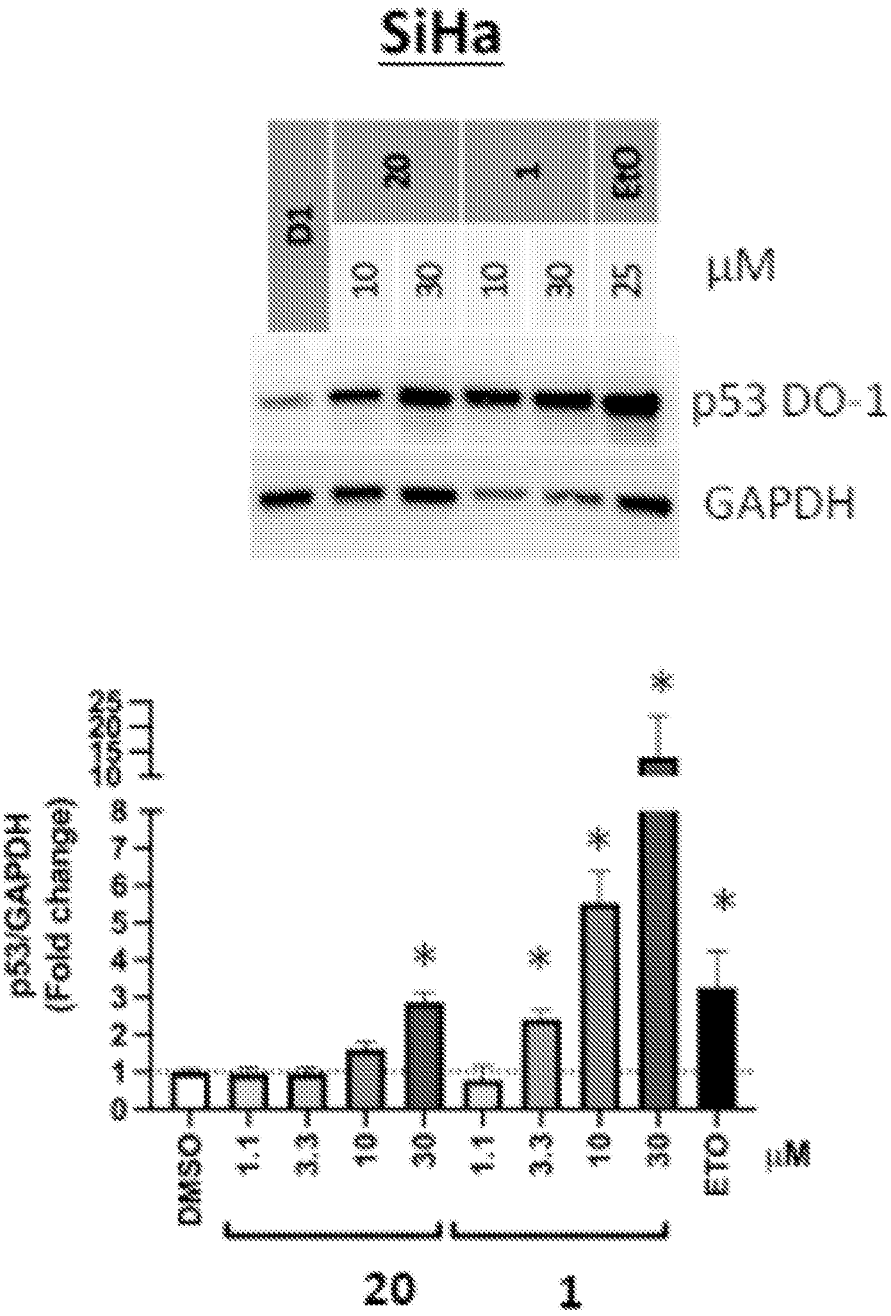
FIGS. 24A and 24B: HPV negative (RPE-1) and HPV positive cervical cancer cell line (SiHa) were incubated with increasing concentrations of 20 or 1 or DMSO (D1; 0.1% v/v) for 48 hrs. Cells were treated with Etoposide (ETO, 25 μM) as a positive control for p53 induction. Cells were lysed, proteins separated by SDS-PAGE and p53, GAPDH protein levels were determined using Immunoblot. Band intensity was measured by densiotmetry and expressed as fold change over DMSO. * indicates a statistical significance of $P<0.05$. Data expressed as S.E.M, n≥3.
Figure 24B:
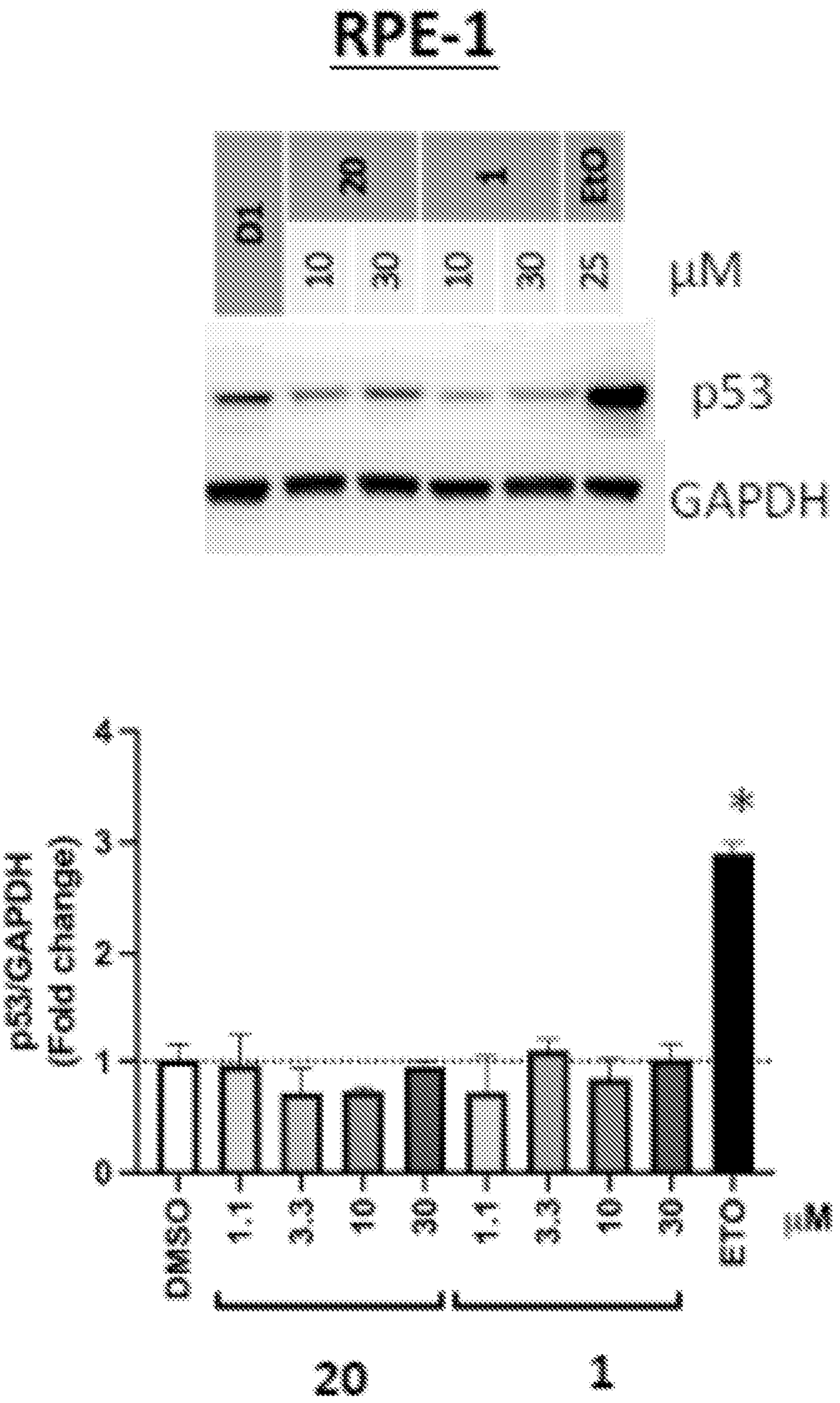
Figure 25A:
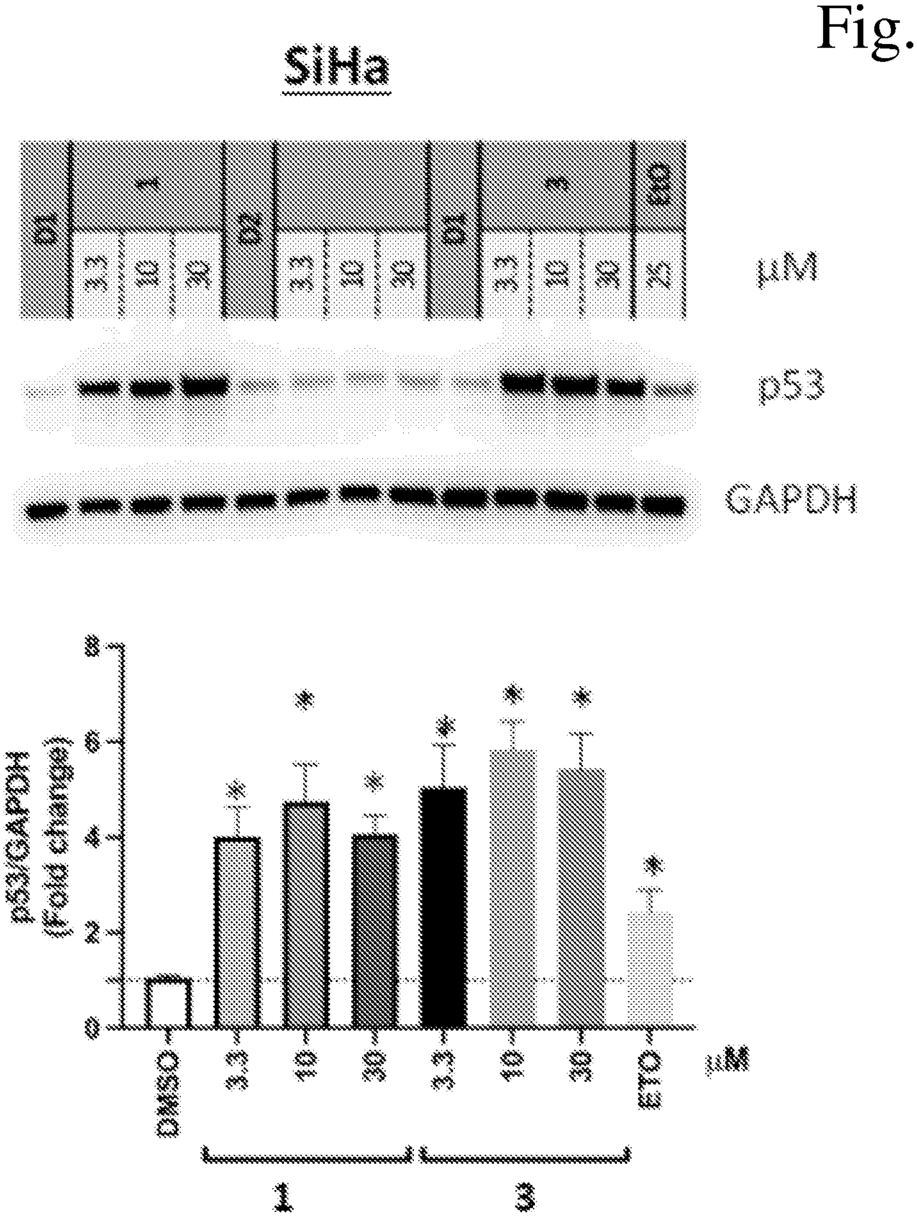
FIGS. 25A and 25B: HPV negative (RPE-1.
Figure 25B:
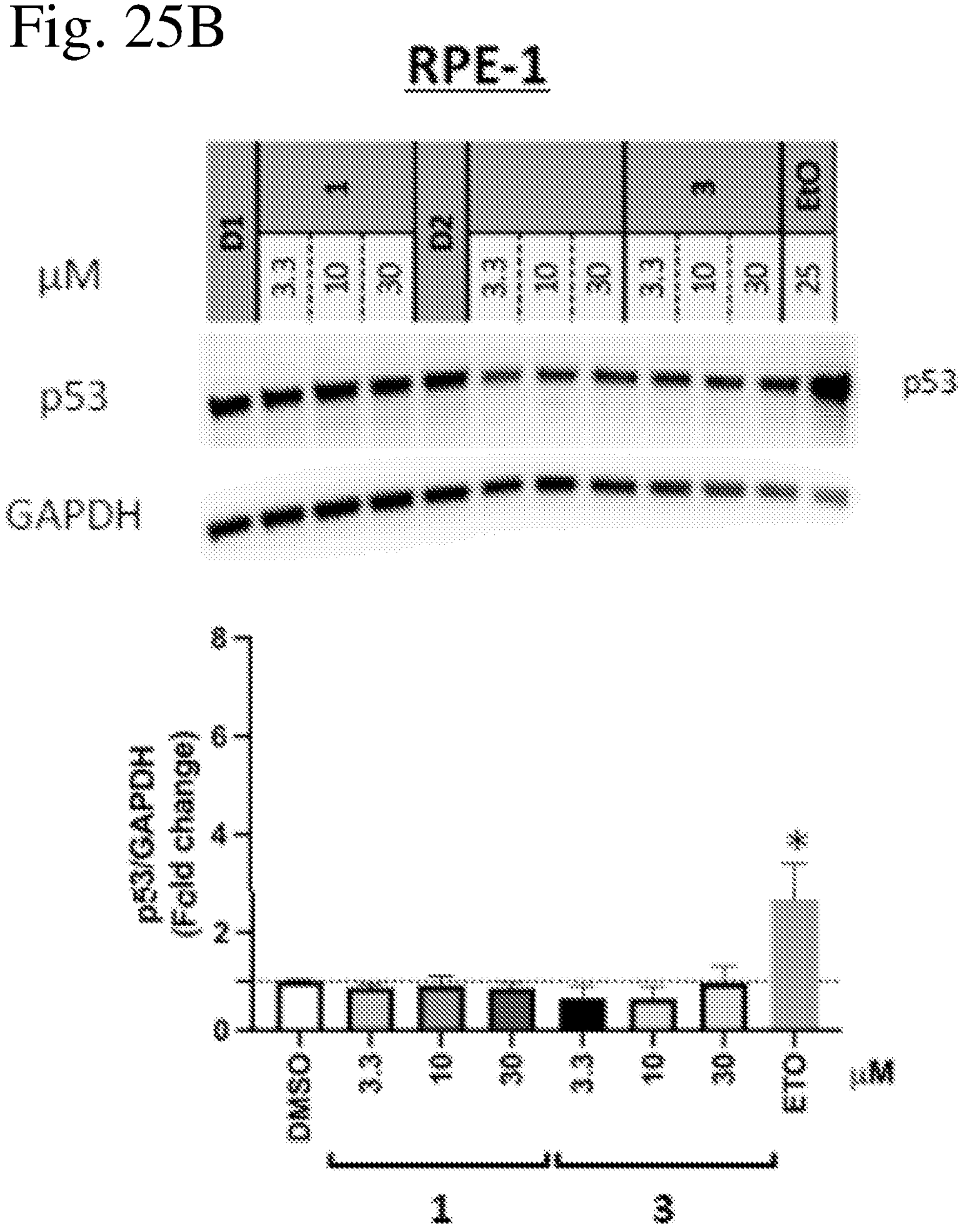
Figure 26A:
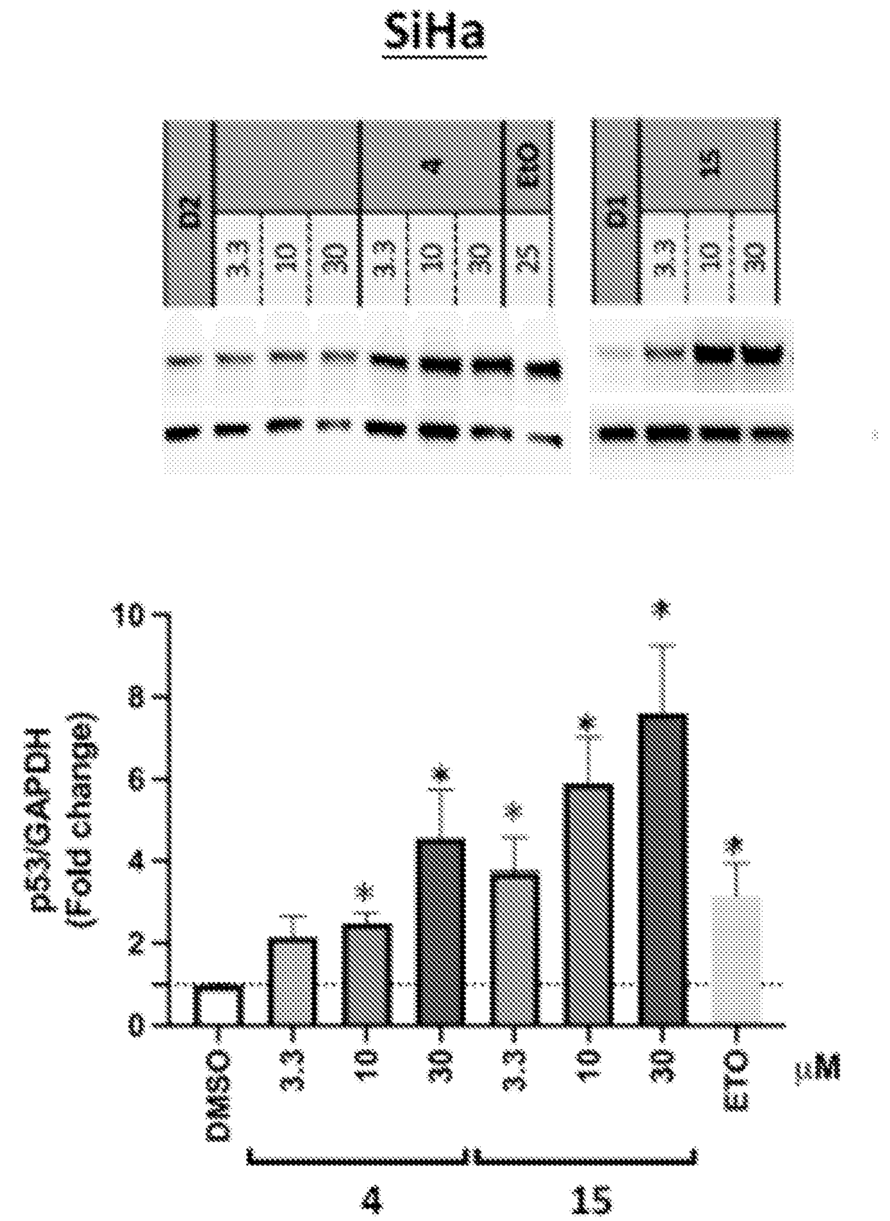
FIG. 26A) and HPV positive cervical cancer cell line (SiHa.
Figure 26B:
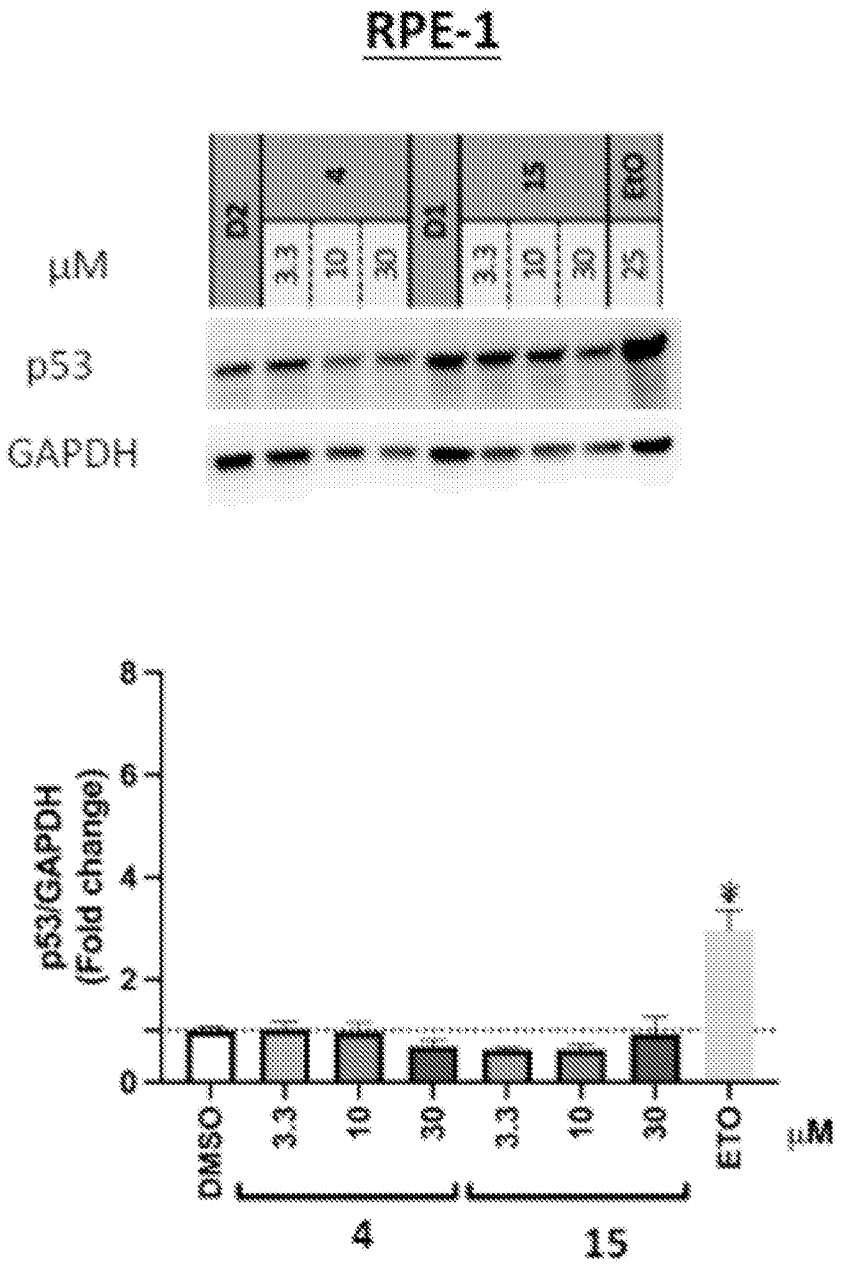
FIG. 26B) were incubated with increasing concentrations of 1 or 3 or DMSO (D1; 0.1% v/v) for 48 hrs. Cells were treated with Etoposide (ETO, 25 μM) as a positive control for p53 induction. Cells were lysed, proteins separated by SDS-PAGE and p53, GAPDH protein levels were determined using Immunoblot. Band intensity was measured by densitometry and expressed as fold change over DMSO. * indicates a statistical significance of $P<0.05$. Data expressed as S.E.M, n≥3.
Figure 27A:
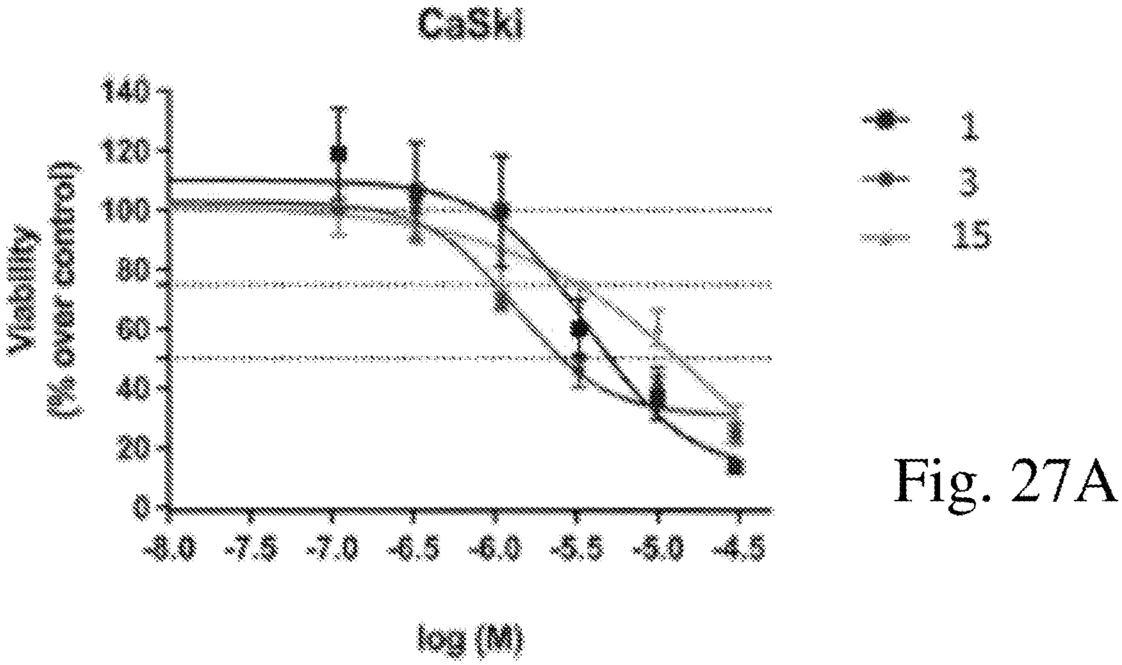
FIGS. 27A-27E: HPV positive cervical (SiHa.
Figure 27B:
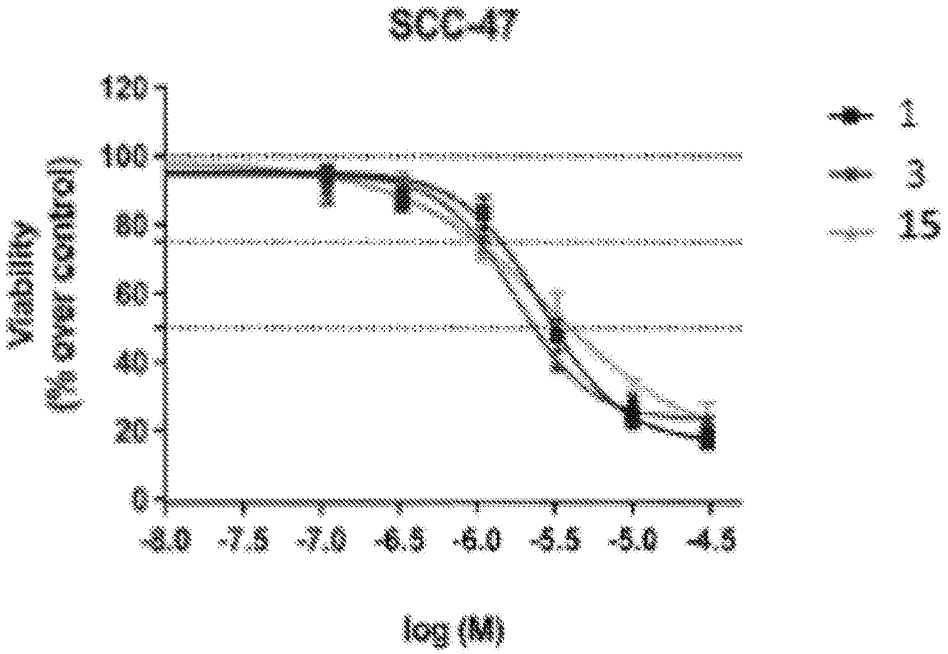
Figure 27C:
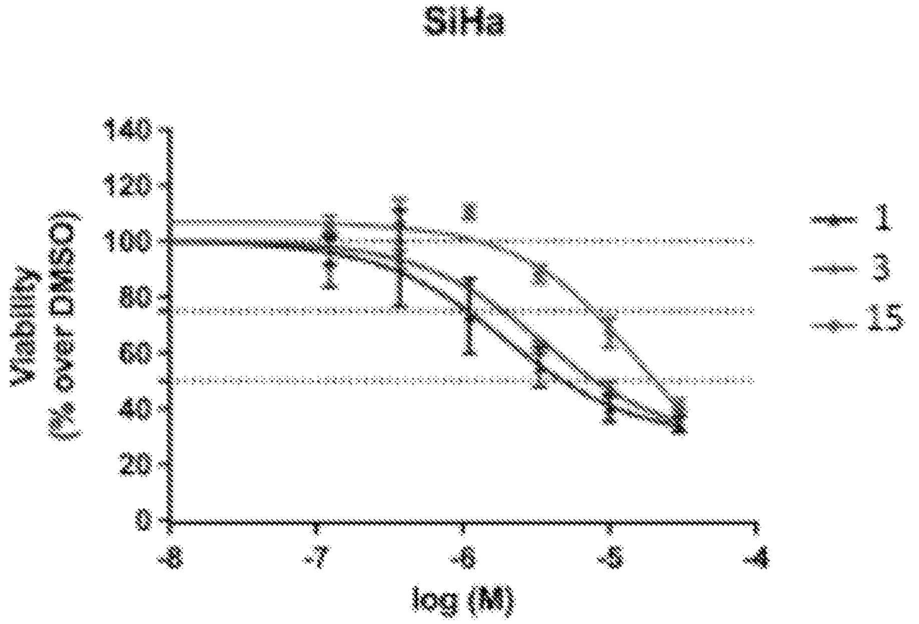
Figure 27D:
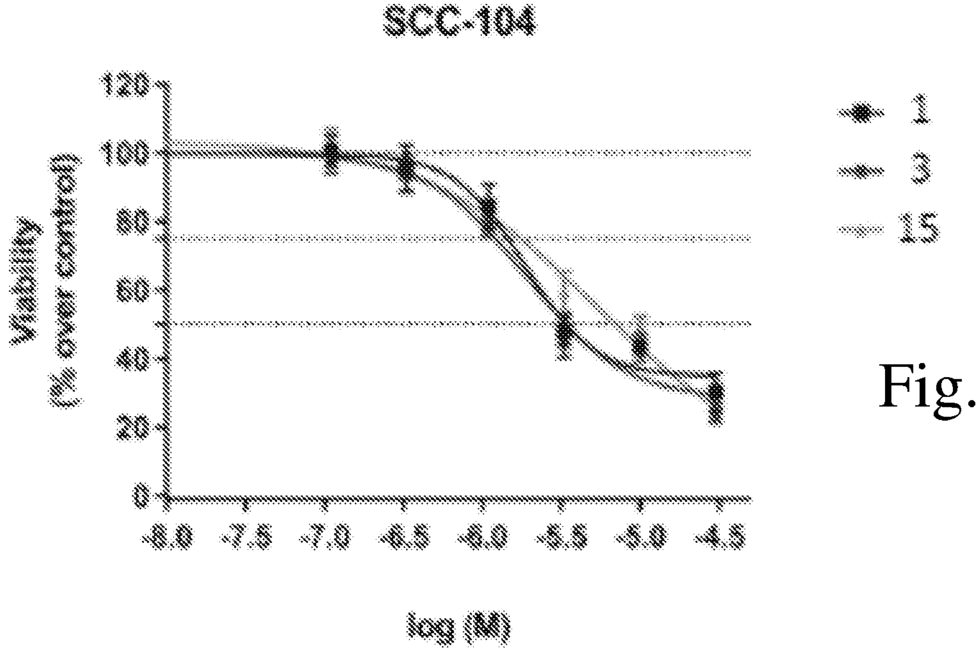
Figure 27E:
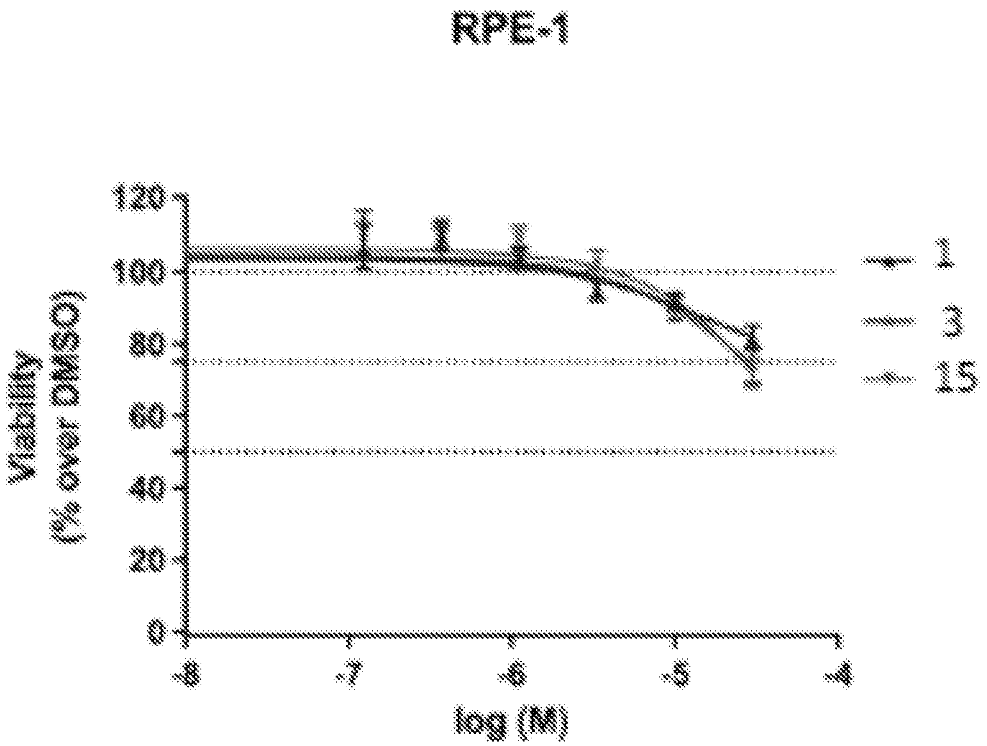

The synthetic scheme that resulted in Compound 47 is shown in FIG. 23.

Pharmaceutical Compositions

For treatment purposes, pharmaceutical compositions comprising the compounds described herein may further comprise one or more pharmaceutically-acceptable excipients. A pharmaceutically-acceptable excipient is a substance that is non-toxic and otherwise biologically suitable for administration to a subject. Such excipients facilitate administration of the compounds described herein and are compatible with the active ingredient. Examples of pharmaceutically-acceptable excipients include stabilizers, lubricants, surfactants, diluents, anti-oxidants, binders, coloring agents, bulking agents, emulsifiers, or taste-modifying agents. In preferred embodiments, pharmaceutical compositions according to the invention are sterile compositions. Pharmaceutical compositions may be prepared using compounding techniques known or that become available to those skilled in the art.

Sterile compositions are also contemplated by the invention, including compositions that are in accord with national and local regulations governing such compositions.

The pharmaceutical compositions and compounds described herein may be formulated as solutions, emulsions, suspensions, or dispersions in suitable pharmaceutical solvents or carriers, or as pills, tablets, lozenges, suppositories, sachets, dragees, granules, powders, powders for reconstitution, or capsules along with solid carriers according to conventional methods known in the art for preparation of various dosage forms. Pharmaceutical compositions of the invention may be administered by a suitable route of delivery, such as oral, parenteral, intravenous, subcutaneous injection, rectal, nasal, topical, or ocular routes, or by inhalation.

In one embodiment, the compositions are formulated for topical administration. For topical applications, the compounds of the present invention are preferably formulated as creams, ointments, lotions, gels, or a similar vehicle suitable for topical administration. For topical administration, the inventive compounds may be mixed with a pharmaceutical carrier at a concentration of about 0.1% to about 10% of drug to vehicle. Another mode of administering the agents of the invention may utilize a patch formulation to effect transdermal delivery.

The pharmaceutical compositions of the present disclosure can be used to ameliorate or prevent the worsening of existing HPV disease symptoms, prevent additional symptoms from occurring, ameliorate or prevent the underlying systemic causes of symptoms, inhibit the disorder or disease, e.g., arresting the development of HPV infection and/or associated symptoms, relieving the disorder or disease, causing regression of the disorder or disease, relieving a condition caused by the disease or disorder, or stopping the symptoms of the disease or disorder.

Exemplary diseases include but are not limited to HPV infections of the vagina, cervix, perineum, rectum, anus, penis, vulva, vagina, skin, and oropharynx. These may be subclinical and detected by ultrasensitive molecular diagnostic tests. Diseases include histologically benign infected epithelium, pre-malignant and dysplastic lesions, carcinoma-in-situ, invasive cancer, and metastatic cancers induced by HPV.

In one embodiment of the present methods, an effective amount of the HPV E6 binding compounds disclosed herein is provided to inhibit the target protein. Measuring such target modulation may be performed by routine analytical methods such as those described below. Such modulation is useful in a variety of settings, including in vitro assays. In such methods, the cell is infected with HPV.

In one embodiment the treatment methods provide an effective amount of one or more of the active compounds disclosed herein sufficient to generally bring about the desired therapeutic benefit in subjects needing such treatment. Effective amounts or doses of the compounds of the invention may be ascertained by routine methods, such as modeling, dose escalation, or clinical trials, taking into account routine factors, e.g., the mode or route of administration or drug delivery, the pharmacokinetics of the agent, the severity and course of the infection, the subject's health status, condition, and weight, and the judgment of the treating physician. An exemplary dose is in the range of about from about 0.1 mg to 1 g daily, or about 1 mg to 50 mg daily, or about 50 to 250 mg daily, or about 250 mg to 1 g daily. The total dosage may be given in single or divided dosage units (e.g., BID, TID, QID). An exemplary dose for topical administration may be in a formulation with 0.01%-10% of the E6 inhibitory compound.

The invention claimed is:

1. A compound of Formula III:

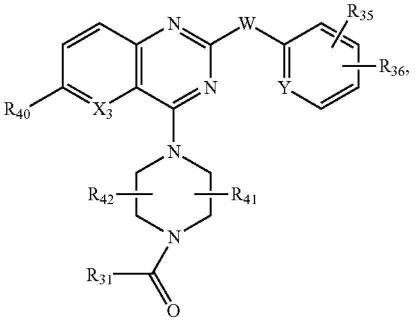

or a pharmaceutically acceptable salt thereof, wherein:

Y is CH or N;

$X_3$ is CH or N;

W is $-(CH_2)_n-$ or $-CH{=}CH-$;

$R_{31}$ is $-CH{=}CH_2$, $-CR_{51}{=}CH_2$, $-CH{=}CHCH_2N(CH_3)_2$, $-CH{=}CHCH_3$, $-CH_2$(halo), or $-CH_3$, wherein $R_{51}$ is H or halo;

$R_{35}$ is H or halo;

$R_{36}$ is H, halo, $-OCH_3$, $-OCH_2CH_3$, $-OCH_2CH_2OCH_3$, $-OCH_2CH_2-$N-pyrrolidine, or $-CONHCH_3$;

$R_{40}$ is H, $-OCH_3$, $-OCH_2CH_3$, or $-OCH_2CH_2OCH_3$;

$R_{41}$ is H or $-C_1$-$C_4$ alkyl;

$R_{42}$ is H, $-CN$, or $-C_1$-$C_4$ alkyl, or $R_{41}$ and $R_{42}$ together with the atoms to which they are attached form a 3- to 6-membered heterocycloalkyl ring; and n is 2, 3, or 4.

2. The compound of claim 1, wherein W is

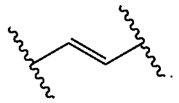 [SMILES: */C=C/*]

3. The compound of claim 1, wherein $X_3$ is CH.

4. The compound of claim 1, wherein Y is N.

5. The compound of claim 1, wherein $R_{31}$ is $-CH{=}CH_2$, $-CH{=}CHCH_2N(CH_3)_2$, or $-CH{=}CHCH_3$.

6. The compound of claim 5, wherein $R_{31}$ is $-CH{=}CH_2$.

7. The compound of claim 1, wherein $R_{35}$ is H or F.

8. The compound of claim 7, wherein $R_{36}$ is $-OCH_3$, $-OCH_2CH_3$, or $-OCH_2CH_2OCH_3$.

9. The compound of claim 1, wherein $R_{40}$ is $-OCH_3$ or $-OCH_2CH_3$.

10. The compound of claim 1, wherein $R_{41}$ is H.

11. The compound of claim 8, wherein $R_{42}$ is $-C_1$-$C_4$ alkyl.

12. The compound of claim 1, wherein $R_{41}$ and $R_{42}$ together with the atoms to which they are attached form a 4- to 6-membered heterocycloalkyl ring.

13. The compound of claim 1, wherein $X_3$ is CH, Y is CH, and W is

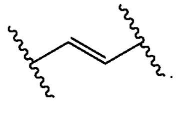 [SMILES: */C=C/*]

14. The compound of claim 13, wherein $R_{31}$ is $—CH{=}CH_2$, $—CH{=}CHCH_2N(CH_3)_2$, or $—CH{=}CHCH_3$.

15. The compound of claim 14, wherein $R_{35}$ is H or F.

16. The compound of claim 15, wherein $R_{36}$ is $—OCH_3$, $—OCH_2CH_3$, or $—OCH_2CH_2OCH_3$.

17. The compound of claim 16, wherein $R_{40}$ is $—OCH_3$ or $—OCH_2CH_3$.

18. The compound of claim 17, wherein $R_{41}$ is H.

19. The compound of claim 18, wherein $R_{42}$ is $—C_1$-$C_4$ alkyl.

20. The compound of claim 1, wherein $X_3$ is CH, Y is N, and W is

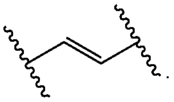

21. The compound of claim 20, wherein $R_{31}$ is $—CH{=}CH_2$, or $—CH{=}CHCH_2N(CH_3)_2$, $—CH{=}CHCH_3$.

22. The compound of claim 21, wherein $R_{35}$ is H or F.

23. The compound of claim 22, wherein $R_{36}$ is $—OCH_3$, $—OCH_2CH_3$, or $—OCH_2CH_2OCH_3$.

24. The compound of claim 23, wherein $R_{40}$ is $—OCH_3$ or $—OCH_2CH_3$.

25. The compound of claim 24, wherein $R_{41}$ is H.

26. The compound of claim 25, wherein $R_{42}$ is $—C_1$-$C_4$ alkyl.

27. The compound of claim 1, wherein the compound of Formula III has the structure:

1

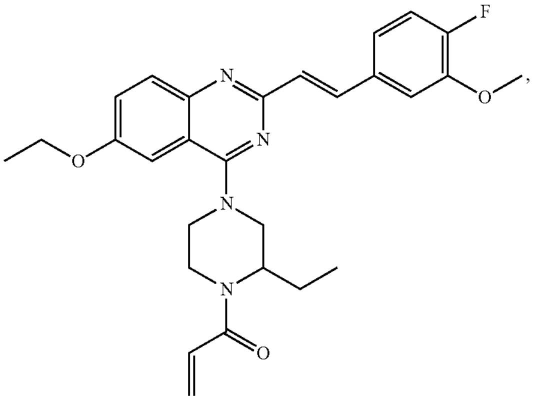

2

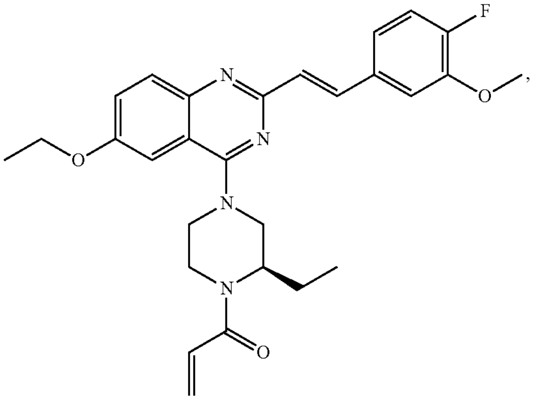

-continued

3

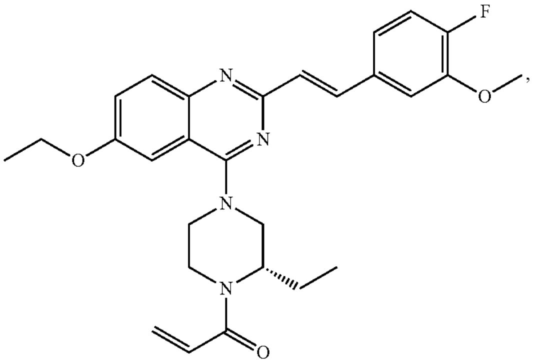

4

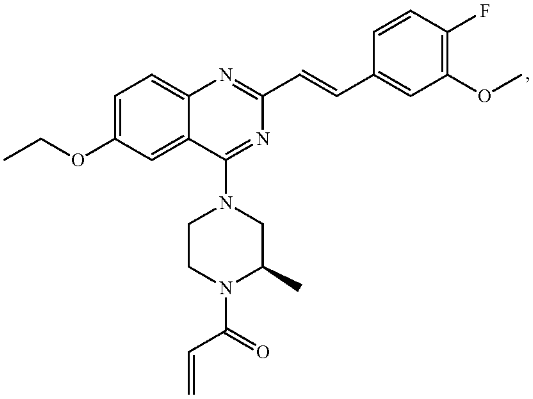

5

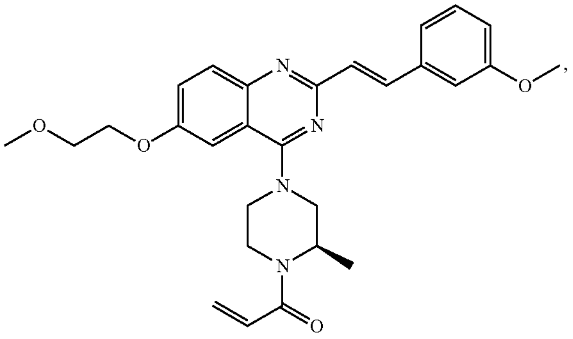

6

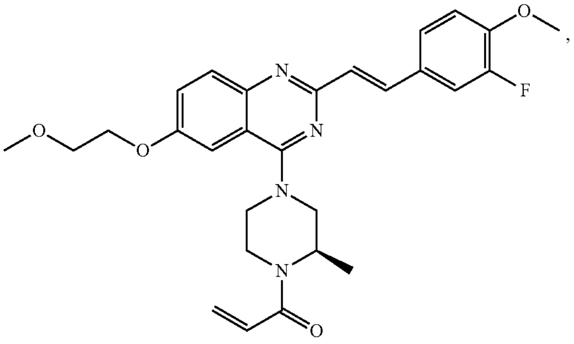

-continued
8
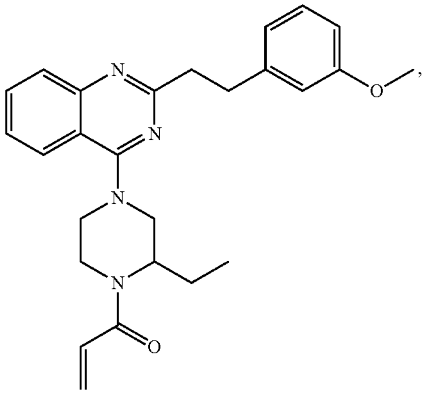,
9
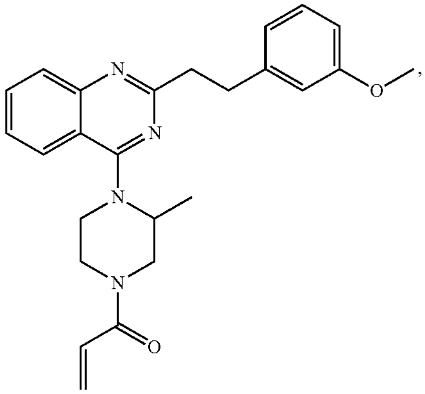,
12
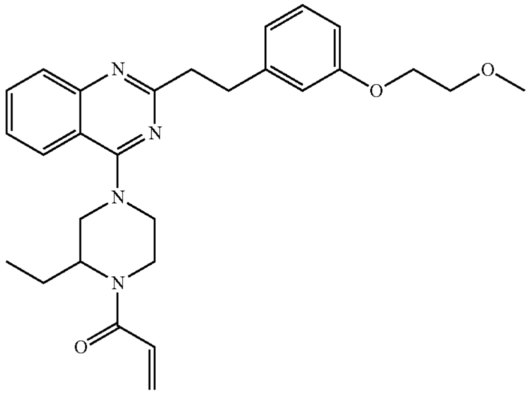,
13
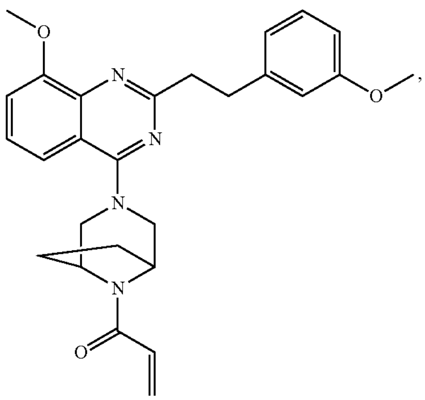,
-continued
14
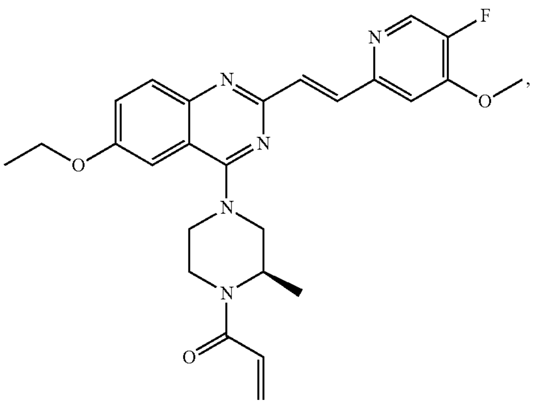,
15
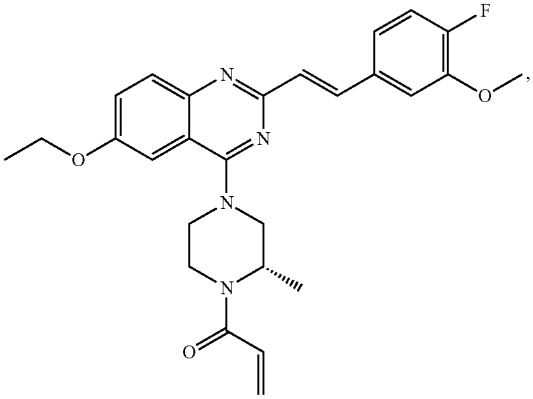,
16
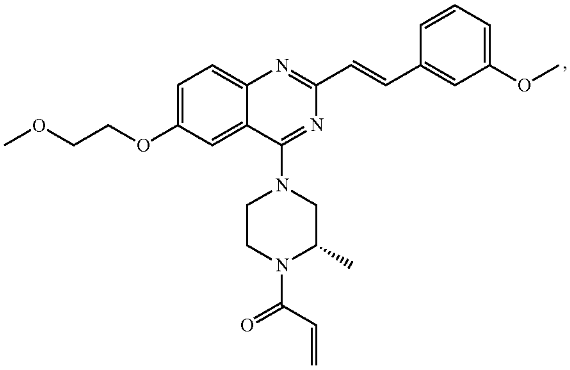,
17
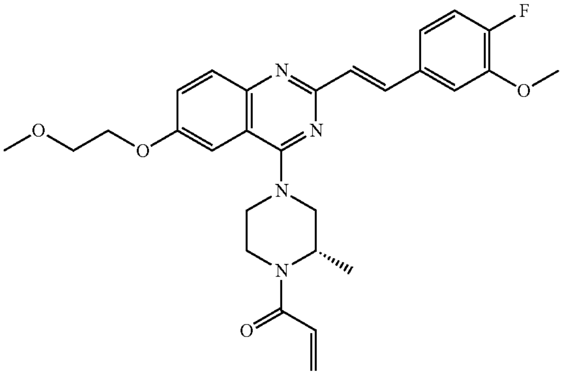, -continued
18
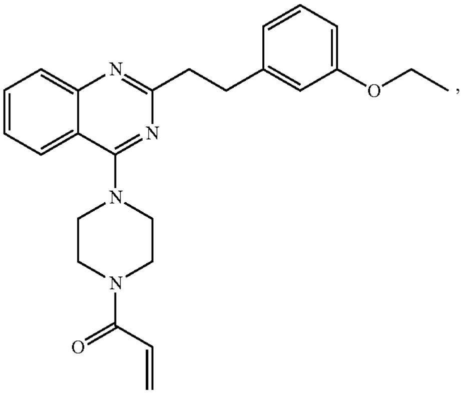
19
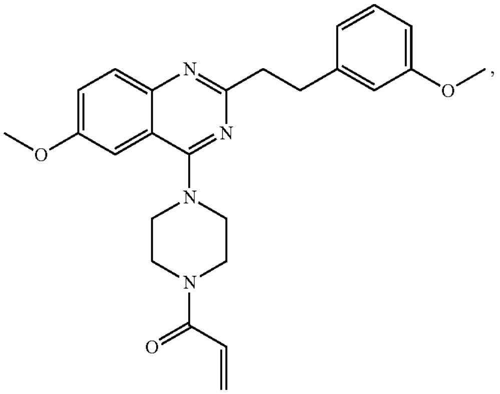
20
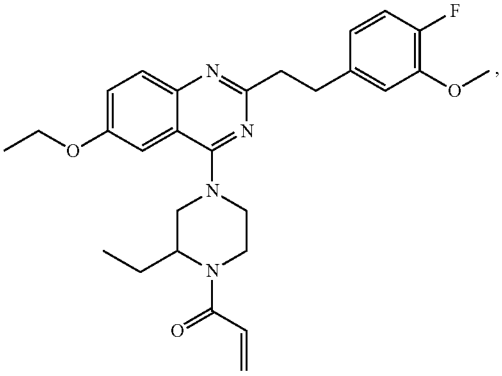
29
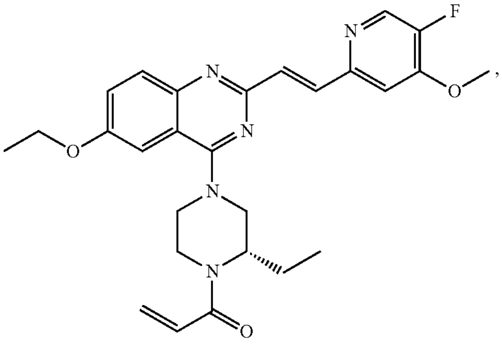
-continued
30
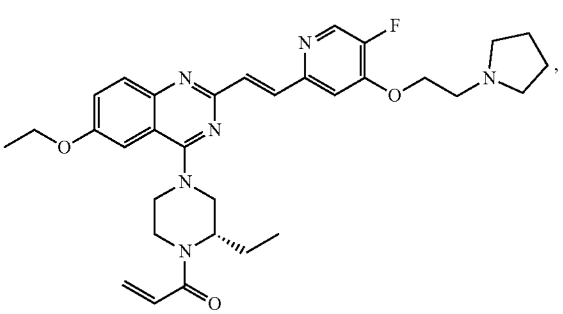
31
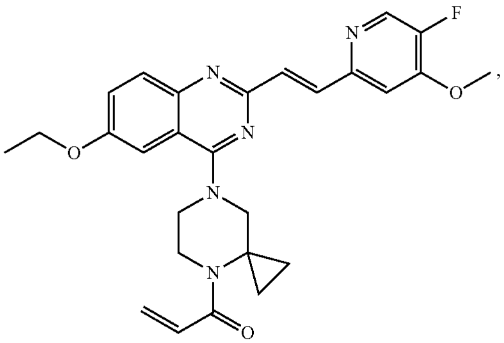
32
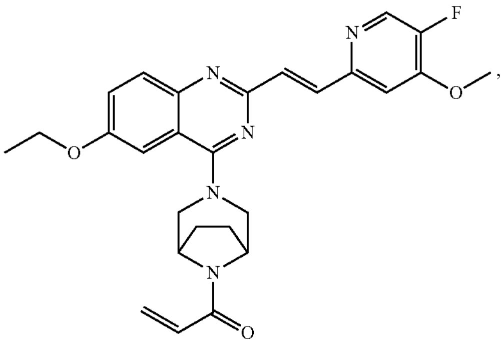
33
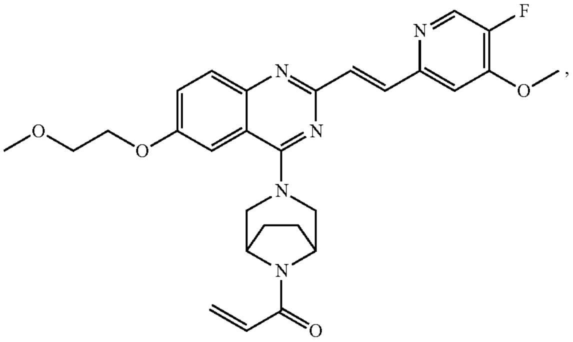

-continued
34
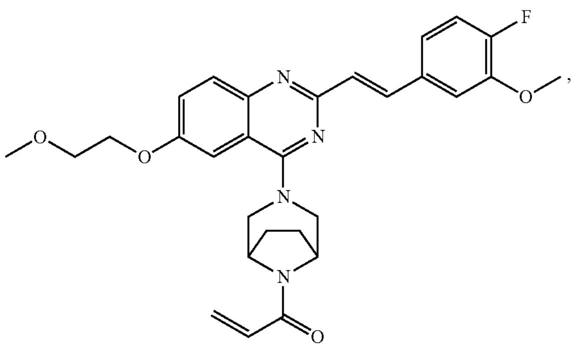
39
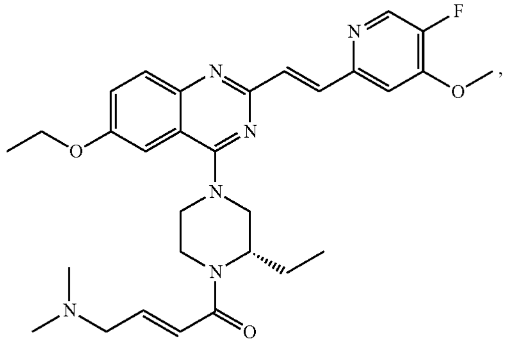
43
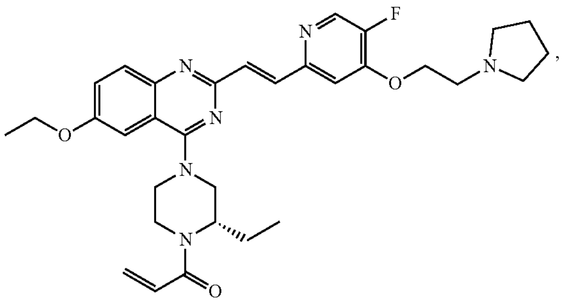
or a pharmaceutically acceptable salt thereof.
28. The compound of claim 27, wherein the compound of Formula III has the structure:
1
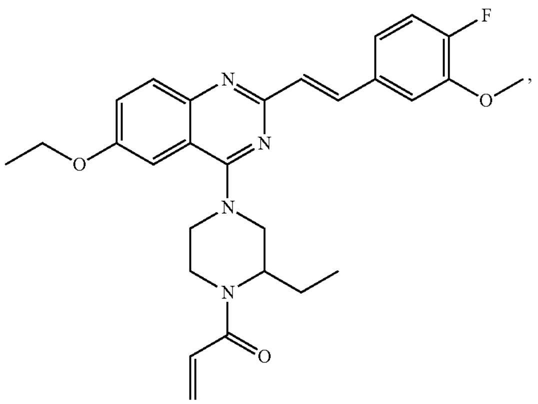
-continued
2
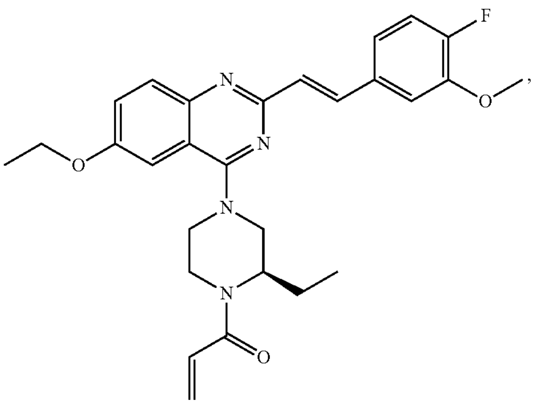
3
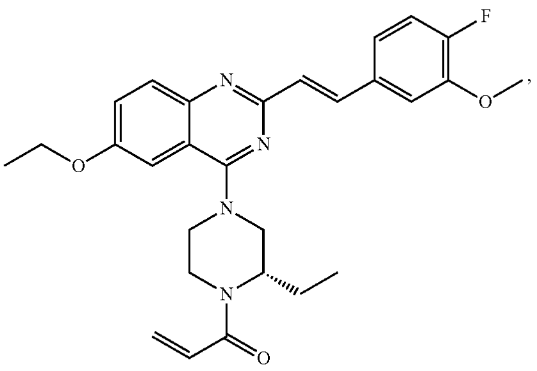
4
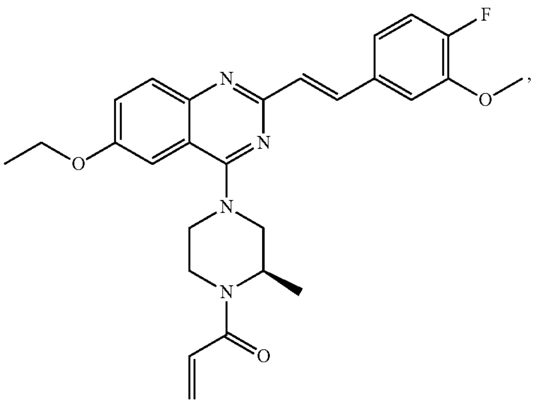
5
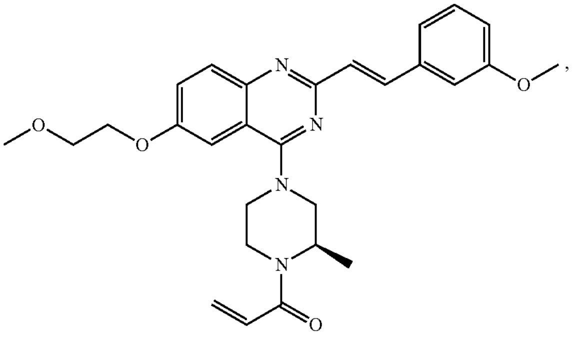

-continued
6
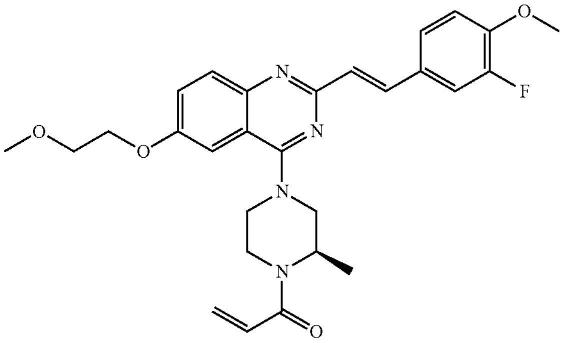
,
15
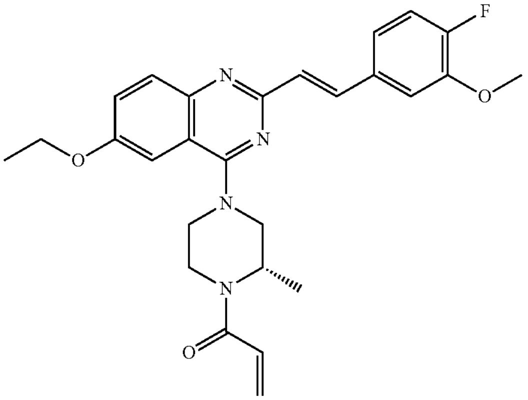
,
16
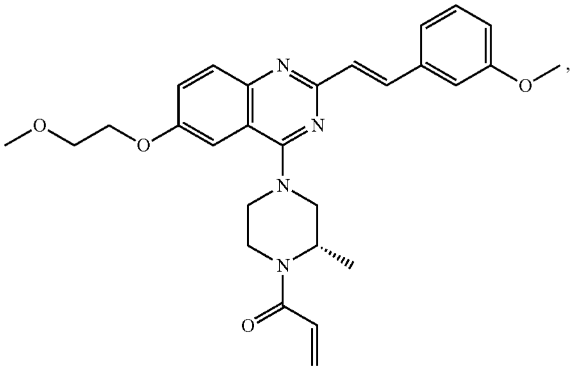
,
17
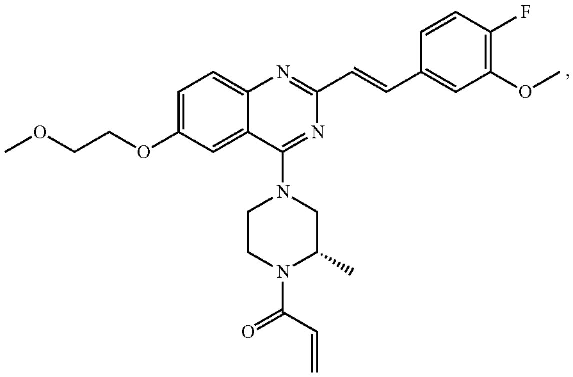
,
or a pharmaceutically acceptable salt thereof.
29. The compound of claim 27, wherein the compound of Formula III has the structure:
14
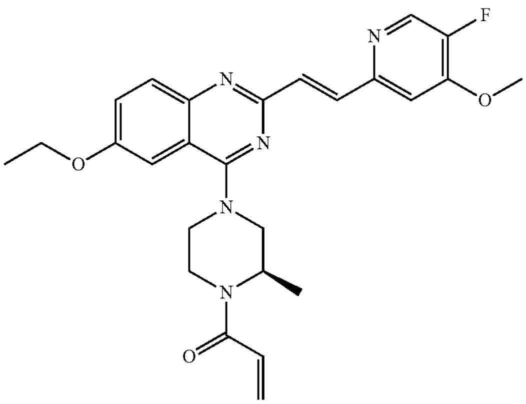
,
29
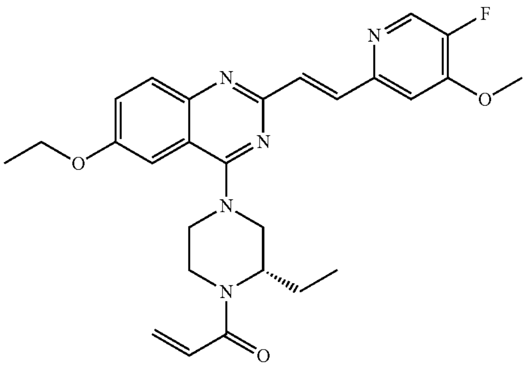
,
31
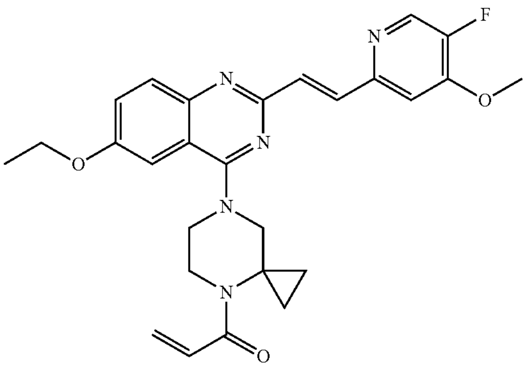
,
39
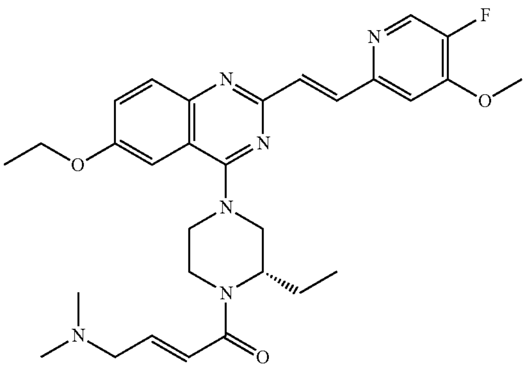
, -continued
43
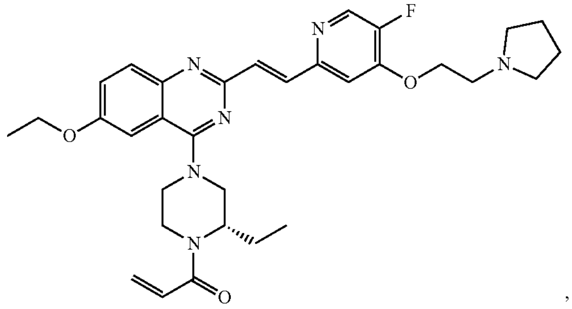
,
or a pharmaceutically acceptable salt thereof.
30. A method of treating an HPV-induced cancer in a subject, comprising administering to the subject a therapeutically effective amount of the compound of claim 1.
* * * * *